(12) United States Patent
Isaacs et al.

(10) Patent No.: US 7,763,614 B2
(45) Date of Patent: Jul. 27, 2010

(54) ISOQUINOLINE POTASSIUM CHANNEL INHIBITORS

(75) Inventors: Richard Isaacs, Harleysville, PA (US); Christopher J. Dinsmore, Newton, MA (US); B. Wesley Trotter, Glenside, NJ (US); Nigel Liverton, Harleysville, PA (US); Douglas C. Beshore, Harleysville, PA (US); Nathan R. Kett, Perkiomenville, PA (US); Charles J. McIntyre, Lansdale, PA (US); Kausik K. Nanda, Norristown, PA (US); David A. Claremon, Maple Glen, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1119 days.

(21) Appl. No.: 10/572,236

(22) PCT Filed: Sep. 22, 2004

(86) PCT No.: PCT/US2004/030945

§ 371 (c)(1),
(2), (4) Date: Mar. 17, 2006

(87) PCT Pub. No.: WO2005/030729

PCT Pub. Date: Apr. 7, 2005

(65) Prior Publication Data

US 2007/0054892 A1    Mar. 8, 2007

Related U.S. Application Data

(60) Provisional application No. 60/505,216, filed on Sep. 23, 2003.

(51) Int. Cl.
C07D 401/02    (2006.01)
A61K 31/47    (2006.01)
(52) U.S. Cl. .................... 514/235.2; 514/253.05; 514/256; 514/309; 544/128; 544/242; 544/363; 546/141
(58) Field of Classification Search ............... None
See application file for complete search history.

(56) References Cited

U.S. PATENT DOCUMENTS

2004/0044030 A1    3/2004    Claremon et al.

FOREIGN PATENT DOCUMENTS

| DE | 287 032 | 2/1991 |
| EP | 0 585 913 A2 | 3/1994 |
| EP | 0 566 069 | 10/2003 |
| WO | WO 02/24655 | 3/2002 |
| WO | WO 02/062764 A1 | 8/2002 |

OTHER PUBLICATIONS

Abdel-Hamid et al, Egyptian Journal of Chemistry (1994), 36 (3), 167-75.*
Natsugari, et al., Journal of Medicinal Chemistry (1996), vol. 38, No. 16, pp. 3106-3120.
Abdel, et al. Egypt Journal of. Chem. (1993), vol. 36, No. 3, pp. 167-175.
Unverferth, et al., Arch. Pharm. (Weinheim) (1991), vol. 324, pp. 809-814.
Supplementary European Search Report for EP 04 78 4700 issued Jul. 11, 2008.

* cited by examiner

*Primary Examiner*—Zinna N Davis
(74) *Attorney, Agent, or Firm*—Heidi M. Struse; Richard S. Parr; Catherine D. Fitch

(57) ABSTRACT

The present invention relates to compounds of structural formula I: I useful as potassium channel inhibitors to treat cardiac arrhythmias, and the like.

(I)

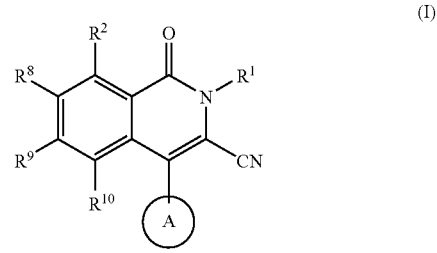

7 Claims, No Drawings

ISOQUINOLINE POTASSIUM CHANNEL INHIBITORS

CROSS REFERENCE TO RELATED APPLICATION

This application is a U.S. National Phase application under 35 U.S.C. §371 of PCT Application No. PCT/US2004/030945, filed Sep. 22, 2004, which claims priority under 35 U.S.C. §119(e) from U.S. Provisional Application Ser. No. 60/505,216, filed Sep. 23, 2003.

BACKGROUND OF THE INVENTION

The present invention relates broadly to compounds that are useful as potassium channel inhibitors. Compounds in this class may be useful as Kv1.5 antagonists for treating and preventing cardiac arrhythmias, and the like, and as Kv1.3 inhibitors for treatment of immunosuppression, autoimmune diseases, and the like.

Voltage gated potassium channels (Kv) are multimeric membrane proteins composed of four $\alpha$ subunits and are often associated with accessory $\beta$ subunits. Kv channels are typically closed at resting membrane potentials, but open upon membrane depolarization. They are involved in the repolarization of the action potential and thus in the electrical excitability of nerve and muscle fibers. The Kv1 class of potassium channels is comprised of at least seven family members, named Kv1.1, Kv1.3, Kv1.5, etc. Functional voltage-gated K$^+$ channels may exist either as homo-oligomers composed of identical subunits, or hetero-oligomers of different subunit composition. This phenomenon is thought to account for the wide diversity of K$^+$ channels. However, subunit compositions of native K$^+$ channels and the physiologic role that particular channels play are, in most cases, still unclear.

The Kv1.3 voltage-gated potassium channel is found in neurons, blood cells, osteoclasts and T-lymphocytes. Membrane depolarization by Kv1.3 inhibition has been shown to be an effective method to prevent T-cell proliferation and therefore has applications in many autoimmune conditions. Inhibition of K$^+$ channels in the plasma membrane of human T-lymphocytes has been postulated to play a role in eliciting immunosuppressive responses by regulating intracellular Ca$^{++}$ homeostasis, which has been found to be important in T-cell activation. Blockade of the Kv1.3 channel has been proposed as a novel mechanism for eliciting an immunosuppressant response (Chandy et al., *J. Exp. Med.* 160: 369, 1984; Decoursey et al., *Nature*, 307: 465, 1984). However, the K$^+$ channel blockers employed in these early studies were non-selective. In later studies, Margatoxin, which blocks only Kv1.3 in T-cells, was shown to exhibit immunosuppressant activity in both in vitro and in vivo models. (Lin et al., *J. Exp. Med*, 177: 637, 1993). The therapeutic utility of this compound, however, is limited by its potent toxicity. Recently, a class of compounds has been reported that may be an attractive alternative to the above-mentioned drugs (U.S. Pat. Nos. 5,670,504; 5,631,282; 5,696,156; 5,679,705; and 5,696,156). While addressing some of the activity/toxicity problems of previous drugs, these compounds tend to be of large molecular weight and are generally produced by synthetic manipulation of a natural product, isolation of which is cumbersome and labor intensive.

Atrial fibrillation (AF) is the most common sustained cardiac arrhythmia in clinical practice and is likely to increase in prevalence with the aging of the population. Conservative estimates indicate that AF affects >2 million Americans, represents over 5% of all admissions for cardiovascular diseases and leads to a 3- to 5-fold increase in the risk of stroke (Kannel et al, *Am. J. Cardiol.*, 82:2N-9N, 1998). While AF is rarely fatal, it can impair cardiac function and lead to complications such as the development of congestive heart failure, thromboembolism, or ventricular fibrillation.

Reentrant excitation (reentry) has been shown to be a prominent mechanism underlying supraventricular arrhythmias in man (Nattel, S., *Nature*, 415:219-226, 2002). Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD) prevents and/or terminates reentrant arrhythmias. Action potential duration is determined by the contributions of the repolarizing potassium currents $I_{Kr}$, $I_{Ks}$, and $I_{Kur}$, and the transient outward current, $I_{to}$. Blockers of any one of these currents would therefore be expected to increase the APD and produce antiarrhythmic effects.

Currently available antiarrhythmic agents have been developed for the treatment of ventricular and atrial/supraventricular arrhythmias. Malignant ventricular arrhythmias are immediately life-threatening and require emergency care. Drug therapy for ventricular arrhythmia includes Class Ia (eg. procainamide, quinidine), Class Ic (eg. flecainide, propafenone), and Class III (amiodarone) agents, which pose significant risks of proarrhythmia. These Class I and III drugs have been shown to convert AF to sinus rhythm and to prevent recurrence of AF (Mounsey, J P, DiMarco, J P, *Circulation*, 102:2665-2670), but pose an unacceptable risk of potentially lethal ventricular proarrhythmia and thus may increase mortality (Pratt, C M, Moye, L A, *Am J. Cardiol.*, 65:20B-29B, 1990; Waldo et al, *Lancet*, 348:7-12, 1996; Torp-Pedersen et al, *Expert Opin. Invest. Drugs*, 9:2695-2704, 2000). These observations demonstrate a clear unmet medical need to develop safer and more efficacious drugs for the treatment of atrial arrhythmias.

Class III antiarrhythmic agents cause a selective prolongation of the APD without significant depression of cardiac conduction or contractile function. The only selective Class III drug approved for clinical use in atrial fibrillation is dofetilide, which mediates its anti-arrhythmic effects by blocking $I_{Kr}$, the rapidly activating component of $I_K$ found in both atrium and ventricle in humans (Mounsey, J P, DiMarco, J P, *Circulation*, 102:2665-2670). Since $I_{Kr}$ blockers increase APD and refractoriness both in atria and ventricle without affecting conduction per se, theoretically they represent potentially useful agents for the treatment of arrhythmias like AF (Torp-Pedersen, et al, *Expert Opin. Invest. Drug*, 9:2695-2704, 2000). However, these agents have the major liability of an enhanced risk of proarrhythmia at slow heart rates. For example, torsades de points has been observed when these compounds are utilized (Roden, D. M. "Current Status of Class III Antiarrhythmic Drug Therapy", *Am J. Cardiol.*, 72:44B-49B, 1993). This exaggerated effect at slow heart rates has been termed "reverse frequency-dependence", and is in contrast to frequency-independent or forward frequency-dependent actions (Hondeghem, L. M. "Development of Class III Antiarrhythmic Agents". *J. Cardiovasc. Cardiol.*, 20 (Suppl. 2):S17-S22). Amiodarone has been shown to possess interesting Class III properties (Singh B. N., Vaughan Williams E. M. "A Third Class Of Anti-Arrhythmic Action: Effects On Atrial And Ventricular Intracellular Potentials And Other Pharmacological Actions On Cardiac Muscle, of MJ 1999 and AH 3747" *Br. J. Pharmacol.*, 39:675-689, 1970; Singh B. N., Vaughan Williams E. M, "The Effect Of Amiodarone, A New Anti-Anginal Drug, On Cardiac Muscle", *Br. J. Pharmacol.*, 39:657-667, 1970), although it is not a selective Class III agent because it effects multiple ion channels; additionally, its use is severely limited due to its side effect profile (Nademanee, K. "The Amiodarone Odyssey". *J. Am. Coll. Cardiol.*, 20:1063-1065, 1992; Fuster et al, *Circulation*, 104:2118-2150, 2001; Bril, A. *Curr. Opin. Pharmacol.* 2:154-159, 2002). Thus, currently available agents such as amiodarone and Class III drugs confer a significant risk of adverse effects including the development of potentially lethal ventricular proarrhythmia.

The ultrarapid delayed rectifier $K^+$ current, $I_{Kur}$, has been observed specifically in human atrium and not in ventricle. The molecular correlate of $I_{Kur}$ in the human atrium is the potassium channel designated Kv1.5. Kv1.5 mRNA (Bertaso, Sharpe, Hendry, and James, *Basic Res. Cardiol.*, 97:424-433, 2002) and protein (Mays, Foose, Philipson, and Tamkun, *J. Clin. Invest.*, 96:282-292, 1995) have been detected in human atrial tissue. In intact human atrial myocytes, an ultra-rapidly activating delayed rectifier $K^+$ current ($I_{Kur}$), also known as the sustained outward current, $I_{sus}$ or $I_{so}$, has been identified and this current has properties and kinetics identical to those expressed by the human $K^+$ channel clone (hKv1.5, HK2) [Wang, Fermini and Nattel, *Circ. Res.*, 73:1061-1076, 1993; Fedida et al., *Circ. Res.* 73:210-216, 1993; Snyders, Tamkun and Bennett, *J. Gen. Physiol.*, 101:513-543, 1993] and a similar clone from rat brain (Swanson et al., *Neuron*, 4:929-939, 1990). Furthermore, because of its rapidity of activation and limited slow inactivation, $I_{Kur}$ is believed to contribute significantly to repolarization in human atrium. Consequently, a specific blocker of $I_{Kur}$, that is a compound which blocks Kv1.5, would overcome the shortcoming of other compounds by prolonging refractoriness through retardation of the repolarization in the human atrium without causing the delays in ventricular repolarization that underlie arrhythmogenic afterdepolarizations and acquired long QT syndrome observed during treatment with current Class III drugs. Kv1.5 blockers exhibiting these properties have been described (Peukert et al, *J. Med. Chem.*, 46:486-498, 2003; Knobloch et al, *Naunyn-Schmedieberg's Arch. Pharmacol.* 366:482-287, 2002; Merck & Co., Inc. WO0224655, 2002).

The compounds described in this invention represent a novel structural class of Kv1.5 antagonist.

SUMMARY OF THE INVENTION

This invention relates to potassium channel inhibitors of general structural Formula I

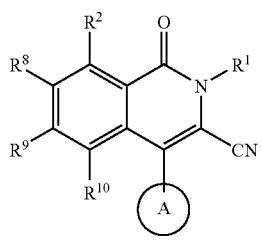

I

The compounds of this invention are useful in the treatment and prevention of cardiac arrhythmias, and the like. Also within the scope of this invention are pharmaceutical formulations comprising a compound of Formula I and a pharmaceutical carrier.

DETAILED DESCRIPTION OF THE DISCLOSURE

The invention is a compound of formula I

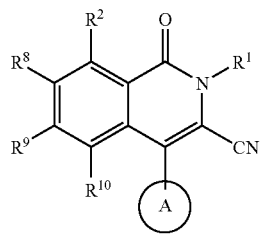

I or a pharmaceutically acceptable salt, crystal form, or hydrate, wherein:
A is
  a) an aryl ring, wherein any stable aryl ring atom is independently unsubstituted or substituted with
    1) halogen,
    2) $NO_2$,
    3) CN,
    4) $CR^{46}=C(R^{47}R^{48})_2$,
    5) $C\equiv CR^{46}$,
    6) $(CR^iR^j)_rOR^{46}$,
    7) $(CR^iR^j)_rN(R^{46}R^{47})$,
    8) $(CR^iR^j)_rC(O)R^{46}$,
    9) $(CR^iR^j)_rC(O)OR^{46}$,
    10) $(CR^iR^j)_rR^{46}$,
    11) $(CR^iR^j)_rS(O)_{0-2}R^{61}$,
    12) $(CR^iR^j)_rS(O)_{0-2}N(R^{46}R^{47})$,
    13) $OS(O)_{0-2}R^{61}$,
    14) $N(R^{46})C(O)R^{47}$,
    15) $N(R^{46})S(O)_{0-2}R^{61}$,
    16) $(CR^iR^j)_rN(R^{46})R^{61}$,
    17) $(CR^iR^j)_rN(R^{46})R^{61}OR^{47}$,
    18) $(CR^iR^j)_rN(R^{46})(CR^kR^l)_sC(O)N(R^{47}R^{48})$,
    19) $N(R^{46})(CR^iR^j)_rR^{61}$,
    20) $N(R^{46})(CR^iR^j)_rN(R^{47}R^{48})$,
    21) $(CR^iR^j)_rC(O)N(R^{47}R^{48})$, or
    22) oxo, or
  b) a heteroaryl ring selected from the group consisting of
    a 5-membered unsaturated monocyclic ring with 1, 2, 3 or 4 heteroatom ring atoms selected from the group consisting or N, O or S,
    a 6-membered unsaturated monocyclic ring with 1, 2, 3 or 4 heteroatom ring atoms selected from the group consisting N, O and S, and
    a 9- or 10-membered unsaturated bicyclic ring with 1, 2, 3 or 4 heteroatom ring atoms selected from the group consisting or N, O or S;

wherein any stable S heteroaryl ring atom is unsubstituted or mono- or di-substituted with oxo, and any stable C or N heteroaryl ring atom is independently unsubstituted or substituted with
    1) halogen,
    2) $NO_2$,
    3) CN,
    4) $CR^{46}=C(R^{47}R^{48})_2$,
    5) $C\equiv C^{46}$,
    6) $(CR^iR^j)_rOR^{46}$,
    7) $(CR^iR^j)_rN(R^{46}R^{47})$,
    8) $(CR^iR^j)_rC(O)R^{46}$, 9) $(CR^iR^j)_rC(O)OR^{46}$,
10) $(CR^iR^j)_rR^{46}$,
11) $(CR^iR^j)_rS(O)_{0-2}R^{61}$,
12) $(CR^iR^j)_rS(O)_{0-2}N(R^{46}R^{47})$,
13) $OS(O)_{0-2}R^{61}$,
14) $N(R^{46})C(O)R^{47}$,
15) $N(R^{46})S(O)_{0-2}R^{61}$,
16) $(CR^iR^j)_rN(R^{46})R^{61}$,
17) $(CR^iR^j)_rN(R^{46})R^{61}OR^{47}$,
18) $(CR^iR^j)_rN(R^{46})(CR^kR^l)_sC(O)N(R^{47}R^{48})$,
19) $N(R^{46})(CR^iR^j)_rR^{61}$,
20) $N(R^{46})(CR^iR^j)_rN(R^{47}R^{48})$,
21) $(CR^iR^j)_rC(O)N(R^{47}R^{48})$, or
22) oxo;

$R^1$ is selected from the group consisting of
1) hydrogen,
2) $(CR^aR^b)_nR^{40}$
3) $(CR^aR^b)_nOR^{40}$,
4) $(CR^aR^b)_nN(R^{40}R^{41})$,
5) $(CR^aR^b)_nN(R^{40})C(O)OR^{41}$,
6) $(CR^aR^b)_nN(R^{40})(CR^cR^d)_2N(R^{41})C(O)R^{49}$,
7) $C_{3-8}$ cycloalkyl,
8) $(CR^aR^b)_nC(O)OR^{40}$,
9) $(CR^aR^b)_nN(R^{40})(CR^cR^d)_{1-3}R^{41}$,
10) $(CR^aR^b)_nS(O)_{0-2}R^6$,
11) $(CR^aR^b)_nS(O)_{0-2}N(R^{40}R^{41})$,
12) $(CR^aR^b)_nN(R^{40})R^6OR^{41}$,
13) $(CR^aR^b)_nN(R^{40})(CR^cR^d)_{0-6}C(O)N(R^{41}R^{42})$;

$R^2$, $R^8$, $R^9$ and $R^{10}$ are independently selected from:
1) hydrogen,
2) halogen,
3) $NO_2$,
4) CN,
5) $CR^{43}=C(R^{44}R^{45})$,
6) $C\equiv CR^{43}$,
7) $(CR^eR^f)_pOR^{43}$,
8) $(CR^eR^f)_pN(R^{43}R^{44})$,
9) $(CR^eR^f)_pC(O)R^{43}$,
10) $(CR^eR^f)_pC(O)OR^{43}$,
11) $(CR^eR^f)_pR^{43}$,
12) $(CR^eR^f)_pS(O)_{0-2}R^{60}$,
13) $(CR^eR^f)_pS(O)_{0-2}N(R^{43}R^{44})$,
14) $OS(O)_{0-2}R^{60}$,
15) $N(R^{43})C(O)R^{44}$,
16) $N(R^{43})S(O)_{0-2}R^{60}$,
17) $(CR^eR^f)_pN(R^{43})R^{60}$,
18) $(CR^eR^f)_pN(R^{43})R^{60}OR^{44}$,
19) $(CR^eR^f)_pN(R^{43})(CR^gR^h)_qC(O)N(R^{44}R^{45})$,
20) $N(R^{43})(CR^eR^f)_pR^{60}$,
21) $N(R^{43})(CR^eR^f)_pN(R^{44}R^{45})$, and
22) $(CR^eR^f)_pC(O)N(R^{43}R^{44})$, or $R^2$ and $R^8$ are independently as defined above, and $R^9$ and $R^{10}$, together with the atoms to which they are attached, form the ring

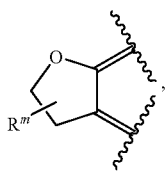

where $R^m$ is $C_{1-6}$alkyl;

$R^a$, $R^b$, $R^c$, $R^d$, $R^e$, $R^f$, $R^g$, $R^h$, $R^i$, $R^j$, $R^k$ and $R^l$ are independently selected from the group consisting of:
1) hydrogen,
2) $C_1$-$C_6$ alkyl,
3) halogen,
4) aryl,
5) $R^{80}$,
6) $C_3$-$C_{10}$ cycloalkyl, and
7) $OR^4$,
said alkyl, aryl, and cycloalkyl being unsubstituted, monosubstituted with $R^7$, disubstituted with $R^7$ and $R^{15}$, trisubstituted with $R^7$, $R^{15}$ and $R^{16}$, or tetrasubstituted with $R^7$, $R^{15}$, $R^{16}$ and $R^{17}$;

$R^4$, $R^{40}$, $R^{41}$, $R^{42}$, $R^{43}$, $R^{44}$, $R^{45}$, $R^{46}$, $R^{47}$, $R^{48}$, $R^{49}$, $R^{51}$, and $R^{52}$ are independently selected from the group consisting of
1) hydrogen,
2) $C_1$-$C_6$ alkyl,
3) $C_3$-$C_{10}$ cycloalkyl,
4) aryl,
5) $R^{81}$,
6) $CF_3$,
7) $C_2$-$C_6$ alkenyl, and
8) $C_2$-$C_6$ alkynyl,
said alkyl, aryl, and cycloalkyl is unsubstituted, monosubstituted with $R^{18}$, di-substituted with $R^{18}$ and $R^{19}$, tri-substituted with $R^{18}$, $R^{19}$ and $R^{20}$, or tetra-substituted with $R^{18}$, $R^{19}$, $R^{20}$ and $R^{21}$;

$R^6$, $R^{60}$, $R^{61}$, and $R^{62}$ are independently selected from the group consisting of
1) $C_1$-$C_6$ alkyl,
2) aryl,
3) $R^{83}$, and
4) $C_3$-$C_{10}$ cycloalkyl;
said alkyl, aryl, and cycloalkyl is unsubstituted, monosubstituted with $R^{26}$, di-substituted with $R^{26}$ and $R^{27}$, tri-substituted with $R^{26}$, $R^{27}$ and $R^{28}$, or tetra-substituted with $R^{26}$, $R^{27}$, $R^{28}$ and $R^{29}$;

$R^7$, $R^{15}$, $R^{16}$, $R^{17}$, $R^{18}$, $R^{19}$, $R^{20}$, $R^{21}$, $R^{26}$, $R^{27}$, $R^{28}$, and $R^{29}$ are independently selected from the group consisting of
1) $C_1$-$C_6$alkyl,
2) halogen,
3) $OR^{51}$,
4) $CF_3$,
5) aryl,
6) $C_3$-$C_{10}$ cycloalkyl,
7) $R^{84}$,
8) $S(O)_{0-2}N(R^{51}R^{52})$,
9) $C(O)OR^{51}$,
10) $C(O)R^{51}$,
11) CN,
12) $C(O)N(R^{51}R^{52})$,
13) $N(R^{51})C(O)R^{52}$,
14) $S(O)_{0-2}R^{62}$,
15) $NO_2$, and
16) $N(R^{51}R^{52})$;

$R^{80}$, $R^{81}$, $R^{83}$, and $R^{84}$ are independently selected from a group of unsubstituted or substituted heterocyclic rings consisting of a 4-6 membered or saturated monocyclic ring with 1, 2, 3 or 4 heteroatom ring atoms selected from the group consisting N, O and S, and a 9- or 10-membered unsaturated or saturated bicyclic ring with 1, 2, 3 or 4 heteroatom ring atoms selected from the group consisting or N, O or S; and n, p, q, r, and s are independently 0, 1, 2, 3, 4, 5 or 6.

In a class of compounds of the invention, and pharmaceutically acceptable salts thereof, A is an aryl ring selected from phenyl, unsubstituted or substituted as defined above, or a heteroaryl ring, unsubstituted or substituted as defined above, selected from the group consisting of pyridine, pyrimidine, pyrazine, pyridazine, indole, pyrrolopyridine, benzimidazole, benzoxazole, benzothiazole, and benzoxadiazole;

$R^2$, $R^8$, $R^9$ and $R^{10}$ are independently selected from the group consisting of:
1) hydrogen,
2) halogen,
3) $OR^{43}$, and
4) $(CR^eR^f)_pR^{43}$, or $R^2$ and $R^8$ are independently as defined above, and $R^9$ and $R^{10}$, together with the atoms to which they are attached, form the ring

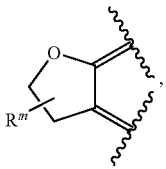

where $R^m$ is $C_{1-6}$alkyl; and
$R^1$ is selected from the group consisting of
1) hydrogen,
2) $(CR^aR^b)_{1-2}R^{40}$
3) $(CR^aR^b)_{1-2}OR^{40}$,
4) $(CR^aR^b)_{1-2}N(R^{40}R^{41})$,
5) $(CR^aR^b)_{1-2}N(R^{40})C(O)OR^{41}$,
6) $(CR^aR^b)_{1-2}N(R^{40})(CR^cR^d)_2N(R^{41})C(O)R^{49}$,
7) $(CR^aR^b)_{1-2}C(O)OR^{40}$,
8) $(CR^aR^b)_{1-2}N(R^{40})(CR^cR^d)_{1-3}R^{41}$, and
9) cyclopropyl.

In a subclass of this class of compounds of the invention, and pharmaceutically acceptable salts thereof,
$R^2$ is hydrogen,
$R^8$ is hydrogen or halogen,
$R^{10}$ is hydrogen or halogen, and
$R^9$ are independently selected from the group consisting of
1) hydrogen,
2) halogen,
3) $OR^{43}$, and
4) $(CR^eR^f)_pR^{43}$, or $R^2$ and $R^8$ are independently as defined above, and $R^9$ and $R^{10}$, together with the atoms to which they are attached, form the ring

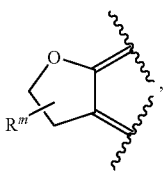

where $R^m$ is $C_{1-6}$alkyl.

In a group of this subclass of compounds and pharmaceutically acceptable salts thereof,
$R^1$ is selected from the group consisting of
—$CH_2)_2OH$, —$(CH_2)_2Cl$, —$CH_3$, hydrogen, —$CH_2)_2N(CH_3)_2$, —$CH_2CH(OCH_2CH_3)_2$,
—$CH_2)_3CH_3$, —$(CH_2)_2NHC(O)OC(CH_3)_3$, —$(CH_2)_2NHC(CH_3)_3$, —$CH_2)_2N(CH_2CH_3)_2$,
—$(CH_2)_2NHCH(CH_3)_2$, —$(CH_2)_2NH(CH_2)C(CH_3)_3$, —$CH_2)_2NH(CH_2)_2NHC(O)CH_3$,
—$CH_2CH(OH)CH_2OH$, c($C_3H_5$), —$CH_2CHCH_2$, —$CH_2)_2N(CH_3)(CH_2)_2OCH_3$,
—$CH_2)_2N(CH_3)(CH_2)_2OH$, —$(CH_2)_2NH(CH_2)OCH_3$, —$CH_2CF_3$, —$CH_2CHCH_2$,
—$CH_2)_2OH$, —$(CH_2)_2NH(CH_2)_2OH$, —$CH_2)_3OH$, —$CH_2CH(OH)CH_2N(CH_3)_2$,
—$CH_2CH(NH_2)CH_2OH$, —$CH_2CH(N(CH_3)_2)CH_2OH$, —$CH_2CH(OH)CH_2OCH(CH_3)_2$, —$CH_2C(O)OCH_2CH_3$, —$CH_2CH(OH)CH_2OCH_2CH_3$, —$CH_2CH(OH)CH_2OCH_3$,
—$CH_2CH(OH)CH_2CH_3$, —$CH_2CH(OH)CH_3$, —$CH_2C(OH)(CH_3)_2$, —$CH_2C(O)OH$, —$CH(CH_3)C(O)OCH_3$,

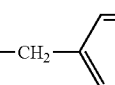, 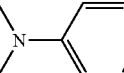,

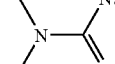,

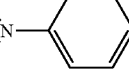,

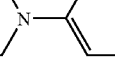,

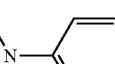,

,

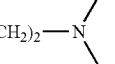, 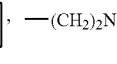,

—$(CH_2)_2NHCH(C_6H_5)_2$, 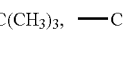,

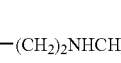, 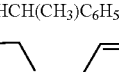,

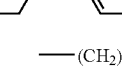, ,

—$(CH_2)_2NHC_6H_5$, —$(CH_2)_2NH(CH_2)_4C_6H_5$,

—$(CH_2)_2NH(CH_2)_3C_6H_5$, —$(CH_2)_2NHCH_2$—,

—$(CH_2)_2NHCH(CH_3)C_6H_5$,

,

, —$(CH_2)_2NHCH(C_6H_5)_2$,

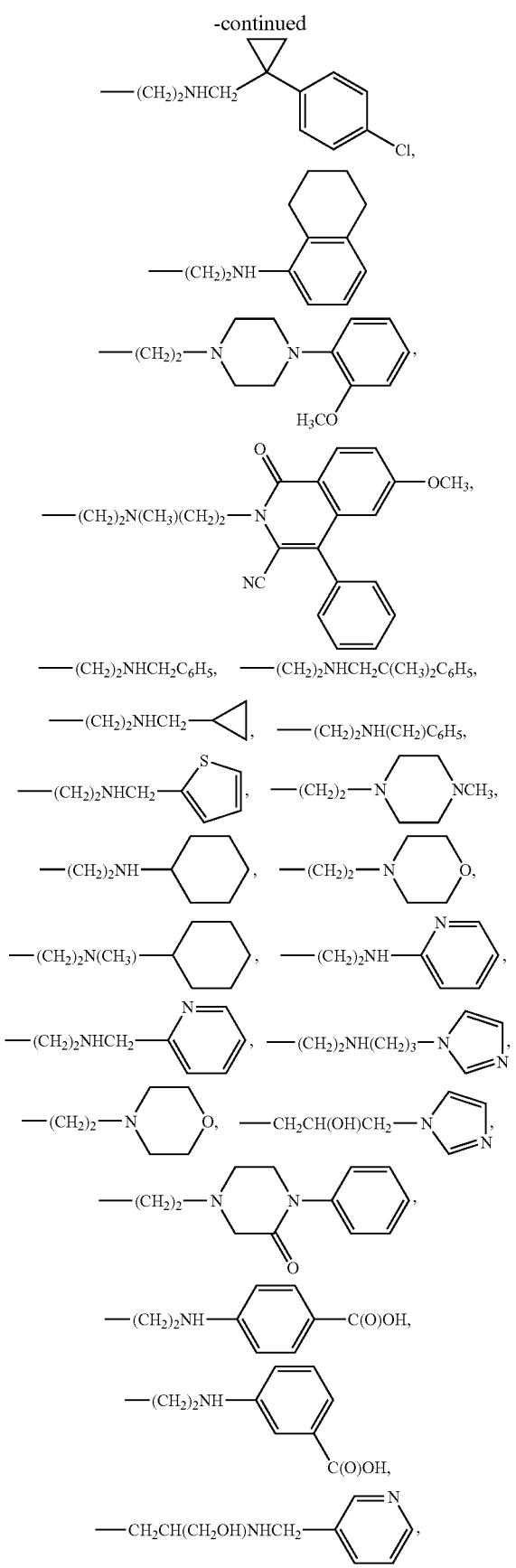
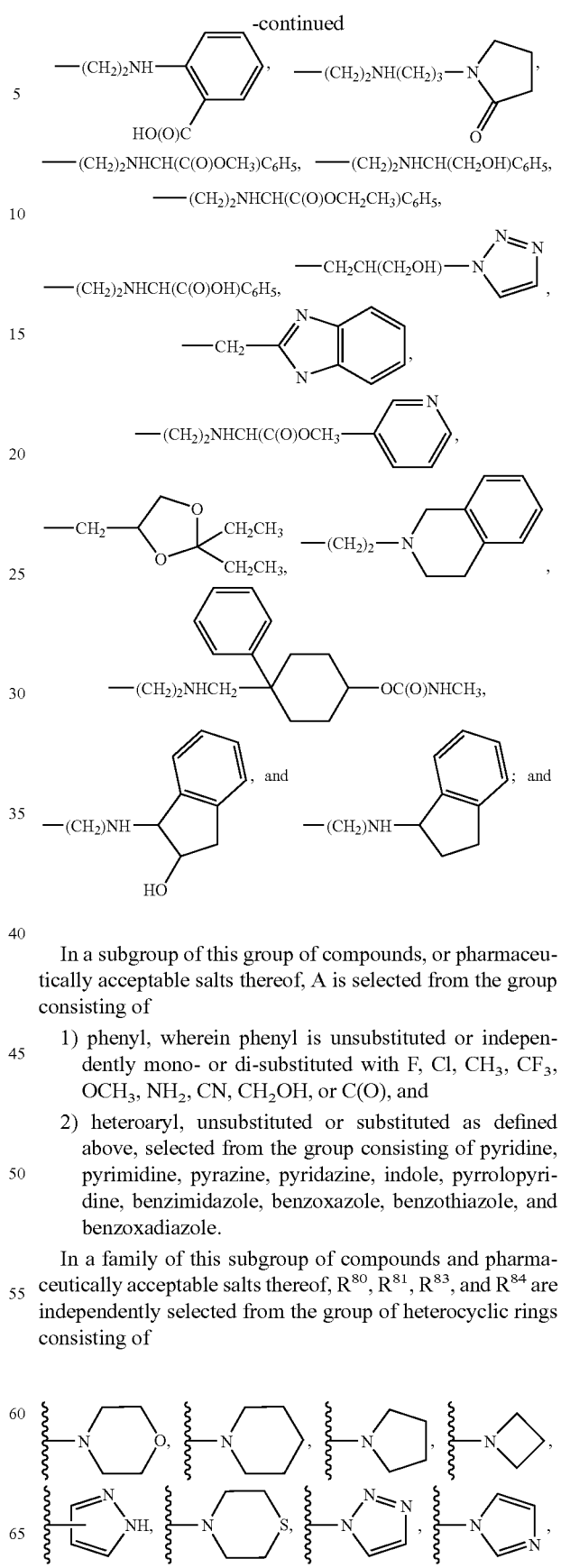

In a subgroup of this group of compounds, or pharmaceutically acceptable salts thereof, A is selected from the group consisting of 1) phenyl, wherein phenyl is unsubstituted or independently mono- or di-substituted with F, Cl, $CH_3$, $CF_3$, $OCH_3$, $NH_2$, CN, $CH_2OH$, or C(O), and
2) heteroaryl, unsubstituted or substituted as defined above, selected from the group consisting of pyridine, pyrimidine, pyrazine, pyridazine, indole, pyrrolopyridine, benzimidazole, benzoxazole, benzothiazole, and benzoxadiazole.

In a family of this subgroup of compounds and pharmaceutically acceptable salts thereof, $R^{80}$, $R^{81}$, $R^{83}$, and $R^{84}$ are independently selected from the group of heterocyclic rings consisting of -continued

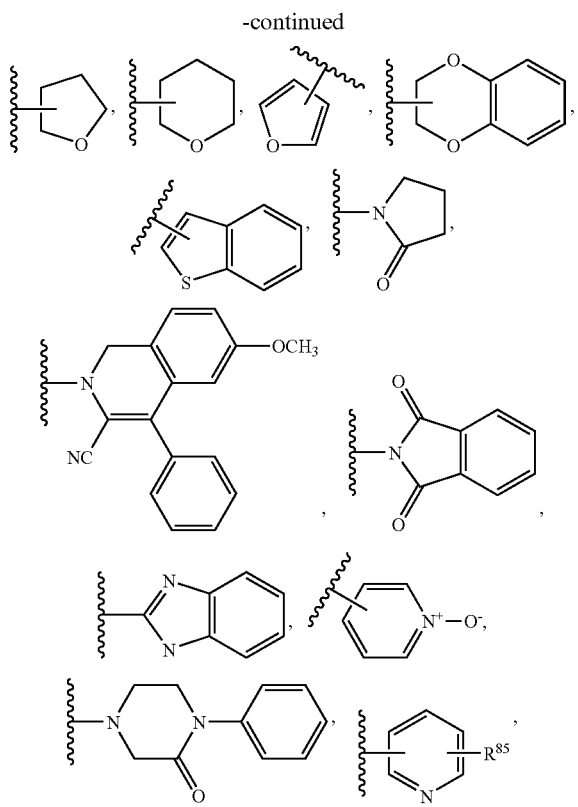

where R⁸⁵ is selected from the group consisting of hydrogen, NH₂, NO₂, and CH₃,

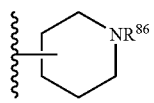

where R⁸⁶ is selected from the group consisting of hydrogen and —C(O)OC(CH₃)₃,

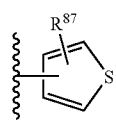

where R⁸⁷ is selected from the group consisting of hydrogen and —CH₂OH,

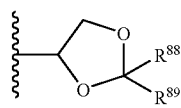

wherein R⁸⁸ and R⁸⁹ are independently selected from the group consisting of hydrogen, CH₃ and CH₂CH₃, and

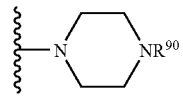

wherein R⁹⁰ is selected from the group consisting of hydrogen,

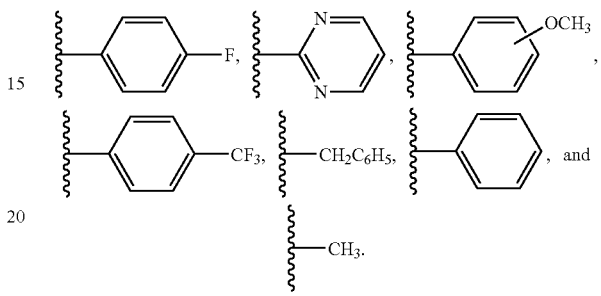

In a subfamily of this family of compounds, or pharmaceutically acceptable salts thereof, R⁹ is selected from the group consisting of
—OCH₃, —CH₃, —CH₂CH₃, Cl, —SCH₃, I, Br, F, CF₃,
—O(CH₂)₂NH₂, —OCH₂C(O)OH, —CH₂NH₂, —CH(OH)CH₃, —OH, —OCH₂CF₃,
—OCH₂CHCH₂, —O(CH₂)₂OCH₃, —OCH₂CH(OH)CH₂OH, —CH(NH₂)CH₃, —OCH₂F,
—O(CH₂)₂CH₃, —O(CH₂)₂OCH₂CH₃, —OCH₂C(O)OCH₂CH₃, —O(CH₂)₂OH,
—O(CH₂)₃OH, —OCHF₂, —OCH₂C(O)N(CH₃)₂, —O(CH₂)₃C(O)OCH₂CH₃, —O(CH₂)₄C(O)OCH₂CH₃,
—OCHCH₂, —O(CH₂)₂N(CH₃)₂, —O(CH₂)₃N(CH₃)₂,
—O(CH₂)₆NH₂, —C(CH₂)₃C(O)OH, —O(CH₂)₄C(O)OH, —O(CH₂)₄NH₂,
—O(CH₂)₅OC(O)CH₃, —OCH₂CN, —O(CH₂)₅OH, —OC(O)CH₃, —OSO₂CH₃,
—OCH₂C(O)C(CH₃)₃,

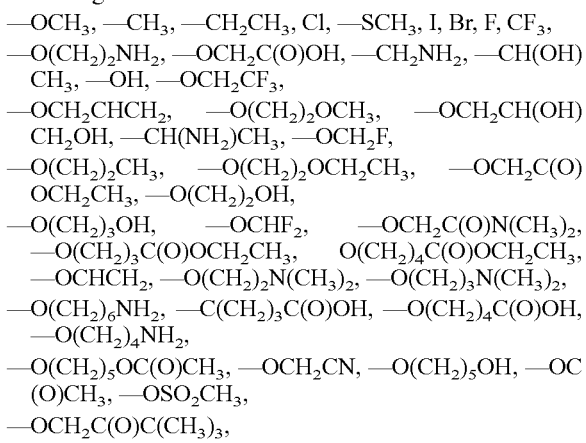
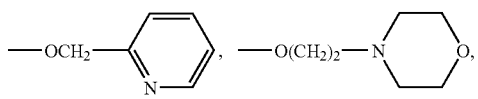
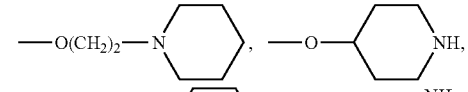
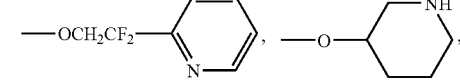
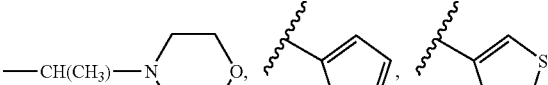
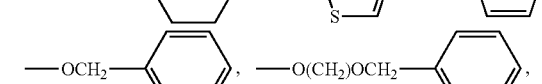
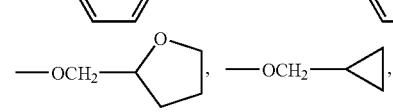

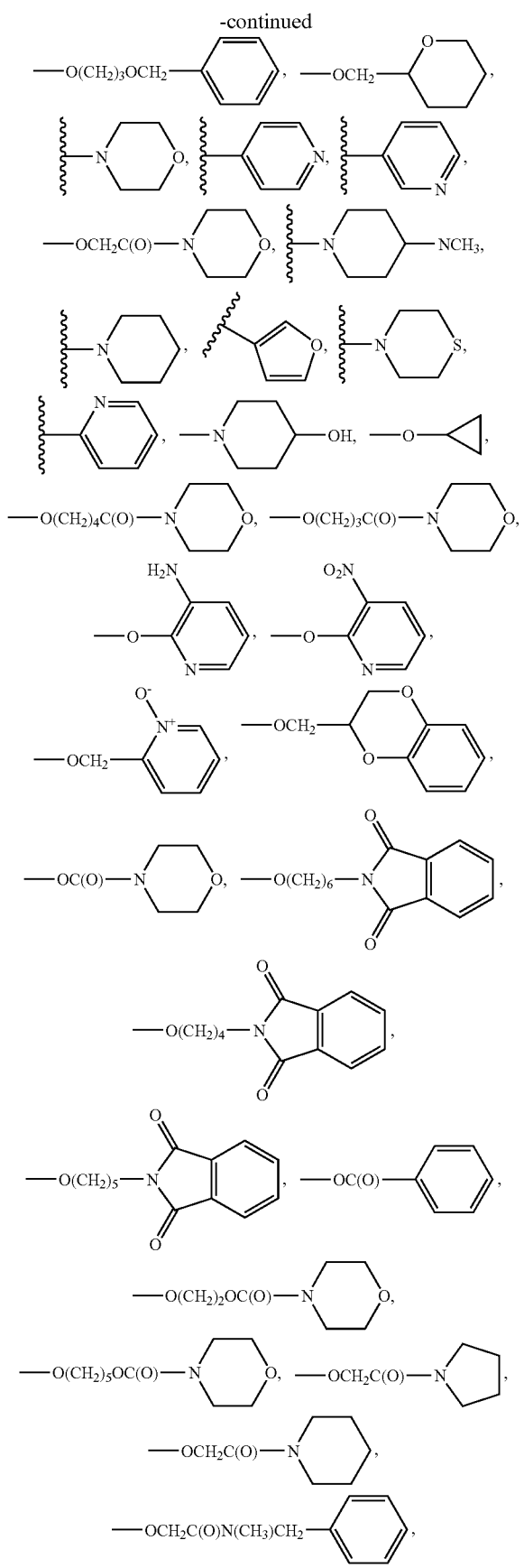
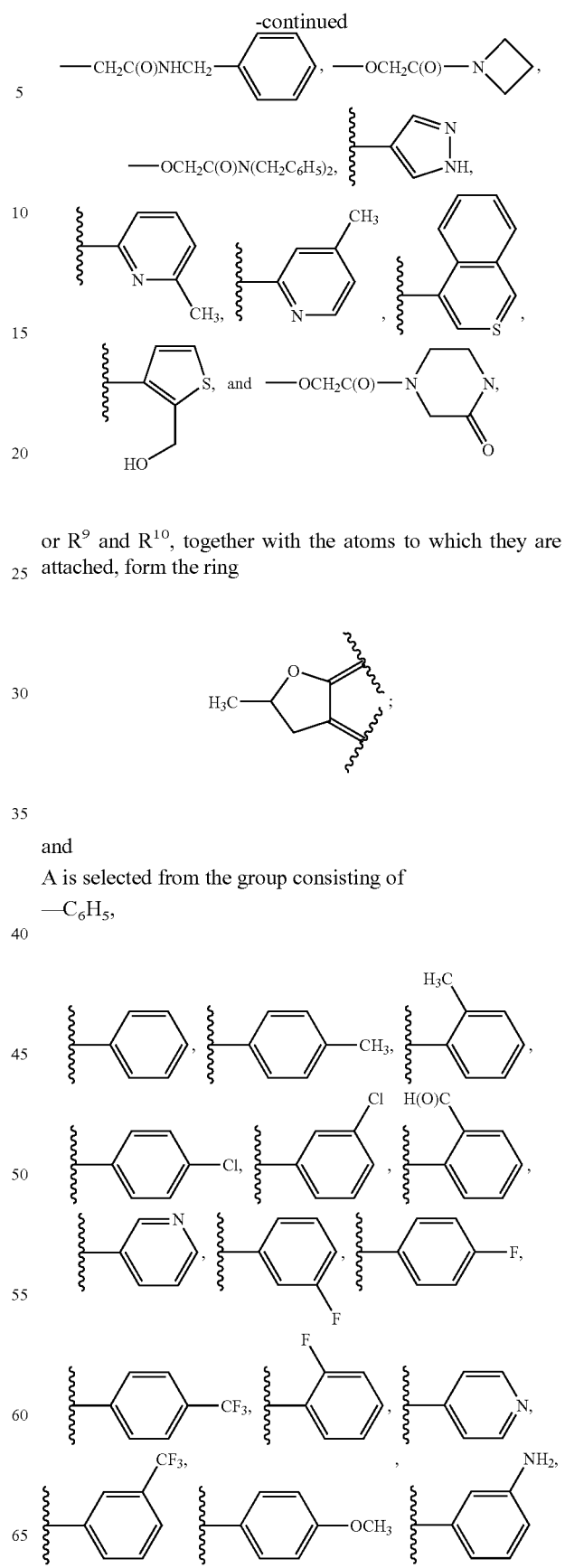
or $R^9$ and $R^{10}$, together with the atoms to which they are attached, form the ring
and
A is selected from the group consisting of
—$C_6H_5$,

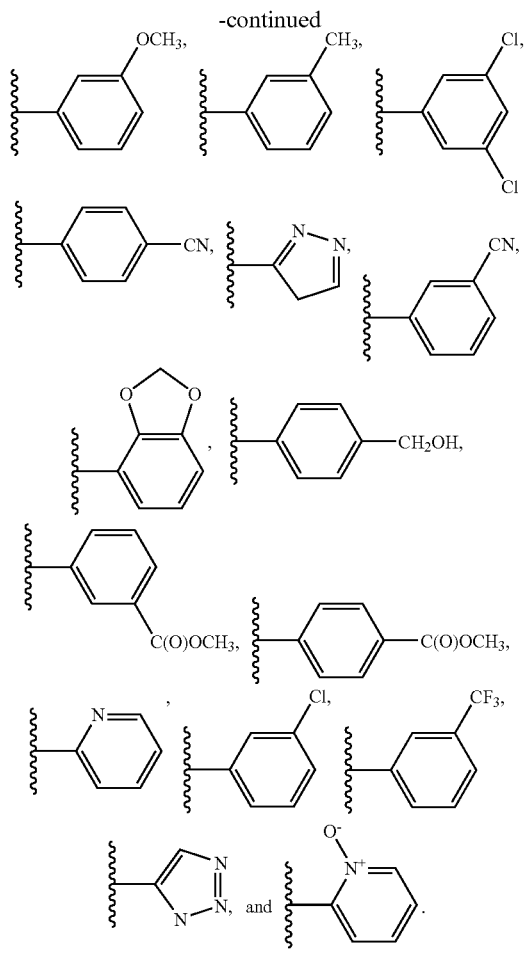

Specific examples of this subgroup include the following compounds:

6-methoxy-1-oxo-4-phenyl-2-[2-(5,6,7,8-tetrahydronaphthalen-1-ylamino)ethyl]-1,2-dihydroisoquinoline-3-carbonitrile,
2-(2-hydroxyethyl)-6-methoxy-1-oxo-4-phenyl-1,2-dihydroisoquinoline-3-carbonitrile,
2-(2-chloroethyl)-6-methoxy-1-oxo-4-phenyl-1,2-dihydroisoquinoline-3-carbonitrile,
2-[2-(cyclopropylamino)ethyl]-6-methoxy-1-oxo-4-phenyl-1,2-dihydroisoquinoline-3-carbonitrile,
6-methoxy-2-(4-methoxybenzyl)-1-oxo-4-phenyl-1,2-dihydroisoquinoline-3-carbonitrile,
2,6-dimethyl-1-oxo-4-phenyl-1,2-dihydroisoquinoline-3-carbonitrile,
6-ethyl-2-methyl-1-oxo-4-phenyl-1,2-dihydroisoquinoline-3-carbonitrile,
6-methoxy-1-oxo-4-phenyl-1,2-dihydroisoquinoline-3-carbonitrile,
2-[2-(dimethylamino)ethyl]-6-methoxy-1-oxo-4-phenyl-1,2-dihydroisoquinoline-3-carbonitrile,
6-methoxy-1-oxo-4-phenyl-2-[2-(4-pyrimidin-2-ylpiperazin-1-yl)ethyl]-1,2-dihydroisoquinoline-3-carbonitrile,
6-methoxy-2-{2-[4-(4-methoxyphenyl)piperazin-1-yl]ethyl}-1-oxo-4-phenyl-1,2-dihydroisoquinoline-3-carbonitrile,
6-methoxy-2-{2-[4-(3-methoxyphenyl)piperazin-1-yl]ethyl}-1-oxo-4-phenyl-1,2-dihydroisoquinoline-3-carbonitrile,
6-methoxy-2-{2-[4-(2-methoxyphenyl)piperazin-1-yl]ethyl}-1-oxo-4-phenyl-1,2-dihydroisoquinoline-3-carbonitrile,
2-{2-[4-(4-fluorophenyl)piperazin-1-yl]ethyl}-6-methoxy-1-oxo-4-phenyl-1,2-dihydroisoquinoline-3-carbonitrile,
6-methoxy-1-oxo-4-phenyl-2-(2-{4-[4-(trifluoromethyl)phenyl]piperazin-1-yl}ethyl)-1,2-dihydroisoquinoline-3-carbonitrile,
6-methoxy-2-methyl-1-oxo-4-phenyl-1,2-dihydroisoquinoline-3-carbonitrile,
2-(2,2-diethoxyethyl)-6-methoxy-1-oxo-4-phenyl-1,2-dihydroisoquinoline-3-carbonitrile,
6-methoxy-2-methyl-4-(4-methylphenyl)-1-oxo-1,2-dihydroisoquinoline-3-carbonitrile,
2-butyl-6-methoxy-1-oxo-4-phenyl-1,2-dihydroisoquinoline-3-carbonitrile,
tert-butyl[2-(3-cyano-6-methoxy-1-oxo-4-phenylisoquinolin-2(1H)-yl)ethyl]-carbamate,
6-methoxy-2-methyl-4-(2-methylphenyl)-1-oxo-1,2-dihydroisoquinoline-3-carbonitrile,
6-methoxy-2-methyl-4-(2-methylphenyl)-1-oxo-1,2-dihydroisoquinoline-3-carbonitrile,
4-(4-chlorophenyl)-6-methoxy-2-methyl-1-oxo-1,2-dihydroisoquinoline-3-carbonitrile,
4-(3-chlorophenyl)-6-methoxy-2-methyl-1-oxo-1,2-dihydroisoquinoline-3-carbonitrile,
4-(2-formylphenyl)-6-methoxy-2-methyl-1-oxo-1,2-dihydroisoquinoline-3-carbonitrile,
6-chloro-2-methyl-1-oxo-4-phenyl-1,2-dihydroisoquinoline-3-carbonitrile,
6-iodo-2-methyl-1-oxo-4-phenyl-1,2-dihydroisoquinoline-3-carbonitrile,
1-[2-(3-cyano-6-methoxy-1-oxo-4-phenylisoquinolin-2(1H)-yl)ethyl]pyrrolidinium trifluoroacetate,
N-[2-(3-cyano-6-methoxy-1-oxo-4-phenylisoquinolin-2(1H)-yl)ethyl]-2-phenylbutan-1-aminium trifluoroacetate,
N-[2-(3-cyano-6-methoxy-1-oxo-4-phenylisoquinolin-2(1H)-yl)ethyl]-2,2-diphenylethanaminium trifluoroacetate,
2-[2-(4-benzylpiperazin-1-yl)ethyl]-6-methoxy-1-oxo-4-phenyl-1,2-dihydroisoquinoline-3-carbonitrile,
N-[2-(3-cyano-6-methoxy-1-oxo-4-phenylisoquinolin-2(1H)-yl)ethyl]indan-2-aminium trifluoroacetate,
N-{[1-(4-chlorophenyl)cyclopropyl]methyl}-2-(3-cyano-6-methoxy-1-oxo-4-phenylisoquinolin-2(1H)-yl)ethanaminium trifluoroacetate,
6-methoxy-1-oxo-4-phenyl-2-{2-[(pyridin-4-ylmethyl)amino]ethyl}-1,2-dihydroisoquinoline-3-carbonitrile,
tert-butyl4-[(3-cyano-6-methoxy-1-oxo-4-phenylisoquinolin-2(1H)-yl)methyl]-piperidine-1-carboxylate,
6-bromo-2-methyl-1-oxo-4-phenyl-1,2-dihydroisoquinoline-3-carbonitrile,
N-(3-cyano-2-methyl-1-oxo-4-phenyl-1,2-dihydroisoquinolin-6-yl)-N-hydroxyacetamide,
N-(3-cyano-2-methyl-1-oxo-4-phenyl-1,2-dihydroisoquinolin-6-yl)-N-[(methylsulfonyl)oxy]methanesulfonamide,
4-[(3-cyano-6-methoxy-1-oxo-4-phenylisoquinolin-2(1H)-yl)methyl]piperidinium chloride,
6-fluoro-2-methyl-1-oxo-4-phenyl-1,2-dihydroisoquinoline-3-carbonitrile,
N-[2-(3-cyano-6-methoxy-1-oxo-4-phenylisoquinolin-2(1H)-yl)ethyl]benzenaminium trifluoroacetate,
N-[2-(3-cyano-6-methoxy-1-oxo-4-phenylisoquinolin-2(1H)-yl)ethyl]-4-phenylbutan-1-aminium trifluoroacetate.

N-[2-(3-cyano-6-methoxy-1-oxo-4-phenylisoquinolin-2 (1H)-yl)ethyl]-3-phenylpropan-1-aminium trifluoroacetate,
N-[2-(3-cyano-methoxy-1-oxo-4-phenylisoquinolin-2(1H)-yl)ethyl]-2-methylpropan-2-aminium trifluoroacetate,
2-(3-cyano-6-methoxy-1-oxo-4-phenylisoquinolin-2(1H)-yl)-N-(cyclohexylmethyl)-ethanaminium trifluoroacetate,
(1S)-N-[2-(3-cyano-6-methoxy-1-oxo-4-phenylisoquinolin-2(1H)-yl)ethyl]-1-phenylethanaminium trifluoroacetate,
6-methoxy-1-oxo-4-phenyl-2-[2-(4-phenylpiperazin-1-yl) ethyl]-1,2-dihydroisoquinoline-3-carbonitrile,
1-[2-(3-cyano-6-methoxy-1-oxo-4-phenylisoquinolin-2 (1H)-yl)ethyl]piperidinium trifluoroacetate,
2-(3-cyano-6-methoxy-1-oxo-4-phenylisoquinolin-2(1H)-yl)-N-(diphenylmethyl)-ethanaminium trifluoroacetate,
2-(3-cyano-6-methoxy-1-oxo-4-phenylisoquinolin-2(1H)-yl)-N-[2-(3-cyano-6-methoxy-1-oxo-4-phenylisoquinolin-2(1H)-yl)ethyl]-N-methylethanaminium trifluoroacetate,
2-(3-cyano-6-methoxy-1-oxo-4-phenylisoquinolin-2(1H)-yl)-N,N-diethylethanaminium trifluoroacetate,
N-benzyl-2-(3-cyano-6-methoxy-1-oxo-4-phenylisoquinolin-2(1H)ethanaminium trifluoroacetate,
2-(3-cyano-6-methoxy-1-oxo-4-phenylisoquinolin-2(1H)-yl)-N-[(trans-4-{[(methylamino)-carbonyl]oxy}-1-phenylcyclohexyl)methyl]ethanaminium trifluoroacetate,
N-[2-(3-cyano-6-methoxy-1-oxo-4-phenylisoquinolin-2 (1H)-yl)ethyl]-2-methyl-2-phenylpropan-1-aminium trifluoroacetate,
2-[2-(3-cyano-6-methoxy-1-oxo-4-phenylisoquinolin-2 (1H)-yl)ethyl]-1,2,3,4-tetrahydroisoquinolinium trifluoroacetate,
2-(3-cyano-6-methoxy-1-oxo-4-phenylisoquinolin-2(1H)-yl)-N-(2-thienylmethyl)-ethanaminium trifluoroacetate,
N-[2-(3-cyano-6-methoxy-1-oxo-4-phenylisoquinolin-2 (1H)-yl)ethyl]indan-1-aminium trifluoroacetate,
6-methoxy-2-[2-(4-methylpiperazin-1-yl)ethyl]-1-oxo-4-phenyl-1,2-dihydroisoquinoline-3-carbonitrile,
4-[2-(3-cyano-6-methoxy-1-oxo-4-phenylisoquinolin-2 (1H)-yl)ethyl]morpholin-4-ium trifluoroacetate,
N-[2-(3-cyano-6-methoxy-1-oxo-4-phenylisoquinolin-2 (1H)-yl)ethyl]propan-2-aminium trifluoroacetate,
N-[2-(3-cyano-6-methoxy-1-oxo-4-phenylisoquinolin-2 (1H)-yl)ethyl]cyclohexanaminium trifluoroacetate,
2-(3-cyano-6-methoxy-1-oxo-4-phenylisoquinolin-2(1H)-yl)-N-(cyclopropylmethyl)-ethanaminium trifluoroacetate,
N-[2-(3-cyano-methoxy-1-oxo-4-phenylisoquinolin-2(1H)-yl)ethyl]-N-methylcyclohexanaminium trifluoroacetate,
2-(3-cyano-6-methoxy-1-oxo-4-phenylisoquinolin-2(1H)-yl)-N-(2-phenylethyl)-ethanaminium trifluoroacetate,
N-[2-(3-cyano-6-methoxy-1-oxo-4-phenylisoquinolin-2 (1H)-yl)ethyl]pyridin-2-aminium trifluoroacetate,
(1R)-N-[2-(3-cyano-6-methoxy-1-oxo-4-phenylisoquinolin-2(1H)-yl)ethyl]-1-phenylethanaminium trifluoroacetate,
6-methoxy-1-oxo-4-phenyl-2-{2-[(pyridin-3-ylmethyl) amino]ethyl}-1,2-dihydroisoquinoline-3-carbonitrile,
2-(2-{[3-(1H-imidazol-1-yl)propyl]amino}ethyl)-6-methoxy-1-oxo-4-phenyl-1,2-dihydroisoquinoline-3-carbonitrile,
N-[2-(3-cyano-6-methoxy-1-oxo-4-phenylisoquinolin-2 (1H)-yl)ethyl]-3-(2-oxopyrrolidin-1-yl)propan-1-aminium trifluoroacetate,
N-[2-(3-cyano-6-methoxy-1-oxo-4-phenylisoquinolin-2 (1H)-yl)ethyl]-3,3-dimethylbutan-1-aminium trifluoroacetate,
2-(acetylamino)-N-[2-(3-cyano-6-methoxy-1-oxo-4-phenylisoquinolin-2(1H)-yl)-ethyl]ethanaminium trifluoroacetate,
6-methoxy-2-methyl-1-oxo-4-pyridin-4-yl-1,2-dihydroisoquinoline-3-carbonitrile,
6-methoxy-2-methyl-1-oxo-4-pyridin-3-yl-1,2-dihydroisoquinoline-3-carbonitrile,
5-methoxy-2-methyl-1-oxo-4-phenyl-1,2-dihydroisoquinoline-3-carbonitrile,
N-(3-cyano-2-methyl-1-oxo-4-phenyl-1,2-dihydroisoquinolin-6-yl)acetamide,
N-3-cyano-2-methyl-1-oxo-4-phenyl-1,2-dihydroisoquinolin-6-yl)methanesulfonamide,
2-methyl-1-oxo-4-phenyl-6-trifluoromethyl)-1,2-dihydroisoquinoline-3-carbonitrile,
2-(2,3-dihydroxypropyl)-6-methoxy-1-oxo-4-phenyl-1,2-dihydroisoquinoline-3-carbonitrile,
7-methoxy-2-methyl-1-oxo-4-phenyl-1,2-dihydroisoquinoline-3-carbonitrile,
4-(3-fluorophenyl)-6-methoxy-2-methyl-1-oxo-1,2-dihydroisoquinoline-3-carbonitrile,
2-methyl-7-nitro-1-oxo-4-phenyl-1,2-dihydroisoquinoline-3-carbonitrile,
2-cyclopropyl-4-(3-fluorophenyl)-6-methoxy-1-oxo-1,2-dihydroisoquinoline-3-carbonitrile,
6-(2-aminoethoxy)-2-methyl-1-oxo-4-phenyl-1,2-dihydroisoquinoline-3-carbonitrile,
[(3-cyano-2-methyl-1-oxo-4-phenyl-1,2-dihydroisoquinolin-6-yl)oxy]acetic acid,
2[(ammoniooxy)methyl]-1-chloro-3-fluorobenzene chloride,
2-allyl-4-(3-fluorophenyl)-6-methoxy-1-oxo-1,2-dihydroisoquinoline-3-carbonitrile,
2-(2,3-dihydroxypropyl)-4-(3-fluorophenyl)-6-methoxy-1-oxo-1,2-dihydroisoquinoline-3-carbonitrile,
4-(3-fluorophenyl)-6-methoxy-2-(2-morpholin-4-ylethyl)-1-oxo-1,2-dihydroisoquinoline-3-carbonitrile,
4-(3-fluorophenyl)-6-methoxy-2-{2-[(2-methoxyethyl)(methyl)-amino]ethyl}-1-oxo-1,2-dihydroisoquinoline-3-carbonitrile,
2,5-dimethyl-1-oxo-4-phenyl-1,2-dihydroisoquinoline-3-carbonitrile,
4-(3-fluorophenyl)-2-{2-[(2-hydroxyethyl)(methyl)amino] ethyl}-6-methoxy-1-oxo-1,2-dihydroisoquinoline-3-carbonitrile,
4-(3-fluorophenyl)-6-methoxy-2-{2-[(2-methoxyethyl) amino]ethyl}-1-oxo-1,2-dihydroisoquinoline-3-carbonitrile,
2-methyl-1-oxo-4-phenyl-6(pyridin-2-ylmethoxy)-1,2-dihydroisoquinoline-3-carbonitrile,
2-methyl-6-(2-morpholin-4-ylethoxy)-1-oxo-4-phenyl-1,2-dihydroisoquinoline-3-carbonitrile,
2-methyl-1-oxo-4-phenyl-6-(2-piperidin-1-ylethoxy)-1,2-dihydroisoquinoline-3-carbonitrile,
6-acetyl-2-methyl-1-oxo-4-phenyl-1,2-dihydroisoquinoline-3-carbonitrile,
6-(1-hydroxyethyl)-2-methyl-1-oxo-4-phenyl-1,2-dihydroisoquinoline-3-carbonitrile,
2-methyl-1-oxo-4-phenyl-6-(piperidin-4-yloxy)-1,2-dihydroisoquinoline-3-carbonitrile,
6-(2,2-difluoro-2-pyridin-2-ylethoxy)-2-methyl-1-oxo-4-phenyl-1,2-dihydroisoquinoline-3-carbonitrile,
2-cyclopropyl-4-(3-fluorophenyl)-6-hydroxy-1-oxo-1,2-dihydroisoquinoline-3-carbonitrile,
2-methyl-1-oxo-4-phenyl-6-(pyrrolidin-3-yloxy)-1,2-dihydroisoquinoline-3-carbonitrile, 4-(3-fluorophenyl)-6-methoxy-1-oxo-2-(2,2,2-trifluoroethyl)-1,2-dihydroisoquinoline-3-carbonitrile,
4-(4-fluorophenyl)-6-methoxy-2-methyl-1-oxo-1,2-dihydroisoquinoline-3-carbonitrile,
5,7-dibromo-4-(3-fluorophenyl)-6-hydroxy-2-methyl-1-oxo-1,2-dihydroisoquinoline-3-carbonitrile,
5,7-dibromo-2-cyclopropyl-4-(3-fluorophenyl)-6-hydroxy-1-oxo-1,2-dihydroisoquinoline-3-carbonitrile,
5-bromo-2-cyclopropyl-4-(3-fluorophenyl)-6-hydroxy-1-oxo-1,2-dihydroisoquinoline-3-carbonitrile,
2-cyclopropyl-4-(3-fluorophenyl)-1-oxo-6-(2,2,2-trifluoroethoxy)-1,2-dihydroisoquinoline-3-carbonitrile,
2-methyl-6-(1-morpholin-4-ylethyl)-1-oxo-4-phenyl-1,2-dihydroisoquinoline-3-carbonitrile,
2-methyl-6-[(1-oxidopyridin-2-yl)methoxy]-1-oxo-4-phenyl-1,2-dihydroisoquinoline-3-carbonitrile,
6-(allyloxy)-2-cyclopropyl-4-(3-fluorophenyl)-1-oxo-1,2-dihydroisoquinoline-3-carbonitrile,
2-cyclopropyl-4-(3-fluorophenyl)-6-(2-methoxyethoxy)-1-oxo-1,2-dihydroisoquinoline-3-carbonitrile,
6-methoxy-2-methyl-1-oxo-4-[4-trifluoromethyl)phenyl]-1,2-dihydroisoquinoline-3-carbonitrile,
2-(2,3-dihydroxypropyl)-4-(3-fluorophenyl)-6-methoxy-1-oxo-1,2-dihydroisoquinoline-3-carbonitrile,
2-(2,3-dihydroxypropyl)-4-(3-fluorophenyl)-6-methoxy-1-oxo-1,2-dihydroisoquinoline-3-carbonitrile,
2-cyclopropyl-6-(2,3-dihydroxypropoxy)-4-(3-fluorophenyl)-1-oxo-1,2-dihydroisoquinoline-3-carbonitrile,
2-cyclopropyl-6-ethoxy-4-(3-fluorophenyl)-1-oxo-1,2-dihydroisoquinoline-3-carbonitrile,
2-allyl-6-methoxy-1-oxo-4-phenyl-1,2-dihydroisoquinoline-3-carbonitrile,
1-(3-cyano-2-methyl-1-oxo-4-phenyl-1,2-dihydroisoquinolin-6-yl)ethanaminium trifluoroacetate,
5-bromo-6-methoxy-2-methyl-1-oxo-4-phenyl-1,2-dihydroisoquinoline-3-carbonitrile,
7-bromo-6-methoxy-2-methyl-1-oxo-4-phenyl-1,2-dihydroisoquinoline-3-carbonitrile,
2-methyl-1-oxo-4-phenyl-6-thien-2-yl-1,2-dihydroisoquinoline-3-carbonitrile,
2-cyclopropyl-6-(fluoromethoxy)-4-(3-fluorophenyl)-1-oxo-1,2-dihydroisoquinoline-3-carbonitrile,
2-methyl-1-oxo-4-phenyl-6-thien-3-yl-1,2-dihydroisoquinoline-3-carbonitrile,
4-(3-fluorophenyl)-2-(2-hydroxyethyl)-6-methoxy-1-oxo-1,2-dihydroisoquinoline-3-carbonitrile,
4-(3-fluorophenyl)-2-{2-[(2-hydroxyethyl)amino]ethyl}-6-methoxy-1-oxo-1,2-dihydroisoquinoline-3-carbonitrile,
2-[(2s)-2,3-dihydoxypropyl]-6-methoxy-1-oxo-4-phenyl-1,2-dihydroisoquinoline-3-carbonitrile,
2-[(2r)-2,3-dihydroxypropyl]-6-methoxy-1-oxo-4-phenyl-1,2-dihydroisoquinoline-3-carbonitrile,
4-(2-fluorophenyl)-6-methoxy-2-methyl-1-oxo-1,2-dihydroisoquinoline-3-carbonitrile,
2-allyl-4-(2-fluorophenyl)-6-methoxy-1-oxo-1,2-dihydroisoquinoline-3-carbonitrile,
2-cyclopropyl-4-(3-fluorophenyl)-1-oxo-6-propoxy-1,2-dihydroisoquinoline-3-carbonitrile,
6-(benzyloxy)-2-cyclopropyl-4-(3-fluorophenyl)-1-oxo-1,2-dihydroisoquinoline-3-carbonitrile,
4-(3-fluorophenyl)-2-(3-hydoxypropyl)-6-methoxy-1-oxo-1,2-dihydroisoquinoline-3-carbonitrile,
2-[3-(dimethylamino)-2-hydroxypropyl]-6-methoxy-1-oxo-4-phenyl-1,2-dihydroisoquinoline-3-carbonitrile,
6-methoxy-2-methyl-4-(4-nitrophenoxy)-1-oxo-1,2-dihydroisoquinoline-3-carbonitrile,
6-methoxy-4-(4-methoxyphenyl)-2-methyl-1-oxo-1,2-dihydroisoquinoline-3-carbonitrile,
2-(2-amino-3-hydroxypropyl)-6-methoxy-1-oxo-4-phenyl-1,2-dihydroisoquinoline-3-carbonitrile,
2-(2,3-dihydroxypropyl)-4-(2-fluorophenyl)-6-methoxy-1-oxo-1,2-dihydroisoquinoline-3-carbonitrile,
6-methoxy-2-methyl-1-oxo-4-[3-(trifluoromethyl)phenyl]-1,2-dihydroisoquinoline-3-carbonitrile,
4-[3,5-bis(trifluoromethyl)phenyl]-6-methoxy-2-methyl-1-oxo-1,2-dihydroisoquinoline-3-carbonitrile,
6-[2-(benzyloxy)ethoxy]-2-cyclopropyl-4-(3-fluorophenyl)-1-oxo-1,2-dihydoisoquinoline-3-carbonitrile,
2-[2-(dimethylamino)-3-hydroxypropyl]-6-methoxy-1-oxo4-phenyl-1,2-dihydroisoquinoline-3-carbonitrile,
2-[3-(dimethylamino)-2-hydoxypropyl]-4-(3-fluorophenyl)-6-methoxy-1-oxo-1,2-dihydroisoquinoline-3-carbonitrile,
4-2-fluorophenyl)-6-methoxy-1-oxo-1,2-dihydroisoquinoline-3-carbonitrile,
2-(2-hydroxy-3-isopropoxypropyl)-6-methoxy-1-oxo-4-phenyl-1,2-dihydroisoquinoline-3-carbonitrile,
4-(3-aminophenyl)-6-methoxy-2-methyl-1-oxo-1,2-dihydroisoquinoline-3-carbonitrile,
6-methoxy-2-methyl-4-(3-methylphenyl)-1-oxo-1,2-dihydroisoquinoline-3-carbonitrile,
4-3,5-dichlorophenyl)-6-methoxy-2-methyl-1-oxo-1,2-dihydroisoquinoline-3-carbonitrile,
4-3-fluorophenyl)-methoxy-1-oxo-1,2-dihydroisoquinoline-3-carbonitrile,
2-cyclopropyl-4-(3-fluorophenyl)-1-oxo-6-(tetrahydrofuran-2-ylmethoxy)-1,2-dihydroisoquinoline-3-carbonitrile,
2-cyclopropyl-6-(cyclopropylmethoxy)-4-(3-fluorophenyl)-1-oxo-1,2-dihydroisoquinoline-3-carbonitrile,
2-cyclopropyl-6-(2-ethoxyethoxy)-4-(3-fluorophenyl)-1-oxo-1,2-dihydroisoquinoline-3-carbonitrile,
6-[3-(benzyloxy)propoxy]-2-cyclopropyl-4-(3-fluorophenyl)-1-oxo-1,2-dihydroisoquinoline-3-carbonitrile,
2-cyclopropyl-6-(2,3-dihydro-1,4-benzodioxin-2-ylmethoxy)-4-(3-fluorophenyl)-1-oxo-1,2-dihydroisoquinoline-3-carbonitrile,
2-cyclopropyl-4-3-fluorophenyl)-1-oxo-6-(tetrahydro-2H-pyran-2-ylmethoxy)-1,2-dihydroisoquinoline-3-carbonitrile,
ethyl{[3-cyano-2-cyclopropyl-4-(3-fluorophenyl)-1-oxo-1,2-dihydroisoquinolin-6-yl]oxy}acetate,
2-cyclopropyl-4-3-fluorophenyl)-6-(2-hydroxyethoxy)-1-oxo-1,2-dihydroisoquinoline-3-carbonitrile,
4-(4-aminophenoxy)-6-methoxy-2-methyl-1-oxo-1,2-dihydroisoquinoline-3-carbonitrile,
6-methoxy-4-(3-methoxyphenyl)-2-methyl-1-oxo-1,2-dihydroisoquinoline-3-carbonitrile,
6-methoxy-2-methyl-1-oxo-4-phenoxy-1,2-dihydroisoquinoline-3-carbonitrile,
2-cyclopropyl-4-(3-fluorophenyl)-6-(3-hydroxypropoxy)-1-oxo-1,2-dihydroisoquinoline-3-carbonitrile,
2-cyclopropyl-6-(difluoromethoxy)-4-(3-fluorophenyl)-1-oxo-1,2-dihydroisoquinoline-3-carbonitrile,
2-methyl-6-morpholin-4-yl-1-oxo-4-phenyl-1,2-dihydroisoquinoline-3-carbonitrile,
2-methyl-1-oxo-4-phenyl-6-pyridin-4-yl-1,2-dihydroisoquinoline-3-carbonitrile,
2-methyl-1-oxo4-phenyl-6-pyridin-3-yl-1,2-dihydroisoquinoline-3-carbonitrile,
2-{[3-cyano-2-cyclopropyl-4-(3-fluorophenyl)-1-oxo-1,2-dihydroisoquinolin-6-yl]oxy}-N,N-dimethylacetamide, 2-cyclopropyl-4-(3-fluorophenyl)-6-(2-morpholin-4-yl-2-oxoethoxy)-1-oxo-1,2-dihydroisoquinoline-3-carbonitrile,
4-(4-cyanophenyl)-6-methoxy-2-methyl-1-oxo-1,2-dihydroisoquinoline-3-carbonitrile,
4-(3-cyanophenyl)-6-methoxy-2-methyl-1-oxo-1,2-dihydroisoquinoline-3-carbonitrile,
4-(1,3-benzodioxol-5-yl)-6-methoxy-2-methyl-1-oxo-1,2-dihydroisoquinoline-3-carbonitrile,
2-methyl-6-(4-methylpiperazin-1-yl)-1-oxo-4-phenyl-1,2-dihydroisoquinoline-3-carbonitrile,
2-methyl-1-oxo-4-phenyl-6-piperidin-1-yl-1,2-dihydroisoquinoline-3-carbonitrile,
6-methoxy-2-methyl-1-oxo-4-(1h-pyrazol-3-yl)-1,2-dihydroisoquinoline-3-carbonitrile,
4-[4-(hydroxymethyl)phenyl]-6-methoxy-2-methyl-1-oxo-1,2-dihydroisoquinoline-3-carbonitrile,
ethyl [3-cyano-4-(3-fluorophenyl)-6-methoxy-1-oxoisoquinolin-2(1H)-yl]acetate
2-[2-hydroxy-3-(1H-imidazol-1-yl)propyl]-6-methoxy-1-oxo-4-phenyl-1,2-dihydroisoquinoline-3-carbonitrile,
6-(3-furyl)-2-methyl-1-oxo-4-phenyl-1,2-dihydroisoquinoline-3-carbonitrile,
2-methyl-1-oxo-4-phenyl-6-thiomorpholin-4-yl-1,2-dihydroisoquinoline-3-carbonitrile,
2-cyclopropyl-4-(3-fluorophenyl)-6-[(3-nitropyridin-2-yl)oxy]-1-oxo-1,2-dihydroisoquinoline-3-carbonitrile,
ethyl 4-{[3-cyano-2-cyclopropyl-4-3-fluorophenyl)-1-oxo-1,2-dihydroisoquinolin-6-yl]oxy}butanoate,
ethyl 5-{[3-cyano-2-cyclopropyl-4-(3-fluorophenyl)-1-oxo-1,2-dihydroisoquinolin-6-yl]oxy}pentanoate,
2-cyclopropyl-4-(3-fluorophenyl)-1-oxo-6-(vinyloxy)-1,2-dihydroisoquinoline-3-carbonitrile,
2-methyl-1-oxo-4-phenyl-6-pyridin-2-yl-1,2-dihydroisoquinoline-3-carbonitrile,
2-(3-ethoxy-2-hydroxypropyl)-6-methoxy-1-oxo-4-phenyl-1,2-dihydroisoquinoline-3-carbonitrile,
2-(2-hydroxy-3-methoxypropyl)-6-methoxy-1-oxo-4-phenyl-1,2-dihydroisoquinoline-3-carbonitrile,
2-(2-hydroxybutyl)-6-methoxy-1-oxo-4-phenyl-1,2-dihydroisoquinoline-3-carbonitrile,
2-(2-hydroxypropyl)-6-methoxy-1-oxo-4-phenyl-1,2-dihydroisoquinoline-3-carbonitrile,
6-[(3-aminopyridin-2-yl)oxy]-2-cyclopropyl-4-(3-fluorophenyl)-1-oxo-1,2-dihydroisoquinoline-3-carbonitrile,
methyl 3-(3-cyano-6-methoxy-2-methyl-1-oxo-1,2-dihydroisoquinolin-4-yl)benzoate,
methyl 4-(3-cyano-6-methoxy-2-methyl-1-oxo-1,2-dihydroisoquinolin-4-yl)benzoate,
2-cyclopropyl-6-[4-1,3-dioxo-1,3-dihydro-2H-isoindol-2-yl)butoxy]-(3-fluorophenyl)-1-oxo-1,2-dihydroisoquinoline-3-carbonitrile,
2-cyclopropyl-6-{[5-(1,3-dioxo-1,3-dihydro-2H-isoindol-2-yl)pentyl]oxy}-4-(3-fluorophenyl)-1-oxo-1,2-dihydroisoquinoline-3-carbonitrile,
2-cyclopropyl-6-{[6-(1,3-dioxo-1,3-dihydro-2H-isoindol-2-yl)hexyl]oxy}-4-(3-fluorophenyl)-1-oxo-1,2-dihydroisoquinoline-3-carbonitrile,
2-{[3-cyano-2-cyclopropyl-4-(3-fluorophenyl)-1-oxo-1,2-dihydroisoquinolin-6-yl]oxy}-N,N-dimethylethanaminium trifluoroacetate,
3-{[3-cyano-2-cyclopropyl-4-(3-fluorophenyl)-1-oxo-1,2-dihydroisoquinolin-6-yl]oxy}-N,N-dimethylpropan-1-aminium trifluoroacetate,
6-{[3-cyano-2-cyclopropyl-4-(3-fluorophenyl)-1-oxo-1,2-dihydroisoquinolin-6-yl]oxy}hexan-1-aminium trifluoroacetate,
4-{[3-cyano-2-cyclopropyl-4-(3-fluorophenyl)-1-oxo-1,2-dihydroisoquinolin-6-yl]oxy}butanoic acid,
4-ethynyl-6-methoxy-2-methyl-1-oxo-1,2-dihydroisoquinoline-3-carbonitrile,
5-{[3-cyano-2-cyclopropyl-4-(3-fluorophenyl)-1-oxo-1,2-dihydroisoquinolin-6-yl]oxy}pentanoic acid,
4-{[3-cyano-2-cyclopropyl-4-(3-fluorophenyl)-1-oxo-1,2-dihydroisoquinolin-6-yl]oxy}butan-1-aminium trifluoroacetate,
5-{[3-cyano-2-cyclopropyl-4-(3-fluorophenyl)-1-oxo-1,2-dihydroisoquinolin-6-yl]oxy}pentan-1-aminium trifluoroacetate,
6-(4-hydroxypiperidin-1-yl)-2-methyl-1-oxo-4-phenyl-1,2-dihydroisoquinoline-3-carbonitrile,
2-allyl-4-(3-chlorophenyl)-6-methoxy-1-oxo-1,2-dihydroisoquinoline-3-carbonitrile,
4-(3-fluorophenyl)-6-methoxy-1-oxo-2-[2-(3-oxo-4-phenylpiperazin-1-yl)ethyl]-1,2-dihydroisoquinoline-3-carbonitrile,
4-({2-[3-cyano-4-(3-fluorophenyl)-6-methoxy-1-oxoisoquinolin-2(1h)-yl]ethyl}-amino)benzoic acid,
3-({2-[3-cyano-4-(3-fluorophenyl)-6-methoxy-1-oxoisoquinolin-2(1H)-yl]ethyl}-amino)benzoic acid,
2-({2-[3-cyano-4-(3-fluorophenyl)-6-methoxy-1-oxoisoquinolin-2(1H)-yl]ethyl}-amino)benzoic acid,
4-(3-chlorophenyl)-2-2,3-dihydroxypropyl)-6-methoxy-1-oxo-1,2-dihydroisoquinoline-3-carbonitrile,
2-cyclopropyl-6-(cyclopropyloxy)-4-(3-fluorophenyl)-1-oxo-1,2-dihydroisoquinoline-3-carbonitrile,
2-cyclopropyl-4-(3-fluorophenyl)-6-[(5-morpholin-4-yl-5-oxopentyl)oxy]-1-oxo-1,2-dihydroisoquinoline-3-carbonitrile,
2-cyclopropyl-4-(3-fluorophenyl)-6-(4-morpholin-4-yl-4-oxobutoxy)-1-oxo-1,2-dihydroisoquinoline-3-carbonitrile,
5-{[3-cyano-2-cyclopropyl-4-(3-fluorophenyl)-1-oxo-1,2-dihydroisoquinolin-6-yl]oxy}pentyl acetate,
2-cyclopropyl-4-(3-fluorophenyl)-6-(4-hydroxybutoxy)-1-oxo-1,2-dihydroisoquiaoline-3-carbonitrile,
6-(cyanomethoxy)-2-cyclopropyl-4-(3-fluorophenyl)-1-oxo-1,2-dihydroisoquinoline-3-carbonitrile,
2-cyclopropyl-4-(3-fluorophenyl)-6-[(5-hydroxypentyl)oxy]-1-oxo-1,2-dihydroisoquinoline-3-carbonitrile,
2-(2,3-hydroxypropyl)-6-methoxy-1-oxo-4-[3-trifluoromethyl)phenyl]-1,2-dihydroisoquinoline-3-carbonitrile,
3-cyano-2-cyclopropyl-4-3-fluorophenyl)-1-oxo-1,2-dihydroisoquinolin-6-yl morpholine-4-carboxylate,
2-{3-hydroxy-2-[(pyridin-3-ylmethyl)amino]propyl}-6-methoxy-1-oxo-4-phenyl-1,2-dihydroisoquinoline-3-carbonitrile,
3-cyano-2-cyclopropyl-(3-fluorophenyl)-1-oxo-1,2-dihydroisoquinolin-6-yl acetate,
4-(3-fluorophenyl)-2-{2-[(2-hydroxy-2,3-dihydro-1H-inden-1-yl)amino]ethyl}-6-methoxy-1-oxo-1,2-dihydroisoquinoline-3-carbontritrile,
methyl (2S)-({2-[3-cyano-4-(3-fluorophenyl)-6-methoxy-1-oxoisoquinolin-2(1H)-yl]ethyl}-amino)(phenyl)ethanoate,
methyl (2R)-({2-[3-cyano-4-3-fluorophenyl)-6-methoxy-1-oxoisoquinolin-2(1h)-yl]ethyl}-amino)(phenyl)ethanoate,
2-(2-hydroxy-2-methylpropyl)-6-methoxy-1-oxo-4-phenyl-1,2-dihydroisoquinoline-3-carbonitrile,
3-cyano-2-cyclopropyl-4-(3-fluorophenyl)-1-oxo-1,2-dihydroisoquinolin-6-yl benzoate,
3-cyano-2-cyclopropyl-4-(3-fluorophenyl)-1-oxo-1,2-dihydroisoquinolin-yl methanesulfonate, 6-methoxy-2-methyl-1-oxo-4-phenylethynyl)-1,2-dihydroisoquinoline-3-carbonitrile,
2-{[3-cyano-2-cyclopropyl-4-(3-fluorophenyl)-1-oxo-1,2-dihydroisoquinolin-6-yl]oxy}ethyl morpholine-4-carboxylate,
2-allyl-1-oxo-4-phenyl-6-thien-3-yl-1,2-dihydroisoquinoline-3-carbonitrile,
2-allyl-6-(3-furyl)-1-oxo-4-phenyl-1,2-dihydroisoquinoline-3-carbonitrile,
5-{[3-cyano-2-cyclopropyl-4-(3-fluorophenyl)-1-oxo-1,2-dihydroisoquinolin-6-yl]oxy}pentyl morpholine-4-carboxylate,
3-{[-cyano-2-cyclopropyl-4-(3-fluorophenyl)-1-oxo-1,2-dihydroisoquinolin-6-yl]oxy}propyl morpholine-4-carboxylate,
4-(3-fluorophenyl)-2-(2-{[(1R)-2-hydroxy-1-phenylethyl]amino}-ethyl)-6-methoxy-1-oxo-1,2-dihydroisoquinoline-3-carbonitrile,
ethyl ({2-[3-cyano-4-(3-fluorophenyl)-6-methoxy-1-oxoisoquinolin-2(1H)-yl]ethyl}-amino)(phenyl)acetate,
2-(2,3-dihydroxypropyl)-4-(3-fluorophenyl)-1-oxo-6-thien-3-yl-1,2-dihydroisoquinoline-3-carbonitrile,
6-(1-benzothien-3-yl)-2-(2,3-dihydroxypropyl)-4-(3-fluorophenyl)-1-oxo-1,2-dihydroisoquinoline-3-carbonitrile,
methyl [3-cyano-4-(3-fluorophenyl)-6-methoxy-1-oxoisoquinolin-2(1H)-yl]acetate,
2-(2,3-dihydroxypropyl)-4-(3-fluorophenyl)-6-(3-furyl)-1-oxo-1,2-dihydroisoquinoline-3-carbonitrile,
2-(2,3-dihydroxypropyl)-4-(3-fluorophenyl)-6-[2-(hydroxymethyl)thien-3-yl]-1-oxo-1,2-dihydroisoquinoline-3-carbonitrile,
tert-butyl {[3-cyano-2-cyclopropyl-4-(3-fluorophenyl)-1-oxo-1,2-dihydroisoquinolin-6-yl]oxy}acetate,
[3-cyano-4-(3-fluorophenyl)-6-methoxy-1-oxoisoquinolin-2(1H)-yl]acetic acid, {[3-cyano-2-cyclopropyl-4-(3-fluorophenyl)-1-oxo-1,2-dihydroisoquinolin-6-yl]oxy}acetic acid,
({2-[3-cyano-4-(3-fluorophenyl)-6-methoxy-1-oxoisoquinolin-2(1H)-yl]ethyl}amino)-(phenyl)acetic acid,
2-[3-hydroxy-2-(1h-1,2,3-triazol-1-yl)propyl]-6-methoxy-1-oxo-4-phenyl-1,2-dihydroisoquinoline-3-carbonitrile,
methyl ({2-[3-cyano-4-(3-fluorophenyl)-6-methoxy-1-oxoisoquinolin-2(1H)-yl]ethyl}-amino)(pyridin-3-yl)acetate,
2-cyclopropyl-4-(3-fluorophenyl)-1-oxo-6-(2-oxo-2-pyrrolidin-1-ylethoxy)-1,2-dihydroisoquinoline-3-carbonitrile,
methyl 2-[3-cyano-4-(3-fluorophenyl)-6-methoxy-1-oxoisoquinolin-2(1H)-yl]propanoate,
2-cyclopropyl-4-(3-fluorophenyl)-1-oxo-6-(2-oxo-2-piperidin-1-ylethoxy)-1,2-dihydroisoquinoline-3-carbonitrile,
N-benzyl-2-{[3-cyano-2-cyclopropyl-4-(3-fluorophenyl)-1-oxo-1,2-dihydroisoquinolin-6-yl]oxy}-N-methylacetamide,
2-{[3-cyano-2-cyclopropyl-4-(3-fluorophenyl)-1-oxo-1,2-dihydroisoquinolin-6-yl]oxy}-N-methoxy-N-methylacetamide,
2-{[3-cyano-2-cyclopropyl-4-(3-fluorophenyl)-1-oxo-1,2-dihydroisoquinolin-6-yl]oxy}-N-(2-methoxyethyl)acetamide,
2-{[3-cyano-2-cyclopropyl-4-(3-fluorophenyl)-1-oxo-1,2-dihydroisoquinolin-6-yl]oxy}-N-(3-methoxypropyl)acetamide,
2-cyclopropyl-4-(3-fluorophenyl)-1-oxo-6-[2-oxo-2-(3-oxopiperazin-1-yl)ethoxy]-1,2-dihydroisoquinoline-3-carbonitrile,
N-benzyl-2-{[3-cyano-2-cyclopropyl-4-(3-fluorophenyl)-1-oxo-1,2-dihydroisoquinolin-6-yl]oxy}acetamide,
6-2-azetidin-1-yl-2-oxoethoxy)-2-cyclopropyl-4-(3-fluorophenyl)-1-oxo-1,2-dihydroisoquinoline-3-carbonitrile,
2-{[3-cyano-2-cyclopropyl-4-(3-fluorophenyl)-1-oxo-1,2-dihydroisoquinolin-6-yl]oxy}-N-(2-methoxyethyl)-N-methylacetamide,
N,N-dibenzyl-2-{[3-cyano-2-cyclopropyl-4-(3-fluorophenyl)-1-oxo-1,2-dihydroisoquinolin-6-yl]oxy}acetamide,
2-allyl-6-methoxy-1-oxo-4-pyridin-2-yl-1,2-dihydroisoquinoline-3-carbonitrile,
6-methoxy-2-methyl-1-oxo4-(1h-1,2,3-triazol-5-yl)-1,2-dihydroisoquinoline-3-carbonitrile,
methyl {[(3-cyano-6-methoxy-2-methyl-1-oxo-1,2-dihydroisoquinolin-4-yl)oxy]sulfonyl}carbamate,
7-cyclopropyl-9-(3-fluorophenyl)-2-methyl-6-oxo-1,2,6,7-tetrahydrofuro[3,2-f]-isoquinoline-8-carbonitrile,
5-allyl-2-cyclopropyl-4-(3-fluorophenyl)-6-methoxy-1-oxo-1,2-dihydroisoquinoline-3-carbonitrile,
2-cyclopropyl-5-(2,3-dihydroxypropyl)-4-(3-fluorophenyl)-6-methoxy-1-oxo-1,2-dihydroisoquinoline-3-carbonitrile,
2-(2,3-dihydroxypropyl)-6-methoxy-1-oxo-4-pyridin-2-yl-1,2-dihydroisoquinoline-3-carbonitrile,
2-(2,3-dihydroxypropyl)-6-methoxy-1-oxo-4-pyridin-2-yl-1,2-dihydroisoquinoline-3-carbonitrile,
2-allyl-4-(3-fluorophenyl)-6-(6-methylpyridin-2-yl)-1-oxo-1,2-dihydroisoquinoline-3-carbonitrile,
2-{[3-cyano-4-(3-fluorophenyl)-6-methoxy-1-oxoisoquinolin-2(1h)-yl]methyl}-1h-benzimidazol-1-ium chloride,
4-(3-fluorophenyl)-6-methoxy-1-oxo-2-{2-[(pyridin-2-ylmethyl)amino]ethyl}-1,2-dihydroisoquinoline-3-carbonitrile,
2-allyl-4-(3-fluorophenyl)-1-oxo-6-(1H-pyrazol-4-yl)-1,2-dihydroisoquinoline-3-carbonitrile,
2-[2-allyl-3-cyano-4-(3-fluorophenyl)-1-oxo-1,2-dihydroisoquinolin-6-yl]-4-methylpyridinium trifluoroacetate,
2-[3-cyano-2-(2,3-dihydroxypropyl)-4-(3-fluorophenyl)-1-oxo-1,2-dihydroisoquinolin-6-yl]-6-methylpyridinium trifluoroacetate,
4-(3-chlorophenyl)-2-{[(4S)-2,2-diethyl-1,3-dioxolan-4-yl]methyl}-6-methoxy-1-oxo-1,2-dihydroisoquinoline-3-carbonitrile,
2-allyl-6-methoxy-1-oxo-4-pyridin-3-yl-1,2-dihydroisoquinoline-3-carbonitrile,
2-(2,3-dihydroxypropyl)-6-methoxy-4-(1-oxidopyridin-2-yl)-1-oxo-1,2-dihydroisoquinoline-3-carbonitrile, and
4-(3-chlorophenyl)-2-[(2S)-2,3-dihydroxypropyl]-6-methoxy-1-oxo-1,2-dihydroisoquinoline-3-carbonitrile.

The above-listed compounds are active in one or more of the assays for Kv1.5 described below.

Another embodiment of the invention is a method of treating or preventing a condition in a mammal, the treatment or prevention of which is effected or facilitated by $K_v1.5$ inhibition, which comprises administering an amount of a compound of Formula I that is effective at inhibiting $K_v1.5$.

A preferred embodiment is a method of treating or preventing cardiac arrhythmias, e.g. atrial fibrillation, atrial flutter, atrial arrhythmia, and supraventricular tachycardia, in a mammal, which comprises administering a therapeutically effective amount of a compound of Formula I.

Another preferred embodiment is a method of preventing thromboembolic events, such as stroke.

Another preferred embodiment is a method of preventing congestive heart failure.

Another preferred embodiment is a method of treating or preventing immunodepression or a disorder involving immunodepression, such as AIDS, cancer, senile dementia, trauma (including wound healing, surgery and shock) chronic bacterial infection, certain central nervous system disorders, and conditions including resistance by transplantation of organs or tissue, graft-versus-host diseases brought about by medulla ossium transplantation. Within this embodiment is a method for treating or preventing immunodepression by administering a compound of the invention with an immunosuppresant compound.

Another preferred embodiment is a method of treating or preventing gliomas including those of lower and higher malignancy, preferably those of higher malignancy.

Another preferred embodiment is a method for inducing in a patient having atrial fibrillation, a condition of normal sinus rhythm, in which the induced rhythm corresponds to the rhythm that would be considered normal for an individual sharing with the patient similar size and age characteristics, which comprises treating the patient with a compound of the invention.

Another preferred embodiment is a method for treating tachycardia, (i.e., rapid heart rate e.g. 100 beats per minute) in a patient which comprises treating the patient with an anti-tachycardia device (e.g. a defibrillator or a pacemaker) in combination with a compound of Claim 1.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

The compounds of the present invention may have asymmetric centers or asymmetric axes, and this invention includes all of the optical isomers and mixtures thereof. Unless specifically mentioned otherwise, reference to one isomer applies to both isomers.

In addition compounds with carbon-carbon double bonds may occur in Z- and E-forms with all isomeric forms of the compounds being included in the present invention.

Except where noted, the number of carbon atoms in a defined substituent is represented by use of a subscript number follwing the letter "C", e.g. $C_2$. Definitions of substituents containing a range of carbon atoms, e.g. between 1 and 6 carbon atoms, can be represented by "$C_{1-6}$" or "$C_1$-$C_6$", such that, for example, "$C_{1-6}$ alkyl" and "$C_1$-$C_6$ alkyl" have equivalent meanings.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkoxy" represents a linear or branched alkyl group of indicated number of carbon atoms attached through an oxygen bridge.

The term "alkenyl" includes both branched and straight chain unsaturated hydrocarbon groups containing at least two carbon atoms joined by a double bond. The alkene ethylene is represented, for example, by "$CH_2CH_2$" or alternatively, by "$H_2C=CH_2$". "$C_{2-5}$ alkenyl" (or "$C_2$-$C_5$ alkenyl") for example, means linear or branched chain alkenyl groups having from 2 to 5 carbon atoms and includes all of the pentenyl isomers as well as 1-butenyl, 2-butenyl, 3-butenyl, 1-propenyl, 2-propenyl, and ethenyl (or ethylenyl). Similar terms such as "$C_{2-3}$ alkenyl" have an analogous meaning.

The term "alkynyl" includes both branched and straight chain unsaturated hydrocarbon groups containing at least two carbon atoms joined by a triple bond. The alkyne acetlyene is represented, for example, by "CHCH" or alternatively, by "HC≡CH". "$C_{2-5}$ alkynyl" (or "$C_2$-$C_5$ alkynyl") for example, means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-3}$ alkynyl" have an analogous meaning.

Unless otherwise noted, alkyl, alkenyl and alkynyl groups are unsubstituted or substituted with 1 to 3 substituents on each carbon atom, with halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond. Similarly, when an integer defining the presence of a certain number of atoms in a group is equal to zero, it means that the atoms adjacent thereto are connected directly by a bond. For example, in the structure

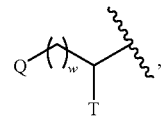

wherein w is an integer equal to zero, 1 or 2, the structure is

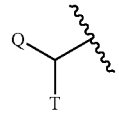

when w is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

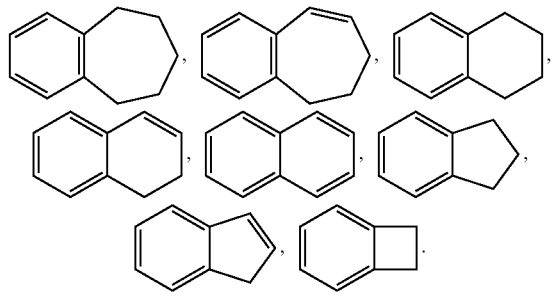

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. The heterocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results.

As used herein, references to substituted cycloalkyl, substituted aryl and substituted heterocyclic groups are intended to include the cyclic group containing from 1 to 4 substituents in addition to the point of attachment to the rest of the compound. Preferably, the substituents are selected from the group which includes, but is not limited to, halogen, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)S(O)$_{0-2}$—, ($C_0$-$C_6$ alkyl)S(O)$_{0-2}$—, aryl-S(O)$_{0-2}$—, ($C_1$-$C_6$ alkyl)-, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—($C_1$-$C_6$ alkyl)OC(O)—, HOC(O)—, ($C_1$-$C_6$alkyl)O($C_1$-$C_6$ alkyl)-, HO($C_1$-$C_6$ alkyl), ($C_1$-$C_6$ alkyl)C(O)($C_0$-$C_6$ alkyl)-, ($C_0$-$C_6$ alkyl)OC(O)NH—, aryl, $C_1$-$C_6$alkoxyaryl, aralkyl, heteroaryl, heterocyclylalkyl, halo-aryl, —OC(O)NH$C_{1-6}$alkyl, halo-aralyl, halo-heterocycle, halo-heterocyclylalkyl, cyano-aryl, cyano-aralkyl, cyano-heterocycle and cyano-heterocyclylalkyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e., 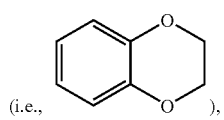), imidazo(2,1-b)(1,3)thiazole, (i.e., 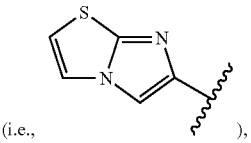), and benzo-1,3-dioxolyl (i.e., 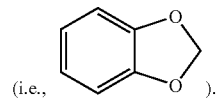).

In certain contexts herein,

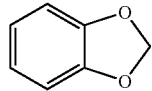

is alternatively referred to as phenyl having as a substituent methylenedioxy attached to two adjacent carbon atoms.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

In compounds of the invention having pyridyl N-oxide moieties, the pyridyl-N-oxide portion is structurally depicted using conventional representations such as

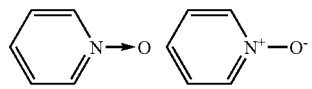

which have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

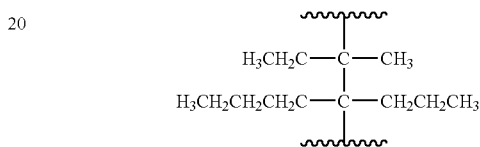

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

Methods for preparing the compounds of this invention are illustrated in the following schemes, in which variable $R^1$ is as defined above, and $R^aO$— is a substituent selected from the group consisting of —$OR^{43}$, —$O(CR^eR^f)_{2-6}S(O)_{0-2}R^{60}$, —$O(CR^eR^f)_{1-6}R^{43}$, —$O(CR^eR^f)_{2-6}O(CR^gR^h)_{0-6}$-aryl, —$O(CR^eR^f)_{2-6}O(CR^gR^h)_{0-6}C_{1-6}$alkyl, —$O(CR^eR^f)_{0-6}C(O)OC_{1-6}$alkyl,
—$O(CR^eR^f)_{2-6}OC(O)C_{1-6}$alkyl, —$O(CR^eR^f)_{0-6}C(O)R^{82}$, —$O(CR^eR^f)_{2-6}OC(O)R^{82}$,
—$O(CR^eR^f)_{0-6}C(O)N(R^{43})(CR^gR^h)$-aryl, —$O(CR^eR^f)_{0-6}C(O)N(R^{43}R^{44})$,
—$O(CR^eR^f)_{0-6}C(O)N(R^{43})(OR^{44})$, as defined above. Other synthetic protocols will be readily apparent to those skilled in the art.

Methods for preparing the compounds of this invention are illustrated in the following schemes. Unless otherwise specified, variables are defined as above. Other synthetic protocols will be readily apparent to those skilled in the art.

Scheme 1
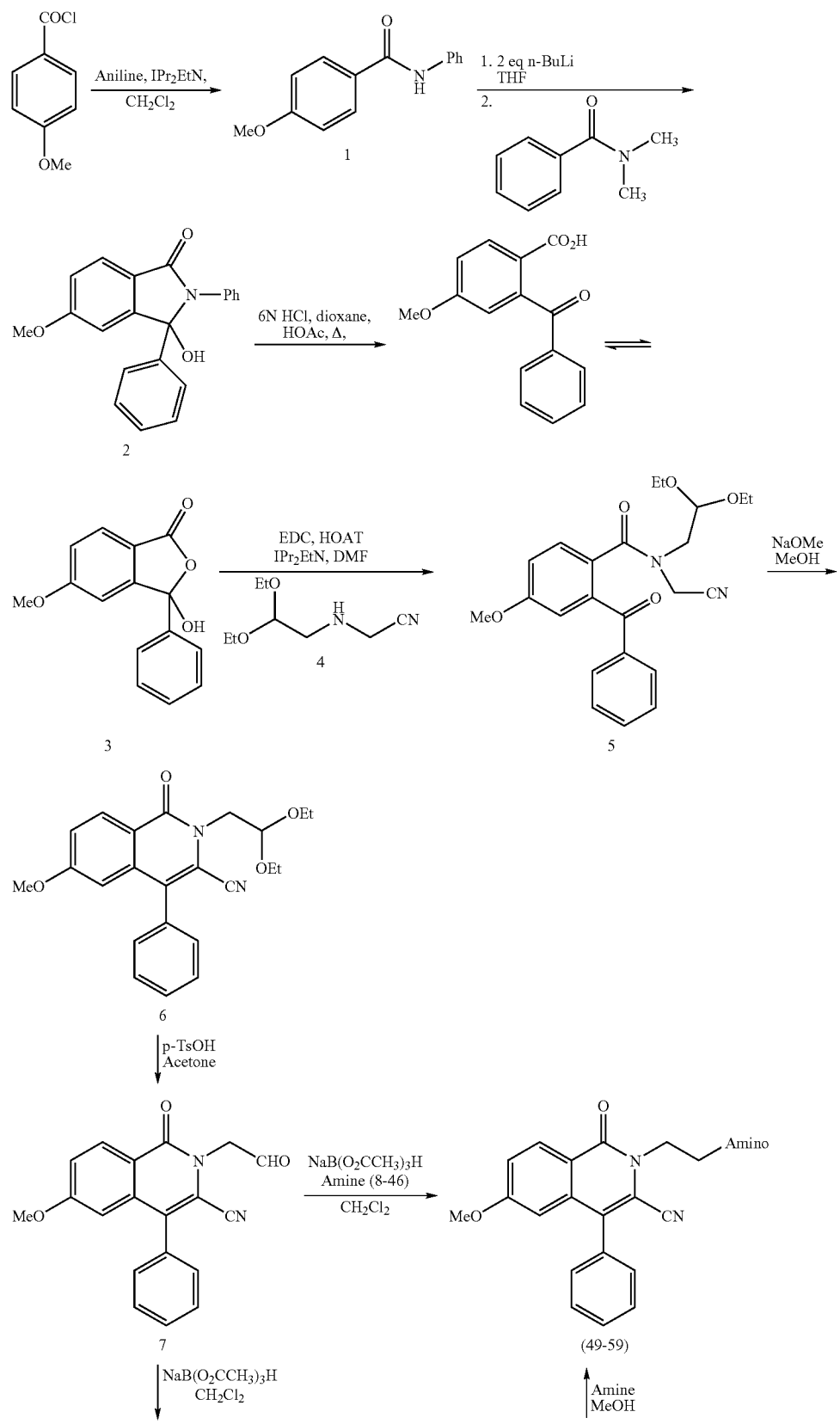

-continued
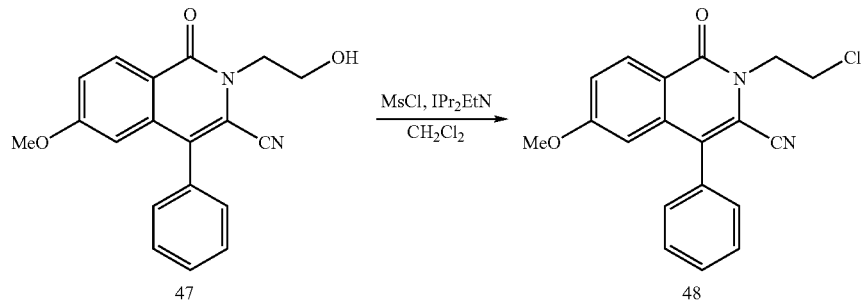
Scheme 2
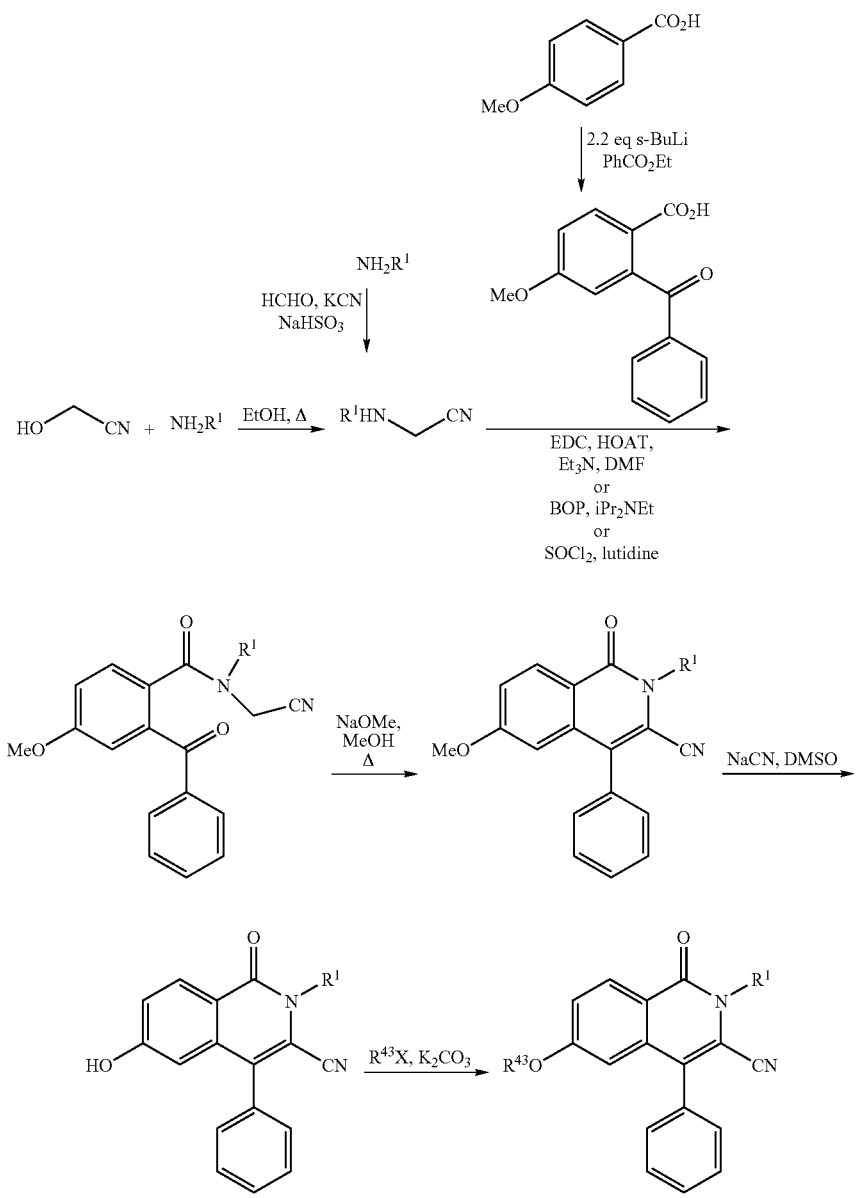

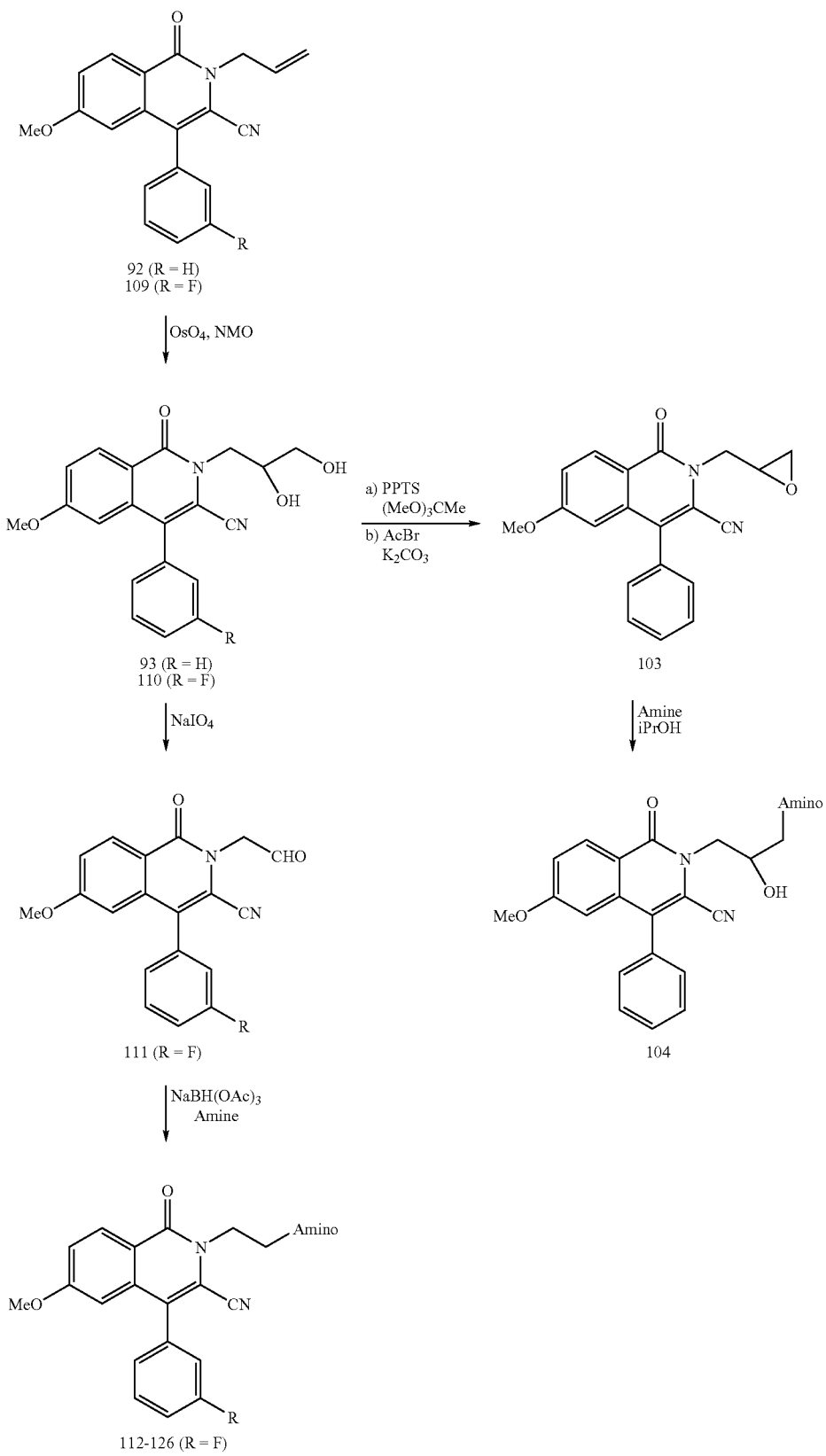

Scheme 4

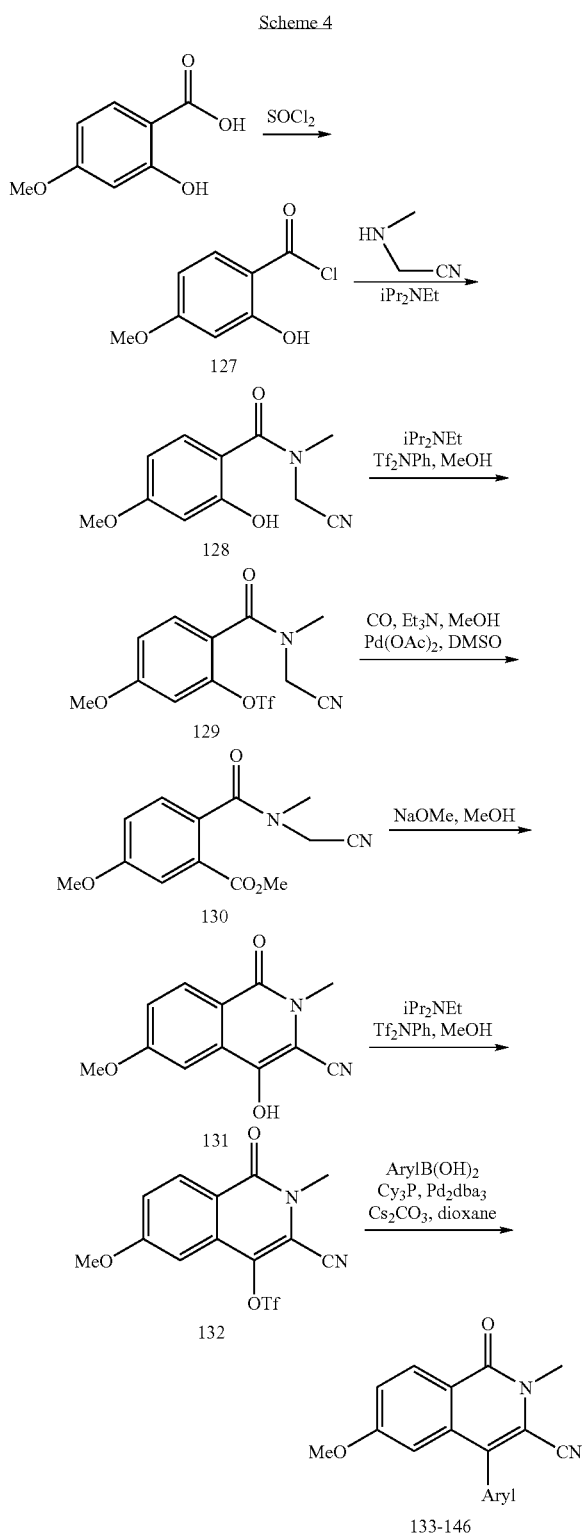

The following examples illustrate the preparation of the compounds of Formula I and as such are not to be considered as limiting the invention set forth in the claims appended hereto. Examples provided are intended to assist in a further understanding of the invention. Particular materials employed, species and conditions are intended to be further illustrative of the invention and not limiting of the reasonable scope thereof. In all cases, the proton NMR for each product was consistent with that of the structure shown.

EXAMPLE I

Preparation of 2-(2-Amino-(5,6,7,8-tetrahydro-1-naphthyl)ethyl)-3-cyano-6-methoxy-4-phenyl-2H-isoquinolin-1-one (8)

Step A: 4-Methoxy-N-phenyl-benzamide (1)

p-Anisoyl chloride (10 g, 58.5 mmol) was dissolved in methylene chloride (500 mL) under argon. Aniline (8.0 mL, 87.7 mmol) was added dropwise with stirring. Diisopropylethylamine (10.0 mL, 58.5 mmol) was added dropwise to give a white suspension. After 3 h the contents of the reaction flask were washed with 5% potassium bisulfate then sat. sodium bicarbonate. The organic portion was dried with sodium sulfate (anh.), filtered and evaporated in vacuo to give a solid. Trituration with ethyl acetate gave the title compound 1 as a white solid (3.37 g, 25%)

$^1$HNMR (CHCl$_3$, 300 MHz) δ 7.88-7.82 (m, 2H); 7.74 (s, br, 1H); 7.66-7.60 (m, 2H); 7.42-7.34 (m, 2H), 7.18-7.10 (m, 1H); 7.02-6.94 (m, 2H); 3.88 (s, 3H).

Step B: 3-Hydroxy-5-methoxy-2,3-diphenyl-2,3-dihydro-isoindol-1-one (2)

While cooling in a dry ice/isopropanol bath, to a solution of 1 (3.00 g, 13.2 mmol) in tetrahydrofuran at −78° C. was added dropwise n-butyllithium (2.5M in hexanes, 11.1 mL, 27.8 mmol). After stirring for 0.5 h the reaction mixture was warmed over 0.5 h to −15° C. It was recooled in the IPA/dry ice bath then a tetrahydrofuran solution of N,N-dimethylbenzamide (2.38 g, 15.8 mmol) was added. The reaction mixture was warmed to room temperature and quenched with water. The solvent was removed in vacuo. Sat. sodium bicarbonate was added and the mixture extracted with ethyl acetate (3×). The combined organic portions were dried with sodium sulfate (anh.), filtered, and concentrated. A solid resulted. It was triturated with ether to give 2 as a white solid (3.11 g, 71%)

$^1$HNMR (CHCl$_3$, 300 MHz) δ 7.60 (d, 1H); 7.48-7.35 (m, 4H); 7.28-7.05 (m, 6H); 6.85 (m, 1H), 6.75 (m, 1H); 4.00 (s, 1H); 3.79 (s, 3H).

Step C: 3-Hydroxy-5-methoxy-3-phenyl-3H-isobenzofuran-1-one (3)

A solution of 2 (3.11 g, 9.39 mmol) in a mixture of 6N hydrochloric acid (150 mL) and dioxane (150 mL) was heated at reflux under Ar for 18 h. Acetic acid (50 mL) was added and heating was continued for an additional 4 h. The organic solvents were removed in vacuo and the remaining aqueous was extracted with ethyl acetate (3×), washed with brine and dried with sodium sulfate (anh.). Filtration followed by removal of the solvent in vacuo gave 3 as a white solid (1.32 g, 55%)

$^1$HNMR (CHCl$_3$, 300 MHz) δ 8.05 (d, 1H); 7.74 (d, 2H); 7.55 (m, 1H); 7.41 (m, 2H), 7.02 (m, 1H); 6.83 (m, 1H); 3.86 (s, 3H).

Step D: [(2,2-Diethoxyethyl)amino]-acetonitrile (4)

A mixture of glycolonitrile (8.33 g, 70% solution in water, 0.1 mol) and aminoacetaldehyde diethyl acetal (14.5 mL, 0.1 mol) was heated to reflux for 3 h. After cooling, the mixture was filtered to remove traces of solid and the filtrate then concentrated in vacuo to give the desired product 4.

$^1$HNMR (CHCl$_3$, 300 MHz) δ 4.61 (t, 1H, J=5.18 Hz); 3.72 (m, 2H); 3.64 (s, 2H); 3.55 (m, 2H); 2.86 (d, J=5.19 Hz); 1.78 (brs); 1.23 (t, 6H, J=7.0 Hz)

Step E: 2-Benzoyl-N-cyanomethyl-N-(2,2-diethoxyethyl)-4-methoxybenzamide (5)

A solution of 3 (1.00 g, 3.91 mmol), 4 (740 mg, 4.30 mmol), 1-[3-(dimethylamino)propyl]-3-ethylcarbodiimide hydrochloride (826 mg, 4.30 mmol), 1-hydroxy-7-azabenzotriazole (585 mg, 4.30 mmol) and NN-diisopropylethylamine (0.748 mL, 4.30 mmol) in N,N-dimethylformamide (5 mL) was stirred at room temperature for 2 days. The contents of the reaction flask were poured into water and sat. sodium bicarbonate then extracted with ethyl acetate (3×). The combined organic extracts were washed with 5% potassium bisulfate and brine. The organic layer was dried with sodium sulfate (anh.), filtered and concentrated in vacuo. Flash column chromatography (hexane/ethyl acetate 70:30) gave 5 (1.05 g, 68%)

$^1$HNMR (CHCl$_3$, 300 MHz) δ 7.86 (d, br, 2H); 7.60 (m, 1H); 7.52-7.40 (m, 3H); 7.14-7.06 (m, 2H); 4.40 (s, 2H); 3.87 (s, 3H); 3.80-3.40 (m, 7H); 1.30 (m, 6H).

Step F: 3-Cyano-2-(2,2-diethoxyethyl)-6-methoxy-4-phenyl-2H-isoquinolin-1-one (6)

A solution of 5 (1.05 g, 2.65 mmol), sodium methoxide (4.62M in methanol, 1.43 mL, 6.63 mmol) and methanol (50 mL) was heated at reflux for 2 h. The solvent was removed in vacuo and sat. sodium bicarbonate was added. The resulting mixture was extracted with methylene chloride (3×). The combined organic extracts were dried with magnesium sulfate (anh.) and filtered. The filtrate was concentrated in vacuo to give an oil which was triturated with hexane/ethyl acetate to give 6 as a white solid (805 mg, 77%)

$^1$HNMR (CHCl$_3$, 300 MHz) δ 8.45 (d, 1H); 7.60-7.50 (m, 3H); 7.44-7.36 (m, 2H); 7.22 (dd, 1H), 6.64 (d, 1H); 4.92 (t, 1H); 4.44 (d, 2H); 3.87-3.76 (m, 2H); 3.75 (s, 3H); 3.60-3.47 (s, 2H); 1.19 (t, 6H).

Step G: 3-Cyano-methoxy-2-(2-oxoethyl)-4-phenyl-2H-isoquinolin-1-one (7)

A solution of 6 (805 mg, 2.50 mmol) and p-toluenesulfonic acid (cat.) in acetone (40 mL) was heated to 40° C. under Ar for 8 h. Saturated sodium bicarbonate was added and the mixture was evaporated in vacuo to remove the organic solvent. The resulting mixture was extracted with ethyl acetate (3×). The combined organic extracts were dried with magnesium sulfate (anh.) and filtered. The filtrate was concentrated in vacuo to give an oil which was subjected to flash column chromatography (hexane/ethyl acetate, 70:30 to 20:80) give 7 as a white solid (479 mg, 73%)

$^1$HNMR (CHCl$_3$, 300 MHz) δ 9.80 (s, 1H); 8.45 (d, 2H); 7.60-7.52 (m, 3H); 7.48-7.42 (m, 2H), 7.26-7.20 (m, 1H); 6.70 (d, 1H); 5.19 (s, 2H); 3.77 (s, 3H).

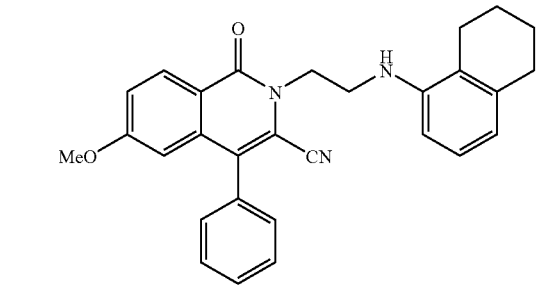

Step H: 2-2-Amino-(5,6,7,8 tetrahydro-1-naphthyl)ethyl)-3-cyano-6-methoxy-4-phenyl-2H-isoquinolin-1-one (8)

A solution of 7 (25.0 mg, 0.0786 mmol), sodium triacetoxyborohydride (25.0 mg, 0.118 mmol), and 1-amino-5,6,7,8-tetrahydronaphthalene (12.0 mg, 0.0786 mmol) in methylene chloride (0.250 mL) was stirred under Ar at room temperature for 48 h. Saturated sodium bicarbonate was added and the organic phase was passed through a pasteur pipet containing magnesium sulfate (anh.). Evaporation of the solvent in vacuo followed by trituration with ether gave 8 as a solid.

$^1$HNMR (CHCl$_3$, 300 MHz) δ 8.48 (d, 1H); 7.54 (m, 3H); 7.35 (m, 2H); 7.23 (dd, 1H), 6.92 (m, 1H); 6.61 (d, 1H); 6.46 (m, 2H); 4.65 (m, 2H); 4.37 (m, 1H); 3.76 (s, 3H); 3.70 (m, 2H); 2.70 (m, 2H); 2.41 (m, 2H); 1.86 (m, 2H); 1.71 (m, 2H).

Compounds 9-46 (Table 1) were prepared essentially according to the procedures described above in Example I for the preparation of compound 8 by substituting the appropriate amine in Step H. While Example I, Step H describes a specific set of conditions for performing a reductive amination reaction it is understood that modifications of said protocol or the use of other standard protocols may be required to access any or all of compounds 9-46. Said modifications and alternate protocols would be well known to and executable by anyone reasonably skilled in the art.

TABLE 1

Data for Compounds 9-46

| Compound | Amino | MS [M + H]$^+$ |
|---|---|---|
| 9 | 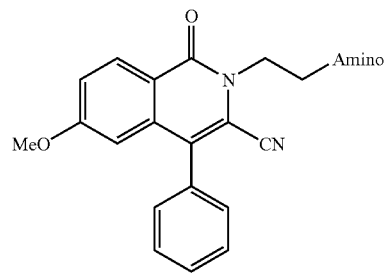 | 374.19 |

TABLE 1-continued
Data for Compounds 9-46
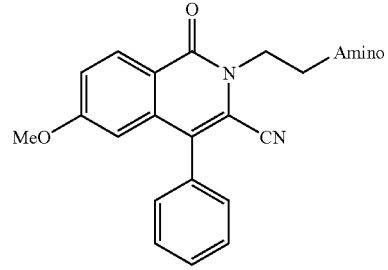
| Compound | Amino | MS [M + H]+ |
|---|---|---|
| 10 | 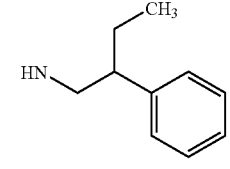 | 452.23 |
| 11 | 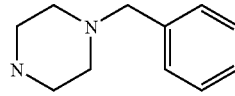 | 500.23 |
| 12 | 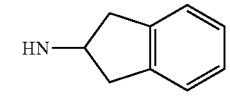 | 479.25 |
| 13 | 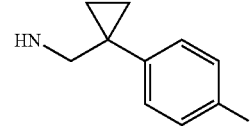 | 436.20 |
| 14 | 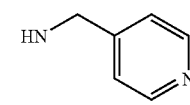 | 484.18 |
| 15 | 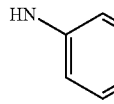 | 411.18 |
| 16 | 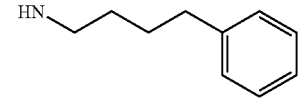 | 396.16 |
| 17 | 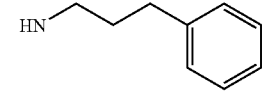 | 452.23 |
| 18 |  | 438.21 |

TABLE 1-continued

Data for Compounds 9-46

| Compound | Amino | MS [M + H]⁺ |
|---|---|---|
| 19 | tert-butylamino (HN-C(CH₃)₃) | 376.20 |
| 20 | cyclohexylmethylamino | 416.23 |
| 21 | (S)-1-phenylethylamino | 424.20 |
| 22 | 4-phenylpiperazin-1-yl | 465.22 |
| 23 | piperidin-1-yl | 388.20 |
| 24 | diphenylmethylamino | 486.21 |
| 25 | pentan-3-ylamino | 376.20 |
| 26 | benzylamino | 410.18 |
| 27 | 4-phenyl-4-(aminomethyl)cyclohexyl N-methylcarbamate | 565.27 |

TABLE 1-continued

Data for Compounds 9-46

[Structure: 6-methoxy-2-(2-aminoethyl)-4-phenyl-1-oxo-1,2-dihydroisoquinoline-3-carbonitrile]

| Compound | Amino | MS [M + H]⁺ |
|---|---|---|
| 28 | HN-CH₂-C(CH₃)₂-Ph | 452.23 |
| 29 | 1,2,3,4-tetrahydroisoquinolin-2-yl | 436.20 |
| 30 | HN-CH₂-(2-thienyl) | 416.14 |
| 31 | HN-(indan-1-yl) | 436.20 |
| 32 | 4-methylpiperazin-1-yl | 403.21 |
| 33 | morpholin-4-yl | 390.18 |
| 34 | HN-iPr | 362.18 |
| 35 | HN-cyclohexyl | 402.21 |
| 36 | HN-CH₂-cyclopropyl | 374.18 |
| 37 | N(CH₃)-cyclohexyl | 416.23 |

TABLE 1-continued

Data for Compounds 9-46

[Structure: 6-methoxy-1-oxo-4-phenyl-2-(2-Amino-ethyl)-isoquinoline-3-carbonitrile]

| Compound | Amino | MS [M + H]+ |
|---|---|---|
| 38 | HN-CH2CH2-phenyl | 424.20 |
| 39 | HN-(2-pyridyl) | 397.16 |
| 40 | HN-CH(CH3)-phenyl (S) | 424.20 |
| 41 | HN-CH2-(3-pyridyl) | 411.18 |
| 42 | HN-(CH2)3-imidazol-1-yl | 428.20 |
| 43 | HN-(CH2)3-(2-oxopyrrolidin-1-yl) | 445.22 |
| 44 | HN-CH2-C(CH3)3 (neopentyl) | 404.23 |
| 45 | HN-CH2CH2-NHC(O)CH3 | 405.19 |
| 46 | [bis-isoquinolinone linked by -CH2CH2-N(CH3)-CH2CH2-] | 636.25 |

EXAMPLE II

Preparation of 3-Cyano-2-(2-hydroxyethyl)-6-methoxy-4-phenyl-2H-isoquinolin-1-one (47)

A solution of 7 (250 mg, 0.786 mmol), and sodium triacetoxyborohydride (333 mg, 1.57 mmol) in methylene chloride (10 mL) was stirred for 24 h at room temperature. Saturated sodium bicarbonate was added and the mixture was extracted with methylene chloride (3×). The combined organic extracts were dried with magnesium sulfate (anh.) and filtered. The filtrate was concentrated in vacuo to give 47 as a white solid.

$^1$HNMR (CHCl$_3$, 300 MHz) δ 8.46 (d, 1H); 7.55 (m, 3H); 7.42 (m, 2H); 7.23 (dd, 1H), 6.67 (d, 1H); 4.55 (m, 2H); 4.10 (m, 2H); 3.76 (s, 3H); 2.55 (m, 1H).

EXAMPLE III

Preparation of 2-2-Chloroethyl)-3-cyano-6-methoxy-4-phenyl-2H-isoquinolin-1-one (48)

To a solution of 47 (217 mg, 0.679 mmol), and diisopropylethylamine (0.153 mL, 0.883 mmol) in methylene chloride (2 mL) under nitrogen was added methanesulfonyl chloride (0.068 mL, 0.883 mmol). After 3 h saturated sodium bicarbonate was added and the mixture was extracted with methylene chloride (3×). The combined organic extracts were dried with magnesium sulfate (anh.) and filtered. The filtrate was concentrated in vacuo to give a colorless oil which was subjected to flash column chromatography (ethyl acetate/hexane) to give 48 as a light solid.

$^1$HNMR (CHCl$_3$, 300 MHz) δ 8.46 (d, 1H); 7.56 (m, 3H); 7.43 (m, 2H); 7.22 (dd, 1H), 4.65 (t, 2H); 3.96 (t, 2H); 3.75 (s, 3H).

EXAMPLE IV

Preparation of 3-Cyano-2-(2-(cyclopropylamino)ethyl)-6-methoxy-4-phenyl-2H-isoquinolin-1-one (49)

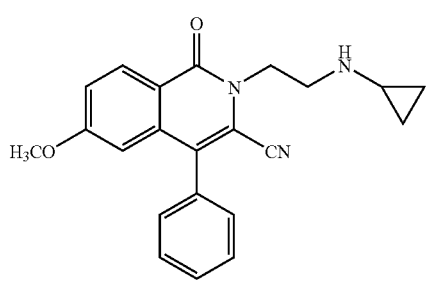

In a threaded glass tube under nitrogen were combined 48 (40.0 mg, 0.118 mmol), cyclopropylamine (0.500 mL, 7.23 mmol) and methanol (5 mL). The tube was sealed and heated in a 80° C. oil bath. After 24 h the tube was cooled and the contents evaporated in vacuo. Saturated solium bicarbonate was added and the resulting mixture extracted with methylene chloride (3×). The combined organic extracts were dried with magnesium sulfate (anh.) and filtered. The filtrate was concentrated in vacuo to give a yellow oil which was triturated with hexane/ethyl acetate to give 49 as a white solid.

MS [M+H]$^+$ 360.2

Compounds 50-56 (Table 2) were prepared essentially according to the procedure described above in Example IV for the preparation of compound 49 by substituting the appropriate amine. While Example IV describes a specific set of conditions it is understood that modifications of said protocol or the use of other standard protocols may be required to access any or all of compounds 50 -56. Said modifications and alternate protocols would be well known to and executable by anyone reasonably skilled in the art.

TABLE 2

Data for Compounds 50-56

| Compound | Amino | MS [M + H]$^+$ |
|---|---|---|
| 50 | N(CH$_3$)$_2$ | 348.2 |
| 51 | piperazine-pyrimidin-2-yl | 467.2 |
| 52 | 4-(4-methoxyphenyl)piperazine | 495.2 |
| 53 | 4-(3-methoxyphenyl)piperazine | 495.2 |
| 54 | 4-(2-methoxyphenyl)piperazine | 495.2 |
| 55 | 4-(4-fluorophenyl)piperazine | 483.2 |
| 56 | 4-(4-trifluoromethylphenyl)piperazine | 533.2 |

EXAMPLE V

Preparation of [2-(3-Cyano-6-methoxy-1-oxo-4-phenyl-1H-isoquinolin-2-yl)-ethyl]-carbamic acid tert-butyl ester (56a)

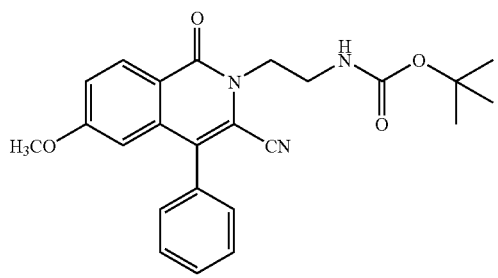

Compound 56a was prepared essentially according to the procedure described above in Example I for compound 8 by using tert-butyl-N-2-aminoethyl)-carbamate in place of aminoacetaldehyde diethyl acetal in Step D.

$^1$HNMR (CHCl$_3$, 300 MHz) δ 8.46 (d, 1H); 7.60-7.50 (m, 3H); 7.50-7.40 (m, 2H); 7.22 (dd, 1H); 6.66 (d, 1H); 5.00 (s, br, 1H); 4.45 (m, 2H); 3.75 (s, 3H); 3.65 (m, 2H); 1.30 (s, 9H).

EXAMPLE VI

Preparation of [2-(3-Cyano-6-methoxy-1-oxo-4-phenyl-1H-isoquinolin-2-yl)methylpiperidin-4-yl]-carbamic acid tert-butyl ester (57)

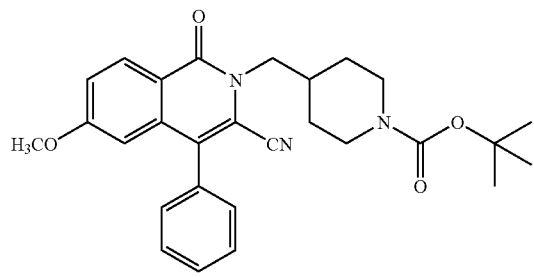

Compound 57 was prepared essentially according to the procedure described above in Example I for compound 8 by substituting tert-butyl-N-(4-aminomethylpiperidinyl) carbamate in place of aminoacetaldehyde diethyl acetal in Step D.

$^1$HNMR (CHCl$_3$, 300 MHz) δ 8.46 (d, 1H); 7.58-7.52 (m, 3H); 7.46-7.38 (m, 2H); 7.22 (dd, 1H); 6.66 (d, 1H); 4.25-4.05 (m, br, 4H); 3.76 (s, 3H); 2.68 (m, 2H); 2.16 (m, 1H); 1.70 (m, 2H); 1.48 (m, 11H).

Example VII

Preparation of 3-Cyano-6-methoxy-4-phenyl-2-[(piperidin-4-yl)methyl]-2H-isoquinolin-1-one hydrochloride (58)

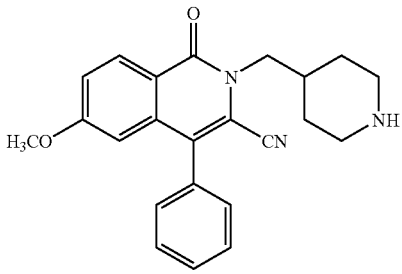

A solution of 57 (200 mg, 0.423 mmol) in ethyl acetate (100 mL) was cooled in an ice bath and treated with hydrogen chloride gas for 10 min. The resulting solution was stirred 1.5 h and then warmed to room temperature. Evaporation of the solvent in vacuo gave 58 as a white solid.

MS [M+H]$^+$ 374.2

EXAMPLE VIII

Preparation of 2-Cyclopropyl-4-(3-fluorophenyl)-6-methoxy-1-oxo-1,2-dihydroisoquinoline-3-carbonitrile (61)

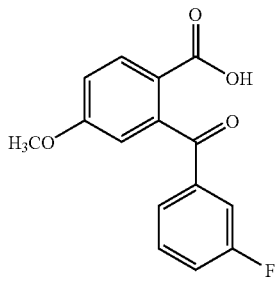

Step A: 2-(3-fluorobenzoyl)-4-methoxybenzoic acid (59)

s-Butyllithium (52 mL, 1.4 M in pentane, 72 mmol) was added at −78° C. over 90 min. to a solution of p-anisic acid (5 g, 33 mmol) and TMEDA (11 ml, 72 mmol) in THF (80 mL). After stirring for 15 min., ethyl 3-fluorobenzoate (5 mL, 40 mmol) was added in one portion. The reaction mixture was stirred for 15 min. then it was quenched with water (20 mL). The reaction mixture was then warmed to room temperature and poured into water (1.5 L) 1N NaOH (30 ml) was added and the reaction mixture was then extracted with EtOAc. The extracts were discarded. The aqueous phase was then acidified with conc. HCl to pH 1 and extracted with EtOAc. Drying (Na$_2$SO$_4$) and concentration gave a residue which was recrystallized from hexanes/EtOAc to give the title compound 59 as a white solid.

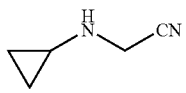

Step B: (Cyclopropylamino)acetonitrile (60)

Formaldehyde (37 wt % in water, 13.4 ml, 175 mmol) was added to a solution of sodium bisulfite (18.2 g, 175 mmol) in water (64 ml) at 0° C. After stirring for 1.5 h, cyclopropylamine (12 ml, 175 mmol) was added quickly in one portion. The reaction mixture was then warmed to room temperature and stirred for 1.5 h. A solution of KCN (11.4 g, 175 mmol) in water (25 ml) was added and the reaction mixture then stirred overnight. The reaction mixture was then extracted with benzene and the extracts dried over $Na_2SO_4$. Concentration gave the desired product as a yellow oil which was used without purification.

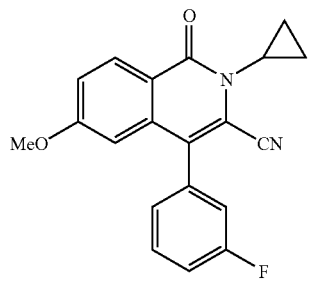

Step C: 2-Cyclopropyl-4-3-fluorophenyl)-6-methoxy-1-oxo-1,2-dihydroisoquinoline-3-carbonitrile (61)

The acid 59 (3.2 g, 11.7 mmol) was azeotroped with toluene and then dissolved in dry methylene chloride (50 mL). Thionyl chloride (2.8 ml, 17.6 mmol) was added followed by 5 drops of dry DMF and the resulting mixture was heated at reflux for 30 min. After cooling to ambient temperature the volatile components were removed under reduced pressure and the residue was then azeotroped with toluene. The resulting material was taken up in dry toluene (50 mL), to which the amine (1.7 g, 17.6 mmol) and 2,6-lutidine (2.7 ml, 23.5 mmol) were added. The resulting mixture was heated at reflux overnight. EtOH (50 ml) and NaOMe (4.4 M in methanol, 8 ml, 35 mmol) were then added and the mixture then allowed to cool to 80 C and stirred there for 30 minutes. The reaction was further cooled to room temperature, diluted with water and extracted with EtOAc. The combined organics were washed 1N HCl, dried with Na2SO4, filtered and concentrated in vacuo. The residue was purified by crystallization from hot hexanes/EtOAc and hexanes, providing solid 61.

EXAMPLE IX

Preparation of 2-cyclopropyl-4-(3-fluorophenyl)-6-hydroxy-1-oxo-1,2-dihydroisoquinoline-3-carbonitrile (62)

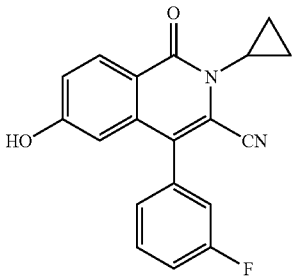

A mixture of the methyl ether 61 (3 g, 9 mmol) and NaCN (3.5 g, 72 mmol) in DMSO was heated at 160° C. for 3 h. The mixture was cooled, diluted with water, acidified with concentrated HCl and then extracted with EtOAc. The combined organic extracts were basified with 1N NaOH and washed with EtOAc. The aqueous layer was acidified with concentrated HCl and then extracted with EtOAc. Drying with $Na_2SO_4$ and concentration in vacuo gave a residue was purified by crystallization from EtOAc/hexanes.

HRMS (ES) for C19H14N2O2F, Theoretical 321.1034, Found 321.1049

EXAMPLE X

Preparation of 2-cyclopropyl-4-(3-fluorophenyl)-1-oxo-6-(2,2,2-trifluoroethoxy)-1,2-dihydroisoquinoline-3-carbonitrile (63)

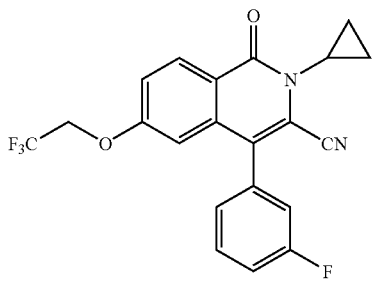

A mixture of the phenol 62 (64 mg, 0.2 mmol), $K_2CO_3$ (83 mg, 0.6 mmol) and trifluoroethyl triflate (70 mg, 0.3 mmol) in DMF (3 mL) was heated at 50° C. for 30 min. The reaction was cooled, poured into saturated aqueous $NaHCO_3$ and extracted with EtOAc. The combined organic extracts were washed once with 1N HCl and brine, dried with $Na_2SO_4$, filtered and concentrated in vacuo. Trituration of the residue with EtOAc/Hexane provided desired product 63.

HRMS (ES) for $C_{21}H_{15}N_2O_2F_4$, Theoretical 403.1064, Found 403.1053

Compounds 64-69 (Table 3) were prepared essentially according to the procedure described above in Example X for the preparation of compound 63 by substituting an appropriate electrophile for trifluoroethyl triflate. It will be obvious to those skilled in the art that for some compounds, said electrophile must be suitably protected prior to use. Furthermore, the choice of suitable protection and deprotection protocols would be well known to and executable by anyone reasonably skilled in the art.

TABLE 3

Data for Compounds 64-69

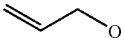

| Compound | RO | Formula | HRMS Theoretical | HRMS (ES) Found |
|---|---|---|---|---|
| 64 | 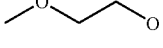 | C$_{22}$H$_{18}$N$_2$O$_2$F | 361.1347 | 361.1342 |
| 65 |  | C$_{22}$H$_{20}$N$_2$O$_2$F | 379.1453 | 379.1446 |
| 66 |  | C$_{21}$H$_{18}$N$_2$O$_2$F | 349.1347 | 349.1348 |
| 67 | 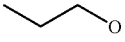 | C$_{20}$H$_{15}$N$_2$O$_2$F$_2$ | 353.1096 | 353.1114 |
| 68 | 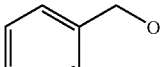 | C$_{22}$H$_{20}$N$_2$O$_2$F | 363.1504 | 363.1497 |
| 69 | 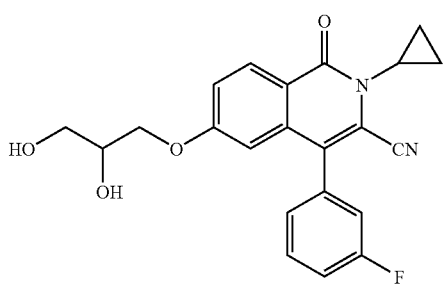 | C$_{26}$H$_{20}$N$_2$O$_2$F | 411.1504 | 411.1492 |

EXAMPLE XI

Preparation of 2-cyclopropyl-6-(2,3-dihydroxypropoxy)-4-(3-fluorophenyl)-1-oxo-1,2-dihydroisoquinoline-3-carbonitrile (70)

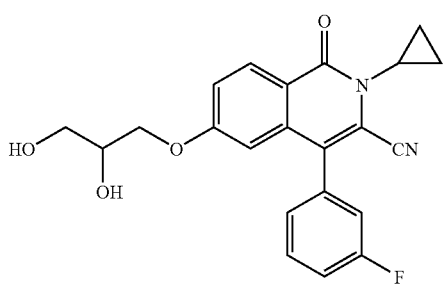

To a solution of the allyl ether 64 (40 mg, 111 mmol) in acetone (6 ml) and water (2.5 mL) was added OsO$_4$ (0.15 mL, 2.5 wt % in t-butanol, 11 mmol) followed by NMO (16 mg, 133 mmol). After stirring at room temperature for 4 h, the mixture was poured into a 1:1 mixture of saturated NaHCO$_3$/Na$_2$SO$_3$ and extracted with EtOAc. The combined organic layers were dried over Na$_2$SO$_4$, filtered and concentrated in vacuo. The residue was triturated with hot hexane/EtOAc, providing desired product 70.

HRMS (ES) for C$_{22}$H$_{20}$N$_2$O$_4$F, Theoretical 395.1402, Found 395.1402

EXAMPLE XII

Preparation of 6-[2-(benzyloxy)ethoxyl]-2-cyclopropyl-4-(3-fluorophenyl)-1-oxo-1,2-dihydroisoquinoline-3-carbonitrile (71)

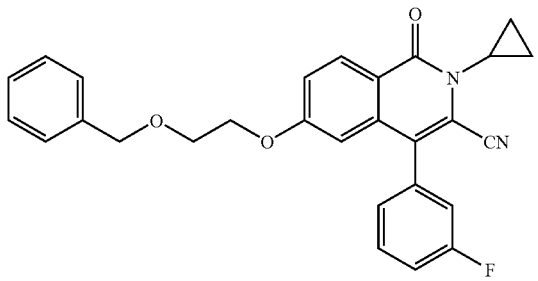

A mixture of the phenol 62 (80 mg, 0.25 mmol), K$_2$CO$_3$ (104 mg, 0.75 mmol) and benzyloxyethyl bromide (64 mg, 0.3 mmol) in DMF (3 mL) was heated in a microwave reactor at 120° C. for 15 min. The mixture was filtered and directly purified using an automated high pressure chromatography unit.

HRMS (ES) for C$_{28}$H$_{24}$N$_2$O$_3$F, Theoretical 455.1766, Found 455.1766

Compounds 72-82 (Table 4) were prepared essentially according to the procedure described above in Example XII for the preparation of compound 71 by substituting an appropriate electrophile for benzyloxyethyl bromide. For some compounds it will be obvious to those skilled in the art that said electrophile must be suitably protected prior to use. Furthermore, the choice of suitable protection and deprotection protocols would be well known to and executable by anyone reasonably the art.

TABLE 4
Data for Compounds 72-82
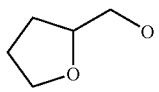
| Compound | RO | Formula | HRMS Theoretical | HRMS (ES) Found |
|---|---|---|---|---|
| 72 | 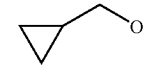 | $C_{24}H_{22}N_2O_3F$ | 405.1609 | 405.1595 |
| 73 | 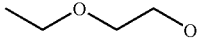 | $C_{23}H_{20}N_2O_2F$ | 375.1504 | 375.1495 |
| 74 | 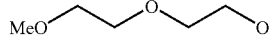 | $C_{23}H_{22}N_2O_3F$ | 393.1609 | 393.1609 |
| 75 | 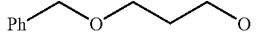 | $C_{24}H_{24}N_2O_4F$ | 423.1715 | 423.1705 |
| 76 | 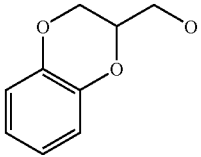 | $C_{29}H_{26}N_2O_3F$ | 469.1922 | 469.1937 |
| 77 | 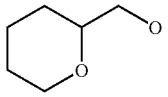 | $C_{28}H_{22}N_2O_4F$ | 469.1558 | 469.1562 |
| 78 | 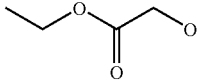 | $C_{25}H_{24}N_2O_3F$ | 41901766 | 419.175 |
| 79 | 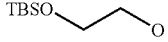 | | LRMS | 407.2 |
| 80 | 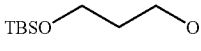 | | LRMS | 479.2 |
| 81 | 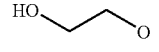 | | LRMS | 493.45 |
| 82 | HO⌒O | $C_{21}H_{18}N_2O_3F$ | 365.1926 | 365.1923 |

EXAMPLE XIII

Preparation of 2-Cyclopropyl-6-(difluoromethoxy)-4-(3-fluorophenyl)-1-oxo-1,2-dihydroisoquinoline-3-carbonitrile (83)

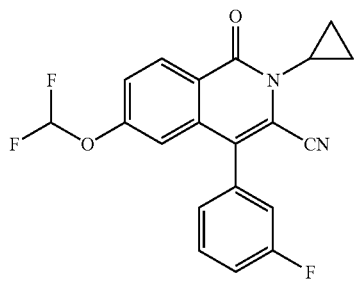

The phenol 62 (105 mg, 0.33 mmol) was dissolved in DMF (5 mL). K₂CO₃ (136 mg, 0.98 mmol) was added and the mixture was cooled to 0° C. in a sealable tube. Freon was bubbled through the mixture for 5 minutes and the vessel was then sealed and heated at 100 C for 15 h. The mixture was cooled to ambient temperature, poured into NaHCO₃(sat) and extracted with EtOAc. The combined organic extracts were washed with brine, dried with Na₂SO₄, filtered and concentrated in vacuo. The residue was purified by automated flash chromatography (100/0 to 0/100 Hex/EtOAc, providing desired product 83.

HRMS (ES) for $C_{20}H_{13}N_2O_2F_3$, Theoretical 371.1002, Found 371.1003

EXAMPLE XIV

Preparation of 4-(2-Fluorophenyl)-6-methoxy-2-methyl-1-oxy-1,2-dihdroisoquinoline-3-carbonitrile (86)

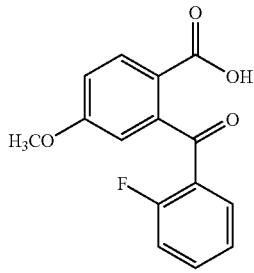

Step A: 2-(2-Fluorobenzoyl)-4-methoxybenzoic acid (84)

4-(Methoxy)benzoic acid (5.00 g, 32.9 mmol) was azeotroped with toluene thrice, then dissolved in 80 mL of dry THF. TMEDA (10.9 mL, 72.3 mmol) was added, and the mixture was cooled to −78° C. sec-BuLi (51.6 mL of 1.40 M in cyclohexane, 72.3 mmol) was added dropwise over a period of 30 minutes, and the solution was stirred for 15 minutes. Methyl 2-fluorobenzoate (5.02 mL, 39.4 mmol) was added in 1 portion and, after stirring for 15 minutes, the reaction was quenched with 20 mL of water. The mixture was warmed to ambient temperature and poured into 1.5 L of water. 30 mL 1N NaOH was added and the aqueous layer was extracted 1× with EtOAc; after which the organic layer was discarded. The aqueous layer was acidified with conc. HCl until pH=1 and then extracted 2× with EtOAc. The combined organic extracts were dried with Na₂SO₄, filtered and concentrated in vacuo. The crude residue was purified by flash chomatography through SiO₂ (40-100% EtOAc/hexane) to provide the desired product (4.72 g, 52% yield) as a white solid. ESI+MS: 275.2 [M+H+].

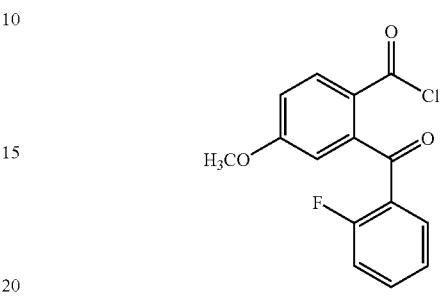

Step B: 2-(2-fluorobenzoyl)-4-methoxybenzoyl chloride (85)

To a solution of 2-2-fluorobenzoyl)-4-methoxybenzoic acid (84) (2.05 g, 7.48 mmol) in 50 mL of dichloromethane was added thionyl chloride (2.40 mL, 14.9 mmol), followed by 3 drops of DMF. The reaction was warmed to reflux. After 1 hour, LC-MS (aliquot quenched with pyrrolidine/ACN/H2O) showed that the reaction was complete (ESI+MS for corresponding pyrrolidine amide: 328.2 [M+H]+). The reaction was concentrated in vacuo to provide an oil which was used in the next step without further purification.

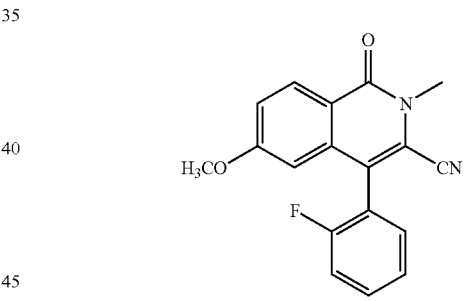

Step C: 4-(2-Fluorophenyl)-6-methoxy-2-methyl-1-oxo-1,2-dihydroisoquinoline-3-carbonitrile (86)

To solution of 2-2-fluorobenzoyl)-4-methoxybenzoyl chloride (285 mg, 0.974 mmol) in toluene (10 mL) was added 2,6-lutidine (227 mL, 1.95 mmol) and (methylamino)acetonitrile (96 mL, 1.27 mmol). The mixture was heated to reflux. After 16 hours, the solution was cooled, 10 mL of ethanol was added, then sodium methoxide solution was added (0.67 mL of 4.37 M in methanol, 2.92 mmol). The reaction was heated to 80 ° C. for one hour, then cooled to room temperature. The solution was partitioned between EtOAc and water, washed with 3 N HCl solution, dried with Na₂SO₄, and concentrated in vacuo to provide a white solid. Trituration with 20% EtOAc/hexane provided the titled product 86 as a white solid.

1H-NMR (500 MHz, CDCl3) δ 8.46 (d, J=9.0 Hz, 1H), 7.55 (m, 1H), 7.40 (br t, J=6.5 Hz, 1H), 7.35 (br t, J=7.4 Hz, 1H), 7.29 (br t, J=9 Hz, 1H), 7.22 (br d, J=8.5 Hz, 1H), 6.56 (br s, 1H), 3.84 (s, 3H), 3.77 (s, 3H), ppm.

EXAMPLE XV

Preparation of 2-Allyl-4-(2-fluorophenyl)-6-methoxy-1-oxo-1,2-dihydroisoquinoline-3-carbonitrile (87)

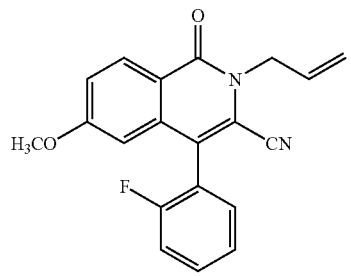

Following the procedure described in Step C of Example XVII, replacing (methylamino)acetonitrile with (allylamino)acetonitrile (from Step B of Example VIII), the title compound 87 was obtained. Proton NMR for the product was consistent with the titled compound.

HRMS (ES) exact mass calculated for $C_{20}H_{16}FN_2O_2$ (M+H+): 335.1191. Found 335.1188.

EXAMPLE XVI

Preparation of 2-allyl-6-methoxy-1-oxo-4-phenyl-1,2-dihydroisoquinoline-3-carbonitrile (88)

Compound 88 was prepared essentially according the procedure described in Example XIV, by replacing key reagents as appropriate. Proton NMR for the product was consistent with the titled compound.

HRMS (ES) exact mass calculated for $C_{20}H_{17}N_2O_2$ (M+H+): 317.1298. Found 317.1285.

EXAMPLE XVII

Preparation of 2-(2,3-dihydroxypropyl)-6-methoxy-1-oxo-4-phenyl-1,2-dihydroisoquinoline-3-carbonitrile (89)

Compound 88 (261 mg, 0.83 mmol) was dissolved in 24 mL of acetone and 10 mL of water. OsO4 (Aldrich, 2.5% in 2-Me-2-propanol, 1.04 mL) was added then NMO (116 mg, 1 mmol). The resulting mixture was stir at RT overnight then diluted with 1:1 sat NaHCO$_3$/sat Na$_2$SO$_3$. It was partitioned between EtOAc and aq NaHCO$_3$, then the organic phase was washed once with brine. The combined aqueous phases were washed once with EtOAc. Drying (Na$_2$SO$_4$) and concentration gave the title compound 89 as a light brown solid.

HRMS (ES) exact mass calculated for $C_{22}H_{19}N_2O_2$ (M+H+): 351.1339. Found 351.1351.

HRMS (ES) exact mass calculated for $C_{18}H_{14}FN_2O_2$ (M+H+): 309.1034. Found 309.1028.

EXAMPLE XVII

Preparation of 2-[(2S)-2,3-dihydroxypropyl]-6-methoxy-1-oxo4-phenyl-1,2-dihydroisoquinoline-3-carbonitrile (90)

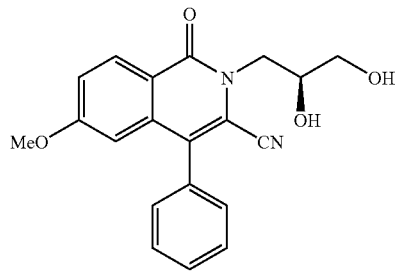

Compound 90, an enantiomer of compound 88 was prepared through resolution by passage through a chiral HPLC column.

EXAMPLE XIX

Preparation of 2-[(2R)-2,3-dihydroxypropyl]-6-methoxy-1-oxo-4-phenyl-1,2-dihydroisoquinoline-3-carbonitrile (91)

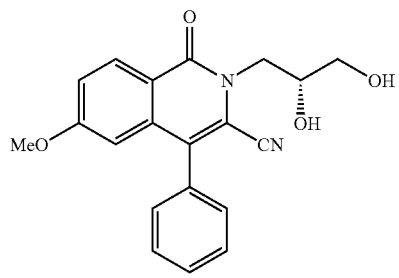

Compound 91, an enantiomer of compound 88 was prepared through resolution by passage through a chiral HPLC column.

EXAMPLE XX

Preparation of 2-(2-amino-3-hydroxypropyl)-6-methoxy-1-oxo-4-phenyl-1,2-dihydroisoquinoline-3-carbonitrile (95)

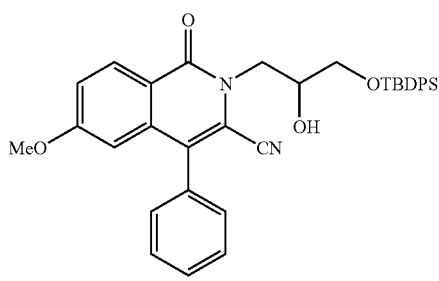

Step A: 2-(3-{[tert-butyl(diphenyl)silyl]oxy}-2-hydroxypropyl)-6-methoxy-1-oxo-4-phenyl-1-1,2-dihydroisoquinoline-3-carbonitrile (92)

To a suspension of diol 88 (100 mg, 0.29 mmol) in CH$_2$Cl$_2$ (1.5 mL) were added TBDPSCl (86 mg, 0.32 mmol), Et$_3$N (0.052 mL, 0.37 mmol), and DMAP (7 mg, 0.06 mmol). After stirring at RT overnight, the reaction mixture was quenched with sat NH$_4$Cl. It was then partitioned between NH$_4$Cl and EtOAc. The organic phase was washed with brine (1×), then dry (Na$_2$SO$_4$) and conc. The crude product was purified by automated flash chromatography 9:1 to 3:2 hexane/EtOAc to give 92.

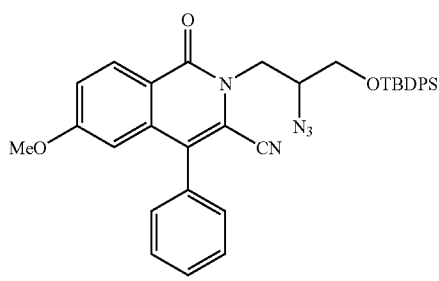

Step B: 2-(2-azido-3-{[tert-butyl(diphenyl)silyl]oxy}propyl)-6-methoxy-1-oxo-phenyl-1.2-dihydroisoquinoline-3-carbonitrile (93)

To a solution of alcohol 92 (117 mg, 0.2 mmol) in CH$_2$Cl$_2$ (4 mL) at 0 C was added MsCl (0.017 mL, 0.22 mmol), then Et$_3$N (0.042 mL, 0.3 mmol). After stirring for 4 h, the reaction was partitioned between CH$_2$Cl$_2$ and NaHCO$_3$. The aqueous phase was extracted once more with CH$_2$Cl$_2$ then the combined extracts were dried (MgSO$_4$). Filtration and concentration gave a residue which was dissolved in DMF (8 mL). Sodium azide (129 mg, 2 mmol) was added and the reaction mixture heated to 80 C for 2 h. It was cooled to RT, diluted with CH$_2$Cl$_2$ and filtered. Concentration and purification by automated flash chromatography 97:3 to 65:35 hexane/EtOAc gave the azide 93.

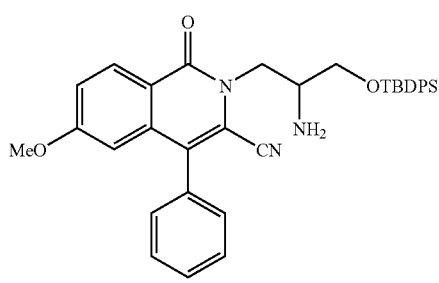

Step C: 2-(2-amino-3-{[tert-butyl(diphenyl)silyl]oxy}propyl)-6-methoxy-1-oxo-4-phenyl-1,2-dihydroisoquinoline-3-carbonitrile (94)

To a solution of azide 93 (39 mg, 0.064 mmol) in EtOAc (5 mL) was added a slurry of 25 mg of 10% Pd/C in EtOAc. The resulting mixture was hydrogenated at 45 psi overnight Filtration and concentration gave the amine 94.

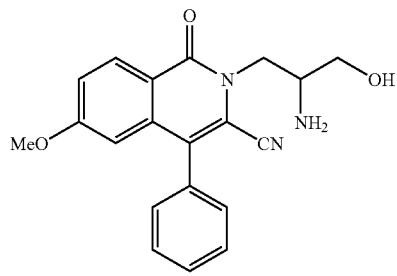

Step D: 2-(2-amino-3-hydroxypropyl)-6-methoxy-1-oxo-4-phenyl-1,2-dihydroisoquinoline-3-carbonitrile (95)

To a solution of 94 (37 mg, 0.063 mmol) in THF at room temperature was added 1M TBAY in THF (1.5 mL). After 2 h, the reaction mixture was partitioned between EtOAc and 1N HCl. The organic phase was washed once with 1N HCl. The combined aqueous phases were basified with NaOH, then extracted with CH$_2$Cl$_2$ (3×). Drying the organic phase (Na$_2$SO$_4$) and concentration gave a residue which was purified by high pressure flash chromatography (0-10% MeOH (NH$_3$)/EtOAc) to give 95.

HRMS (ES) exact mass calculated for C$_{20}$H$_{19}$N$_3$O$_3$ (M+H+): 350.1499. Found 350.1504.

EXAMPLE XXI

Preparation of 2-[2-(dimethylamino)-3-hydroxypropyl]-6-methoxy-1-oxo-4-phenyl-1,2-dihydroisoquinoline-3-carbonitrile (96)

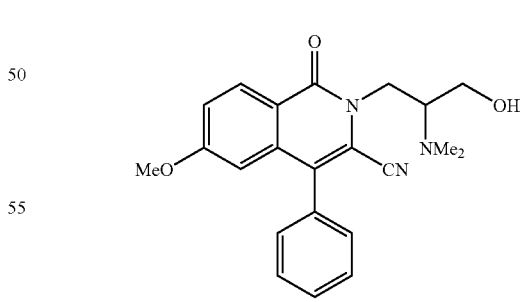

Amino alcohol 96 was prepared essentially according to the procedure described in Example XX for compound 95 by substituting dimethylamine for sodium azide in Step B and omitting Step C.

HRMS (ES) exact mass calculated for C$_{22}$H$_{23}$N$_3$O$_3$ (M+H+): 378.1812. Found 378.1802.

EXAMPLE XXII

Preparation of 2-(2-hydroxy-3-isopropoxypropyl)-6-methoxy-1-oxo-4-phenyl-1,2-dihydroisoquinoline-3-carbonitrile (98)

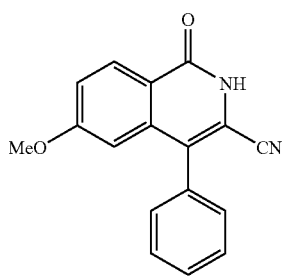

Step A: 6-methoxy-1-oxo-4-phenyl-1,2-dihydroisoquinoline-3-carbonitrile (97)

Allyl ether 88 (0.5 g, 1.6 mmol) was dissolved in dioxane (10 mL). Triethylamine (0.55 mL, 4 mmol) and formic acid (0.12 mL, 3.2 mmol) were added and the reaction mixture purged with argon. Pd(PPh$_3$)$_4$ (91 mg, 0.08 mmol) was added and the mixture heat to 100 C under a stream of Ar for 1.5 h. A precipitate formed upon cooling. It was isolated by filtration to give 97 as a white solid.

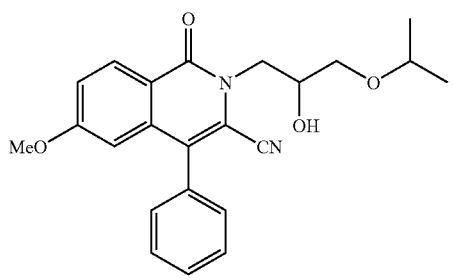

Step B: 2-(2-hydroxy-3-isopropoxypropyl)-6-methoxy-1-oxo-4-phenyl-1,2-dihydroisoquinoline-3-carbonitrile (98)

To a suspension of 97 (52 mg, 0.19 mmol) in iPrOH (3 mL) were added pyridine (0.03 mL, 0.38 mmol) and glycidyl isopropyl ether (0.047 mL, 0.38 mmol). The resulting mixture was heated to reflux overnight then cooled to room temperature. It was partitioned between EtOAc and NaHCO$_3$. The organic phase was washed with brine, dried (Na$_2$SO$_4$) and concentrated. The product 98 was purified by automated flash chromatography (20-50% EA/Hex).

HRMS (ES) exact mass calculated for C$_{23}$H$_{24}$N$_2$O$_4$ (M+H+): 393.1809. Found 393.1806.

EXAMPLE XXIII

Preparation of 2-[2-hydroxy-3-(1H-imidazol-1-yl)propyl]-6-methoxy-1-oxo-4-phenyl-1,2-dihydroisoquinoline-3-carbonitrile (100)

Step A: 6-methoxy-2-(oxiran-2-ylmethyl)-1-oxo-4-phenyl-1,2-dihydroiso-quinoline-3-carbonitrile (99

To a room temperature suspension of diol 89 (352 mg, 1 mmol) and PPTS (12 mg, 0.05 mmol) in CH$_2$Cl$_2$ (10 mL) was added trimethyl orthoacetate (0.153 mL, 1.2 mmol). A clear solution resulted within 2 minutes. After stirring at RT for 3.5 h the reaction mixture was concentrated. The residue was dissolved in CH$_2$Cl$_2$ (10 mL) and acetyl bromide (0.089 mL, 1.2 mmol) added. After stirring at RT for 1.5 h the reaction mixture was concentrated. The residue was taken up in 2 mL MeOH (2 mL) to give an orange-brown suspension. K$_2$CO$_3$ (153 mg, 1.1 mol) was added and the resulting mixture stirred at room temperature for 2 h. It was then partitioned between sat NH$_4$Cl and CH$_2$Cl$_2$. The aqueous phase was washed once more with CH$_2$Cl$_2$. The extracts were dried (MgSO$_4$) and concentrated. The product 99 was purified by automated flash chromatography (40-80% EA/Hex).

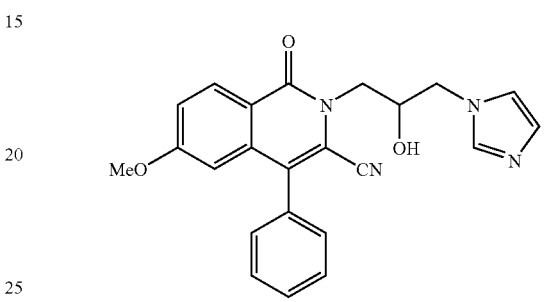

Step B: 2-[2-hydroxy-3-(1H-imidazol-1-yl)propyl]-6-methoxy-1-oxo-phenyl-1,2-dihydroisoquinoline-3-carbonitrile (100)

Imidazole (77 mg, 1.13 mmol) was added to a suspension of epoxide 99 (75 mg, 0.23 mmol) in iPrOH (2.5 mL) and the resulting mixture heated at reflux. A clear solution resulted within 10 minutes. After 2 h the reaction mixture was allowed to cool then partitioned between CH$_2$Cl$_2$ and NaHCO$_3$. The aqueous phase was extracted once with CH$_2$Cl$_2$. The combined organics were dried (Na$_2$SO$_4$) and concentrated. The product 100 was purified by automated flash chromatography (0-10% EA/Hex).

HRMS (ES) exact mass calculated for C$_{23}$H$_{20}$N$_4$O$_3$ (M+H+): 401.1608. Found 401.1608.

EXAMPLE XXIV

Preparation of 2-{3-hydroxy-2-[(pyridin-3-ylmethyl)amino]propyl}-6-methoxy-1-oxo-4-phenyl-1,2-dihydroisoquinoline-3-carbonitrile (102)

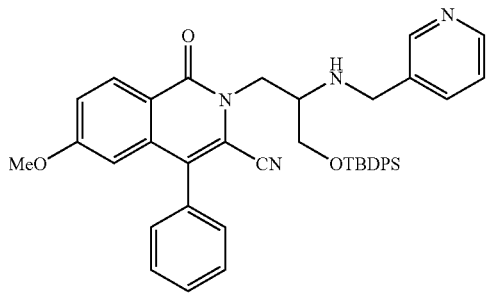

Step A: 2-{3-{[tert-butyl(diphenyl)silyl]oxy}-2-[(pyridin-3-ylmethyl)amino]-propyl}-6-methoxy-1-oxo4-phenyl-1,2-dihydroisoquinoline-3 carbonitrile (101)

To a solution of amine 94 (51 mg, 0.075 mmol) in dichloroethane (2 mL) was added pyridine 3-carboxaldehyde (0.017 mL, 180 mmol). After stirring at RT for 15 min NaBH(OAc)3 (48 mg, 0.23 mmol) was added. After stirring overnight, added 1.2 equiv aldehyde and 1.5 equiv NaBH(OAc)$_3$. After stirring for 5 h, the reaction mixture was diluted with NaHCO$_3$/EtOAc and stirred for 10 min. It was then partitioned between EtOAc and NaHCO$_3$. The organic phase was washed once with brine then dried (Na$_2$SO$_4$) and concentrated. The product was purified by automated flash chromatography (70-100% EtOAc/hexane).

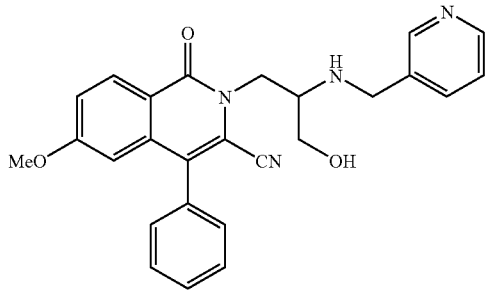

Step B: 2-{3-hydroxy-2-[(pyridin-3-ylmethyl)amino]propyl}-6-methoxy-1-oxo-4-phenyl-1,2-dihydroisoquinoline-3-carbonitrile (102)

TBAF (1M in THF, 0.15 mL, 0.15 mmol) was added to a solution of silyl ether 101 in THF (2.5 mL). After stirring for 2 h, the reaction mixture was partitioned between EtOAc and NaHCO$_3$. The organic phase was washed once with brine and then dried (Na$_2$SO$_4$) and concentrated. The product was purified by automated flash chromatography (0-8% MeOH (NH$_3$)/EtOAc).

HRMS (ES) exact mass calculated for C$_{26}$H$_{24}$N$_4$O$_3$ (M+H+): 441.1921. Found 441.1907.

EXAMPLE XXV

Preparation of 2-[3-hydroxy-2-(1H-1,2,3-triazol-1-yl)propyl]-6-methoxy-1-oxo-4-phenyl-1,2-dihydroisoquinoline-3-carbonitrile (104)

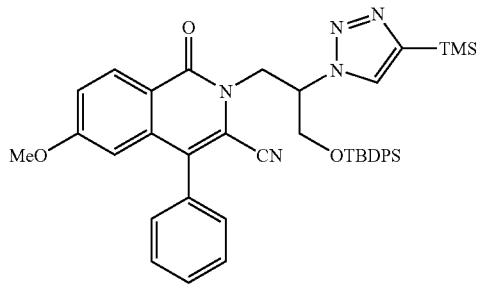

Step A: 2-{3-{[tert-butyl(diphenyl)silyl]oxy}-2-[4-trimethylsilyl)-1H-1,2,3-triazol-1-yl]propyl}-6-methoxy-1-oxo-phenyl-1,2-dihydroisoquinoline-3-carbonitrile (103)

TMS acetylene (0.27 mL, 1.9 mmol) was added to a solution of the azide 93 (118 mg, 0.19 mmol) in DMF (1 mL) and the resulting mixture heated overnight in a sealed tube in oil bath at 80° C. overnight. Concentration gave the product as a white solid.

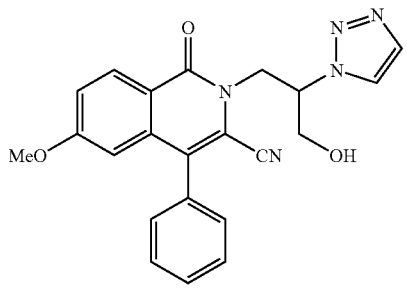

Step B: 2-[3-hydroxy-2-(1H-1,2,3-triazol-1-yl)propyl]-6-methoxy-1-oxo-phenyl-1,2-dihydroisoquinoline-3-carbonitrile (104)

To a solution of silyl ether 103 (144 mg, 0.2 mmol) in THF (5 mL) was added TBAF (1M in THF, 0.61 mL, 0.61 mmol) soln. After stirring at room temperature overnight O-desilylation had taken place. Added 6 uL of AcOH and continued stirring overnight at RT. The reaction mixture was diluted with MeOH and concentrated. The product was purified by automated flash chromatography (0-4% MeOH/EtOAc).

HRMS (ES) exact mass calculated for C$_{22}$H$_{19}$N$_5$O$_3$ (M+H+): 402.1561. Found 402.1563.

EXAMPLE XXVI

Preparation of 2-allyl-(3-fluorophenyl)-6-methoxy-1-oxo-1,2-dihydroisoquinoline-3-carbonitrile (105)

Compound 105 was prepared essentially according the procedure described in Example XIV, by replacing key reagents as appropriate. Proton NMR for the product was consistent with the titled compound.

EXAMPLE XXVII

Preparation of 2-(2,3-dihydroxypropyl)-4-(3-fluorophenyl)-6-methoxy-1-oxo-1,2-dihydroisoquinoline-3-carbonitrile (106)

Compound 106 was prepared essentially according the procedure described in Example XVII for compound 89.

EXAMPLE XXVIII

Preparation of 4-(3-fluorophenyl)-6-methoxy-1-oxo-2-(2-oxoethyl)-1,2-dihydroisoquinoline-3-carbonitrile (107)

A solution of sodium periodate (368 mg, 1.72 mmol) in water (7 mL) was added to a solution of diol 106 (0.96 mmol) in THF (15 mL) at 0° C. After 7 h an additional 1.8 equivalents of NaIO$_4$ were added. The reaction mixture was stirred overnight then partitioned between EtOAc and NaHCO$_3$. The aqueous phase was extracted with EtOAc and the combined extracts dried (MgSO$_4$). Concentration gave the desired product 107.

EXAMPLE XXIX

Preparation of 4-(3-fluorophenyl)-6-methoxy-2-(2-morpholin-4-ylethyl)-1-oxo-1,2-dihydroisoquinoline-3-carbonitrile (108)

Compound 108 was prepared essentially according the procedure described in Example I, Step H for compound 8 by using morpholine as the amine component of the reaction.

Compounds 109-122 (Table 5) were prepared essentially according to the procedure described above in Example I for the preparation of compound 8 by substituting an appropriate amine in Step H. While Example I, Step H describes a specific set of conditions for performing a reductive amination reaction it is understood that modifications of said protocol or the use of other standard protocols may be required to access any or all of compounds 109-122. Said modifications and alternate protocols would be well known to and executable by anyone reasonably skilled in the art.

TABLE 5

Data for Compounds 109-122

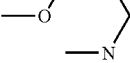

| Compound | Amino | HRMS Theoretical | HRMS (ES) Found |
|---|---|---|---|
| 109 | 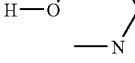 | 410.1874 | 410.1866 |
| 110 | 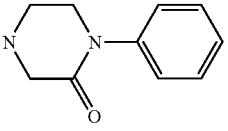 | 396.1718 | 396.1712 |
| 111 | 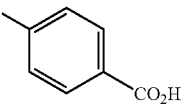 | 497.1984 | 497.1990 |
| 112 | 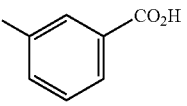 | 458.1511 | 458.1513 |
| 113 | 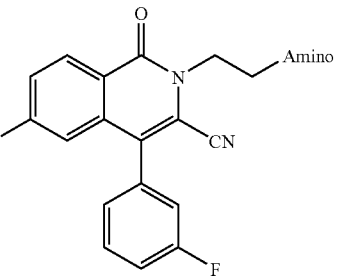 | 458.1511 | 458.1520 |

TABLE 5-continued

Data for Compounds 109-122

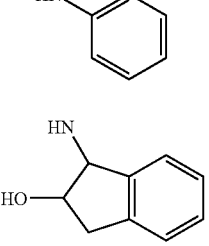

| Compound | Amino | HRMS Theoretical | HRMS (ES) Found |
|---|---|---|---|
| 114 | 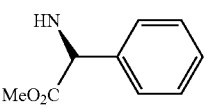 | 458.1511 | 458.1529 |
| 115 | 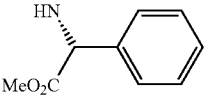 | 470.1875 | 470.1865 |
| 116 | 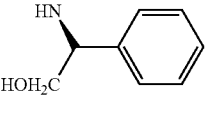 | 486.1824 | 486.1804 |
| 117 | 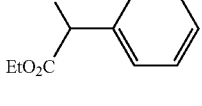 | 486.1824 | 486.1814 |
| 118 | 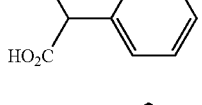 | 458.1875 | 458.1875 |
| 119 | 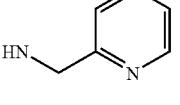 | 500.1980 | 500.1991 |
| 120 | 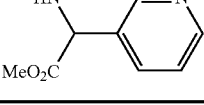 | 472.1667 | 472.1671 |
| 121 | 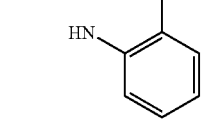 | 429.1721 | 429.1733 |
| 122 | 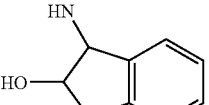 | 487.1776 | 487.1805 |

EXAMPLE XXX

Preparation of 6-methoxy-2-methyl-4-methylphenyl)-1-oxo-1,2-dihydroisoquinoline-3-carbonitrile (129)

Step A: 2-Hydroxy-4-methoxybenzoyl chloride (123)

To a solution of 2-hydroxy-p-anisic acid (0.2 g, 1.2 mmol) in DCE (8 mL) was added thionyl chloride (0.13 mL, 1.8 mmol) and a drop of DMF. After stirring at room temperature for 4.5 h the reaction mixture was concentrated and azeotroped several times with benzene to give the acid chloride 123 as a white solid (222 mg).

Step B: N-(Cyanomethyl)-2-hydroxy-4-methoxy-N-methylbenzamide (124)

To a solution of the acid chloride 123 (22.2 g, 119 mmol) in DCE (500 mL) were added N-methylacetonitrile (11 mL, 143 mmol) and 2,6-lutidine (21 mL, 178 mmol). The resulting mixture was stirred at room temperature overnight then diluted with EtOAc. The organic layer was washed with 1N HCl (3×) then brine. After drying over MgSO$_4$ it was concentrated to give the amide 124 (25 g).

Step C: 2-{[(Cyanomethyl)(methyl)amino]carbonyl}-5-methoxyphenyl trifluoromethanesulfonate (125)

To a solution of the phenol 124 (1.31 g, 5.9 mmol) in methanol (18 mL) was added Hunig's base (1.5 ml, 8.9 mmol). The reaction mixture was cooled to 0 C then N-phenyltriflimide (3.2 g, 8.9 mmol) was added. Stirring was conducted at room temperature overnight then the reaction mixture was concentrated and the residue purified by flash chromatography (10-0% EtOAc in hexanes). The product 125 was a colorless liquid (1.6 g).

Step D: Methyl 2-{[(cyanomethyl)(methyl)amino]carbonyl}-5-methoxybenzoate (126)

Carbon monoxide was bubbled for 5 minutes through a solution of the triflate 125 (1.6 g, 4.5 mmol) and triethylamine (1.4 mL, 10.3 mmol) in DMSO (30 mL) and MeOH (15 mL). Palladium acetate (60 mg, 0.27 mmol) and DPPF (296 mg, 0.54 mmol) were added then the reaction mixture was heated at 70 C overnight under an atmosphere of carbon monoxide maintained by a balloon. The reaction mixture was cooled and partitioned between EtOAc and water. The aqueous layer was extracted with EtOAc and the combined organics washed with half saturated brine. Drying (MgSO$_4$), concentration and flash chromatography (10-70% EtOAc in hexanes with 5% MeOH) gave the ester 126 (0.69 g).

Step E: 4-Hydroxy-6-methoxy-2-methyl-1-oxo-1,2-dihydroisoquinoline-3-carbonitrile (127)

NaOMe (4.4M in MeOH, 1.2 mL, 5.3 mmol) was added to a solution of the ester 126 (0.69 g, 2.6 mmol) in MeOH (20 mL). The resulting mixture was heated at reflux for 2 h. It was then cooled and concentrated. 1M HCl in ether (5.5 mL) was added and the mixture filtered and concentrated to give the product 127 as a tan solid (0.87 g).

Step F: 3-Cyano-6-methoxy-2-methyl-1-oxo-1,2-dihydroisoquinolin-4-yl trifluoromethanesulfonate (128)

Phenol 127 was converted to triflate 128 essentially as in Step C above.

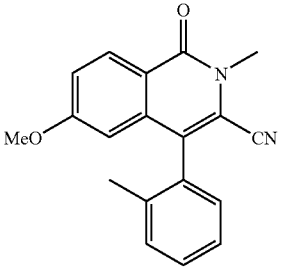

Step G: 6-Methoxy-2-methyl-4-(2-methylphenyl)-1-oxo-1,2-dihydroisoquinoline-3-carbonitrile (129)

A mixture of the triflate (100 mg, 0.276 mmol), Pd$_2$(dba)$_3$ (13 mg, 0.014 mmol), Cy$_3$P (8 mg, 0.028 mmol), O-methylbenzeneboronic acid (41 mg, 0.304 mmol) and cesium carbonate (108 mg, 0.331 mmol) in dioxane (1 mL) was heated in a sealed tube at 110 C overnight. The reaction mixture was filtered and concentrated. The residue was purified by automated flash chromatography to give the desired product 129.

HRMS (ES) for C$_{19}$H$_{16}$N$_2$O$_2$, Theoretical 305.1285, Found 305.1277

Compounds 130-142 (Table 6) were prepared essentially according to the procedure described above in Example XXXII for the preparation of compound 133 by substituting an appropriate boronic acid or ester in Step G. While Example XXX, Step G describes a specific set of conditions for performing a Suzuki reaction it is understood that modifications of said protocol or the use of other standard protocols may be required to access any or all of compounds 130-142. Said modifications and alternate protocols would be well known to and executable by anyone reasonably skilled in the art.

TABLE 6

Data for Compounds 130-142

| Compound | Aryl | HRMS Theoretical | HRMS (ES) Found |
|---|---|---|---|
| 130 | 4-Cl-C$_6$H$_4$ | 325.0739 | 325.0734 |
| 131 | 3-Cl-C$_6$H$_4$ | 325.0739 | 325.0733 |

TABLE 6-continued

Data for Compounds 130-142

[Structure: 6-methoxy-2-methyl-3-cyano-4-aryl-isoquinolin-1(2H)-one]

| Compound | Aryl | HRMS Theoretical | HRMS (ES) Found |
|---|---|---|---|
| 132 | 4-CF₃-phenyl | 359.1002 | 359.0994 |
| 133 | 4-OMe-phenyl | 321.1234 | 321.1228 |
| 134 | 3-CF₃-phenyl | 359.1002 | 359.0991 |
| 135 | 3-NH₂-phenyl | 306.1237 | 306.1233 |
| 136 | 3-methyl-phenyl | 305.1285 | 305.1276 |
| 137 | 3,5-dichloro-phenyl | 359.0349 | 359.0348 |
| 138 | 3-OMe-phenyl | 321.1234 | 321.1227 |
| 139 | 3-CN-phenyl | 316.1081 | 316.1085 |
| 140 | benzo[1,3]dioxol-5-yl | 335.1027 | 335.1020 |
| 141 | 4-(1H-pyrazol-3-yl)-phenyl | 281.1033 | 281.1033 |
| 142 | 4-(hydroxymethyl)-phenyl | 321.1234 | 321.1231 |

Using the methodologies described below, representative compounds of the invention were evaluated and found to exhibit activity in the Kv1.5 assays, thereby demonstrating and confirming the utility of the compounds of this invention as Kv1.5 inhibitors and antiarrhythmics. Compounds of this type may exhibit forward rate-dependence, blocking the outward K⁺ currents to a greater extent or preferentially at faster rates of depolarization or heart rates. Such a compound could be identified in electrophysiological studies as described below. For example, during a train of depolarizations delivered at frequencies of 1 Hz and 3 Hz, the block is "rate-dependent" if the amount of block observed during a 10 second train at 3 Hz is greater than that at 1 Hz. A Kv1.5 blocker may also display use-dependence, during which the block of the outward K⁺ currents increases with use, or during repetitive depolarization of a cardiac cell. Use dependence of block occurs to a greater extent with each successive depolarization in a train or sequence of pulses or depolarizations at a given rate or frequency. For example, during a train of 10 depolarizations at a frequency of 1 Hz, the block is "use-dependent" if the amount of block is greater for the $10^{th}$ pulse than for the $1^{st}$ pulse of the train. A Kv1.5 blocker may exhibit both use-dependence and rate-dependence.

A Kv1.5 blocker may also be identified through electro-physiological studies of native $I_{Kur}$ using cardiac myocytes or other tissue from various species including, but not limited to, human, rat, mouse, dog, monkey, ferret, rabbit, guinea pig, or goat. In native tissues Kv1.5 may exist as a homo-oligomer, or as a hetero-oligomer with other Kv family members, or may exist in a complex with a subunit. Compounds of this invention may block Kv1.5 homo- or hetero-oligomers or Kv1.5 in complexes with β-subunits.

Kv1.5 Assays

The high throughput Kv1.5 planar patch clamp assay is a systematic primary screen. It confirms activity and provides a functional measure of the potency of agents that specifically affect Kv1.5 potassium channels. Kiss et al. (Assay and Drug Dev. Tech., 1(1-2):127-135, 2003) and Schroeder et al. (J. of Biomol. Screen., 8(1);50-64, 2003) describe the use of this instrument for Kv1.5 as well as other voltage gated ion channels.

Chinese hamster ovary cells (CHO) stably expressing the human Kv1.5 potassium channel alpha subunit, cloned from human heart, are grown to 90-100% confluence in Ham's F12 medium supplemented with 10% FBS, 100 U/ml penicillin, 100 μg/ml streptomycin, 1000 μg/ml G-418 sulfate. Cells are subcultured by treatment with Versene, then suspended in phosphate-buffered saline (PBS) and centrifuged. The cell pellet is resuspended in PBS and the resulting suspension placed in the cell reservoir of the IonWorks™ HT instrument.

Electrophysiological recordings are performed with intracellular solution containing (mM): K-gluconate 100, KCl 40, $MgCl_2$ 3.2, EGTA 3, N-2-hydroxyethylpiperazine-$N^1$-2-ethanesulphonic acid (HEPES) 5, adjusted to pH 7.3. Amphotericin (Sigma) is prepared as 30 mg/ml stock solution and diluted to a final working concentration of 0.1 mg/ml in internal buffer solution. The external solution is Dulbecco's PBS (Invitrogen) and contains (mM): $CaCl_2$ 0.90, KCl 2.67, $KPO_4$ 1.47, $MgCl_2$ 0.50, NaCl 138, $NaPO_4$ 8.10 and has a pH of 7.4. All compounds are prepared as 10 mM stock solutions in DMSO. Compounds are diluted into external buffer, then transferred from the drug plate to the Patchplate during the experiment (final DMSO concentration <0.66% vol.).

Kv1.5 ionic currents are recorded at room temperature. Membrane currents are amplified (RMS~10 pA) and sampled at 10 kHz. Leak subtraction was performed in all experiments by applying a 160 ms hyperpolarizing (10 mV) pre-pulses 200 ms before the test pulses to measure leak conductance. The patch clamp stimulus protocol is as follows:

1. Patchplate wells are loaded with 3.5 μL of external buffer.
2. Planar micropipette hole resistances (Rp) is determined by applying a 10 mV, 160 ms potential difference across each hole (Hole test).
3. Cells are pipetted into the Patchplate and form high resistance seals with the 1-2 μm holes at the bottom of each Patchplate well. A seal test scan is performed to determine how many of the Patchplate wells have cells that have formed seals.
4. In order to gain electrical access to the cells, intracellular solution containing amphotericin is circulated for 4 minutes on the bottom side of the Patchplate.
5. Pre-compound addition test pulse is applied to each well on the Patchplate. Protocol: Cells are voltage clamped at a membrane holding potential of −80 mV for 15 seconds. This is followed by application of a 5 Hz stimulus train (27×150 ms depolarizations to +40 mV). The membrane potential steps to +40 mV evoke outward (positive) ionic currents.
6. Compound is added to each well of the Patchplate. Compounds are allowed to incubate for 5 minutes.
7. Post-compound addition test pulse protocol is applied. Protocol: Cells are voltage clamped at a membrane holding potential of −80 mV for 15 seconds. This is followed by application of a 5 Hz stimulus train (27×150 ms depolarizations to +40 mV).

Data analysis is conducted off-line. Paired comparisons between pre-drub and post-drug additions are used to determine the inhibitory effect of each compound. % inhibition of the peak control current during the $27^{th}$ depolarization to +40 mV (in the 5 Hz train) is plotted as a function of antagonist concentration. The concentrations of drug required to inhibit current by 50% ($IC_{50}$) are determined by fitting of the Hill equation to the concentration response data: % of Control=$100 \times (1+([Drug]/IC_{50})^p)^{-1}$ For each cell four arithmetic metrics are obtained:
1) seal resistance
2) baseline metric (the mean current at −70 mV from 5 to 45 ms before the first depolarization to +40 mV)
3) current run up metric (pre-compound mean current amplitude during the $1^{st}$ depolarization to +40 mV minus the pre-compound mean current amplitude during the $27^{th}$ depolarization to +40 mV)
4) peak current (maximum current amplitude during the $27^{th}$ depolarization to +40 mV during the 5 Hz train).

All metrics are obtained during both the pre- and post-compound addition traces. Cells are eliminated from further analysis if:
1) seal resistance is <50 MΩ
2) baseline metric is >±100 pA during the pre-compound
3) current run up metric is >−0.2 nA
4) pre-read peak metric is <400 pA.

The above-listed compounds provide ≧20% inhibition at a concentration of 33 μM or less in the high throughput Kv1.5 planar patch clamp assay described above. Data for specific compounds is shown below:

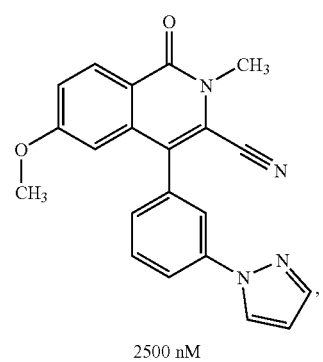

143

2500 nM

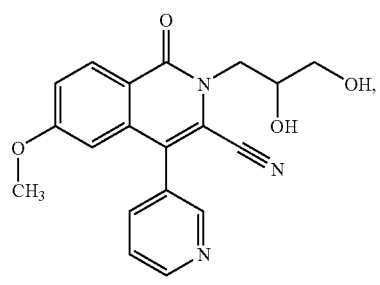

144

11000 nM

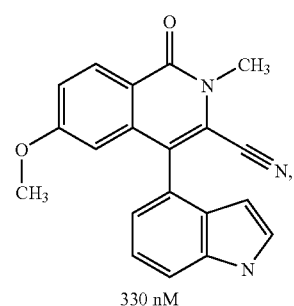

145

330 nM

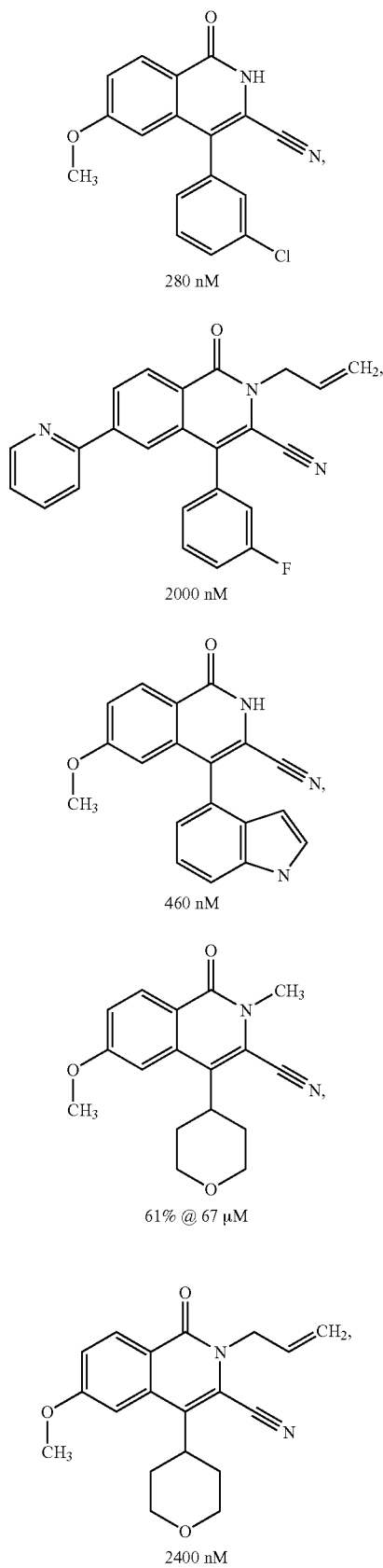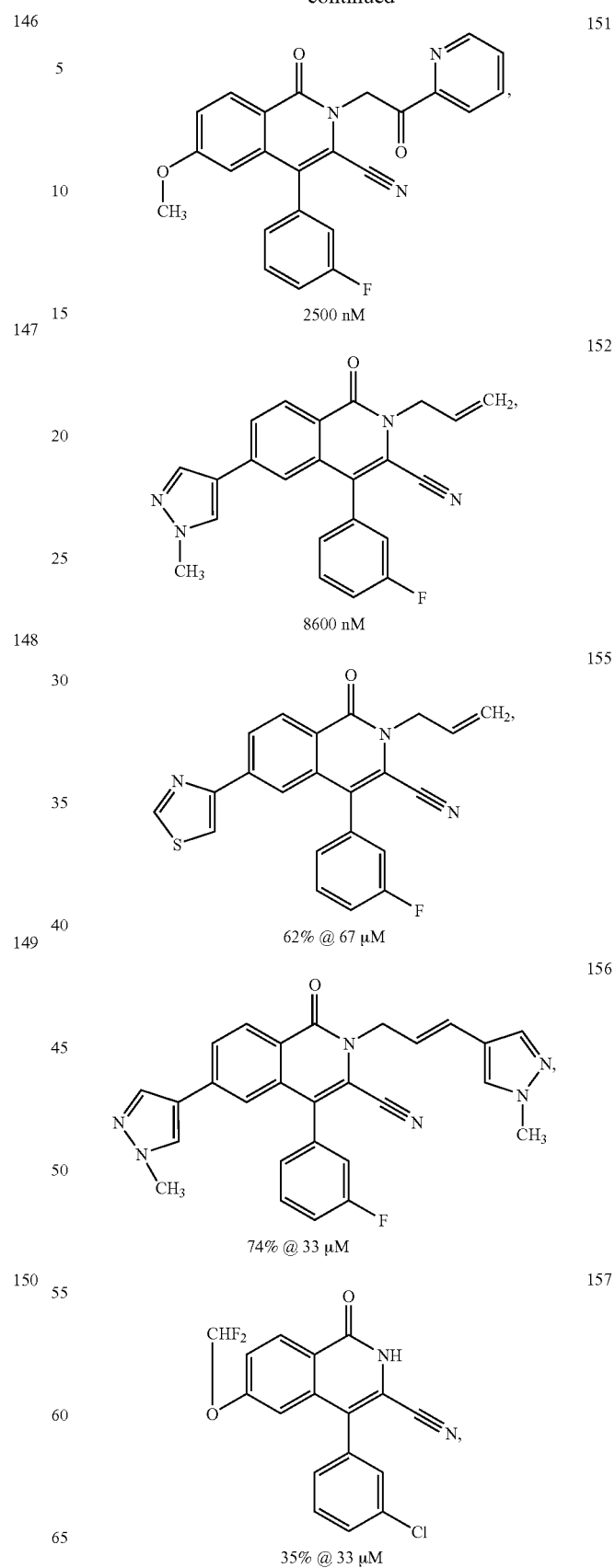

-continued

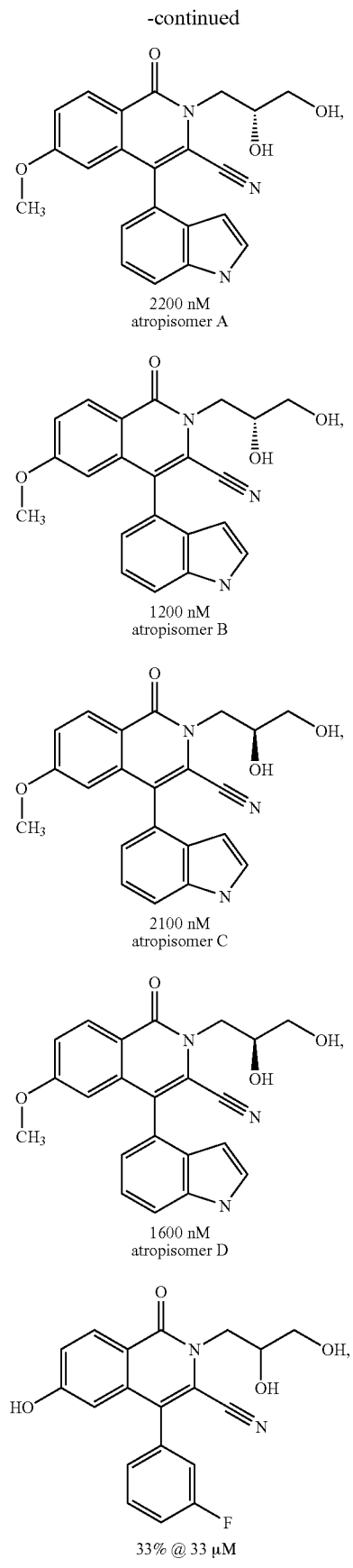

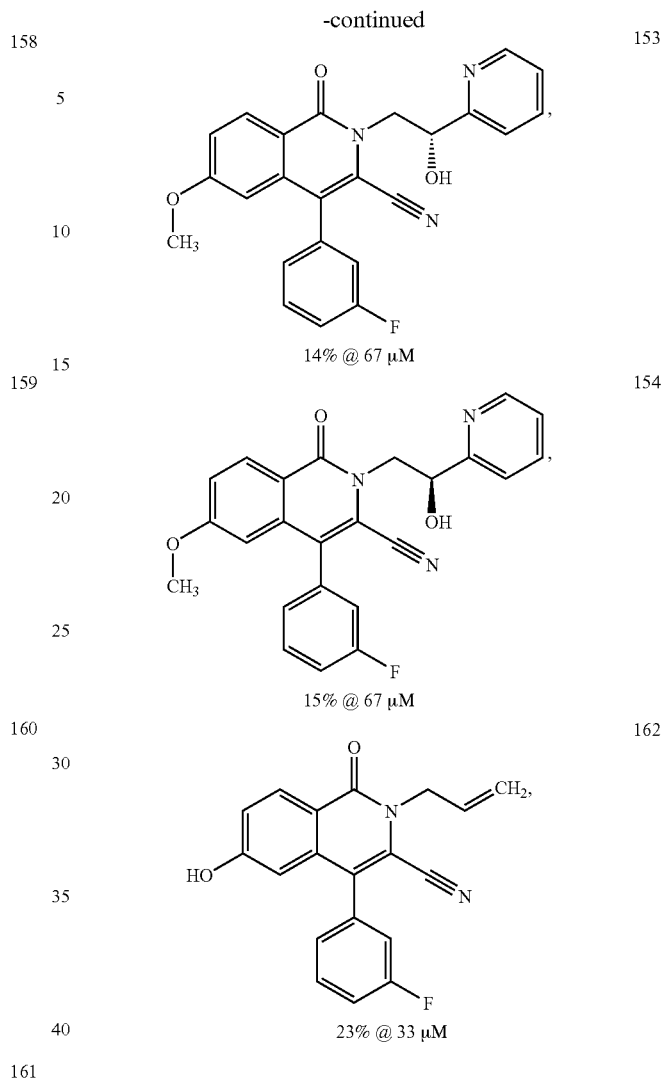

Compound Names:
6-methoxy-2-methyl-1-oxo-4-[3-(1H-pyrazol-1-yl)phenyl]-1,2-dihydroisoquinoline-3-carbonitrile (143),
2-(2,3-dihydroxypropyl)-6-methoxy-1-oxo-4-pyridin-3-yl-1,2-dihydroisoquinoline-3-carbonitrile (144),
4-(1H-indol-4-yl)-6-methoxy-2-methyl-1-oxo-1,2-dihydroisoquinoline-3-carbonitrile (145),
4-(3-chlorophenyl)-6-methoxy-1-oxo-1,2-dihydroisoquinoline-3-carbonitrile (146),
2-[2-allyl-3-cyano-4-(3-fluorophenyl)-1-oxo-1,2-dihydroisoquinoline-6-yl]pyridinium trifluoroacetate (147),
4-(1H-indol-4-yl)-6-methoxy-1-oxo-1,2-dihydroisoquinoline-3-carbonitrile (148),
6-methoxy-2-methyl-1-oxo-4-(tetrahydro-2h-pyran-(4-yl)-1,2-dihydroisoquinoline-3-carbonitrile (149),
2-allyl-6-methoxy-1-oxo-4-tetrahydro-2h-pyran-4-yl)-1,2-dihydroisoquinoline-3-carbonitrile (150),
4-3-fluorophenyl)-6-methoxy-1-oxo-2-(2-oxo-2-pyridin-2-ylethyl)-1,2-dihydroisoquinoline-3-carbonitrile (151),
2-allyl-4-(3-fluorophenyl)-6-(1-methyl-1H-pyrazol-1-yl)-1-oxo-1,2-dihydroisoquinoline-3-carbonitrile (152),
4-(3-fluorophenyl)-2-(2-hydroxy-2-pyridin-2-ylethyl)-6-methoxy-1-oxo-1,2-dihydroisoquinoline-3-carbonitrile (153), 4-(3-fluorophenyl)-2-(2-hydroxy-2-pyridin-2-ylethyl)-6-methoxy-1-oxo-1,2-dihydroisoquinoline-3-carbonitrile (154),
2-allyl-4-(3-fluorophenyl)-1-oxo-6-(1,3-thiazolyl)-1,2-dihydroisoquinoline-3-carbonitrile (155),
4-(3-fluorophenyl)-6-(1-methyl-1H-pyrazol-4-yl)-2-[(2E)-3-(1-methyl-1H-pyrazol-4-yl)prop-2-en-1-yl]-oxo-1,2-dihydroisoquinoline-3-carbonitrile (156),
4-3-chlorophenyl)-6-(difluoromethoxy)-1-oxo-1,2-dihydroisoquinoline-3-carbonitrile (157),
2-2,3-dihydroxypropyl)-4-(1H-indol-4-yl)-6-methoxy-1-oxo-1,2-dihydroisoquinoline-3-carbonitrile (158—atropisomer A),
2-(2,3-dihydroxypropyl)-4-(1H-indol-4-yl)-methoxy-1-oxo-1,2-dihydroisoquinoline-3-carbonitrile (159—atropisomer B),
2-(2,3-dihydroxypropyl)-4-(1H-indol-4-yl)-6-methoxy-1-oxo-1,2-dihydroisoquinoline-3-carbonitrile (160—atropisomer C),
2-(2,3-dihydroxypropyl)-4-(1H-indol-4-yl)-6-methoxy-1-oxo-1,2-dihydroisoquinoline-3-carbonitrile (161—atropisomer D),
2-allyl-4-(3-fluorophenyl)-6-hydroxy-2-oxo-1,2)-dihydroisoquinoline-3-carbonitrile (162),
2-(2,3-dihydroxypropyl)-4-(3-fluorophenyl)-6-hydroxy-1-oxo-1,2-dihydroisoquinoline-3-carbonitrile (163).

Atomic Absorption Spectroscopy Protocol:

This assay identifies agents that specifically block the human Kv1.5 K+ channel heterologously expressed in CHO cells as measured by $Rb^+$ efflux using Flame Atomic Absorption Spectroscopy (FAAS). The application of FAAS for measuring ion channel activity was adapted from Terstappen et al, *Anal. Biochem,* 272:149-155, 1999.

CHO cells expressing human Kv1.5 are cultured as described above, then harvested with trypsin-EDTA and washed with medium 1. 40,000 cells per well are seeded in a 96-well cell culture plate (assay plate) and the cells are allowed to grow for 48 hours at 37° C.
2. The medium is removed and 200 μl of Rb Load Buffer (Aurora Biomed, Vancouver, BC) is added for 3 hours at 37° C. under 5% $CO_2$.
3. The cells are washed 5 times with 200 μl Hank's Balanced Salt Solution (HBSS) followed by the addition of 100 μl HBSS containing test compound or 0.5% DMSO.
4. After 10 min, 100 μl of HEPES-buffered saline containing 140 mM KCl is added and plate is incubated at RT for 5 min. with gentle shaking.
5. Immediately thereafter, 150 μl of supernatant is transferred to a fresh 96 well plate and the remaining supernatant aspirated.
6. 120 μl of Cell Lysis Buffer (Aurora Biomed, Vancouver, BC) is added to the assay plate and shaken for 10 min. prior to analysis.
7. Rb content is measured in samples of supernatant (SUP) and lysate (LYS) using an ICR-8000 automated AAS instrument (Aurora Biomed, Vancouver, BC).

% FLUX=100%*(SUP/(LYS+SUP)). % INH=100%*(1-(A-B)/(C-B)), where A is % FLUX in the presence of tested compound, B is % FLUX in the presence of 10 mM (6-methoxy-2-methyl-1-oxo4-phenyl-1,2-dihydroisoquinolin-3-yl)-N,N-dimethylmethanaminium chloride, C is % FLUX in the presence of 0.25% DMSO.

The above-listed compounds provide ≧25% inhibition at a concentration of 25 μM or less in the AAS assay described above.

The compounds of this invention can be administered for the treatment or prevention of afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results. These dosages are the effective amounts for the treatment and prevention of afflictions, diseases and illnesses described above, e.g., cardiac arrhythmias such as atrial fibrillation, atrial flutter, atrial arrhythmia, and supraventricular tachycardia, thromboembolic events such as stroke and congestive heart failure, and immunodepression.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other antiarrhythmic agents having Kv1.5 blocking activities such as quinidine, propafenone, ambasilide, amiodarone, flecainide, sotalol, bretylium, dofetilide, almokalant, bepridil, clofilium, other compounds having Kv1.5 blocking activities such as clotrimazole, ketoconazole, bupivacaine, erythromycin, verapamil, nifedipine, zatebradine, bisindolylmaleimide, or other cardiovascular agents such as, but not limited to, ACE inhibitors such as benazepril, captopril, enalapril, fosinopril, lisinopril, moexipril, perindopril erbumine, quinapril, ramipril, and trandolapril, angiotensin II antagonists such as candesartan, eprosartan, irbesartan, losartan, olmesartan, telmisartan, and valsartan, cardiac glycosides such as digoxin, L-type calcium channel blockers, T-type calcium channel blockers, selective and nonselective beta blockers, an immunosuppressant compound, endothelin antagonists, thrombin inhibitors, aspirin, nonselective NSAIDs other than aspirin such as naproxen, warfarin, factor Xa inhibitors, low molecular weight heparin, unfractionated heparin, clopidogrel, ticlopidine, IIb/IIIa receptor antagonists such as tirofiban, 5HT receptor antagonists, integrin receptor antagonists, thromboxane receptor antagonists, TAFI inhibitors and P2T receptor antagonists. Compounds of the invention can also be administered as the sole active ingredient or in combination with a pacemaker or defibrillator device.

What is claimed is:

1. A compound of structural formula I:

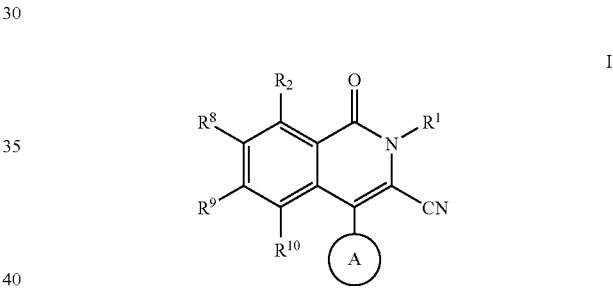

or a pharmaceutically acceptable salt, crystal form, or hydrate, wherein:

A is selected from the group consisting of

—$C_6H_5$,

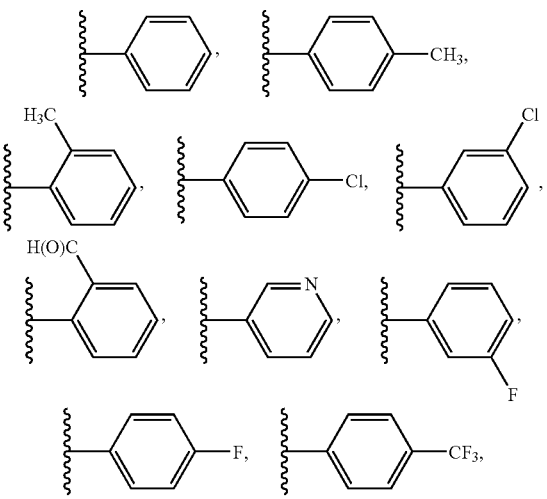

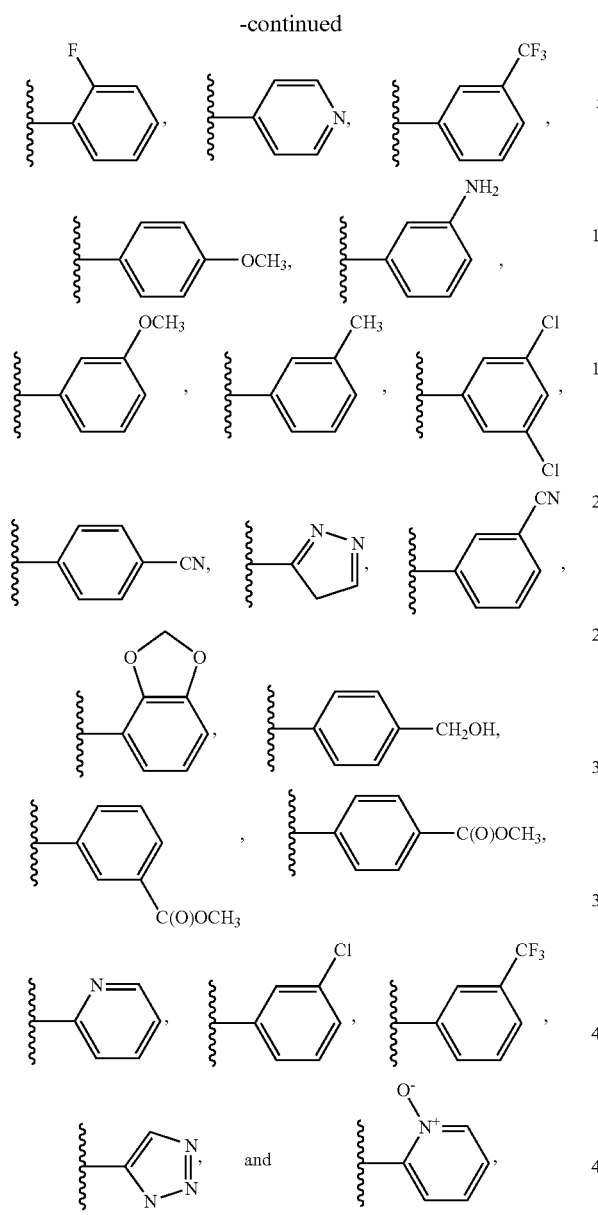

R[1] is selected from the group consisting of
—(CH$_2$)$_2$OH, —(CH$_2$)$_2$Cl, —CH$_3$, hydrogen, —(CH$_2$)$_2$N(CH$_3$)$_2$, —CH$_2$CH(OCH$_2$CH$_3$)$_2$, —(CH$_2$)$_3$CH$_3$, —(CH$_2$)$_2$NHC(CH$_3$)$_3$, —(CH$_2$)$_2$N(CH$_2$CH$_3$)$_2$, —(CH$_2$)$_2$NHCH(CH$_3$)$_2$, —(CH$_2$)$_2$NH(CH$_2$)C(CH$_3$)$_3$, —(CH$_2$)$_2$NH(CH$_2$)$_2$NHC(O)CH$_3$, —CH$_2$CH(OH)CH$_2$OH, c(C$_3$H$_5$), —CH$_2$CHCH$_2$, —(CH$_2$)$_2$N(CH$_3$)(CH$_2$)$_2$OCH$_3$, —(CH$_2$)$_2$N(CH$_3$)(CH$_2$)$_2$OH, —(CH$_2$)$_2$NH(CH$_2$)OCH$_3$, —CH$_2$CF$_3$, —CH$_2$CHCH$_2$, —(CH$_2$)$_2$OH, —(CH$_2$)$_2$NH(CH$_2$)$_2$OH, —(CH$_2$)$_3$OH, —CH$_2$CH(OH)CH$_2$N(CH$_3$)$_2$, —CH$_2$CH(NH$_2$)CH$_2$OH, —CH$_2$CH(N(CH$_3$)$_2$)CH$_2$OH, —CH$_2$CH(OH)CH$_2$OCH(CH$_3$)$_2$, —CH$_2$C(O)OCH$_2$CH$_3$, —CH$_2$CH(OH)CH$_2$OCH$_2$CH$_3$, —CH$_2$CH(OH)CH$_2$OCH$_3$, —CH$_2$CH(OH)CH$_2$CH$_3$, —CH$_2$CH(OH)CH$_3$, —CH$_2$C(OH)(CH$_2$)$_2$, —CH$_2$C(O)OH, —CH(CH$_3$)C(O)OCH$_3$,

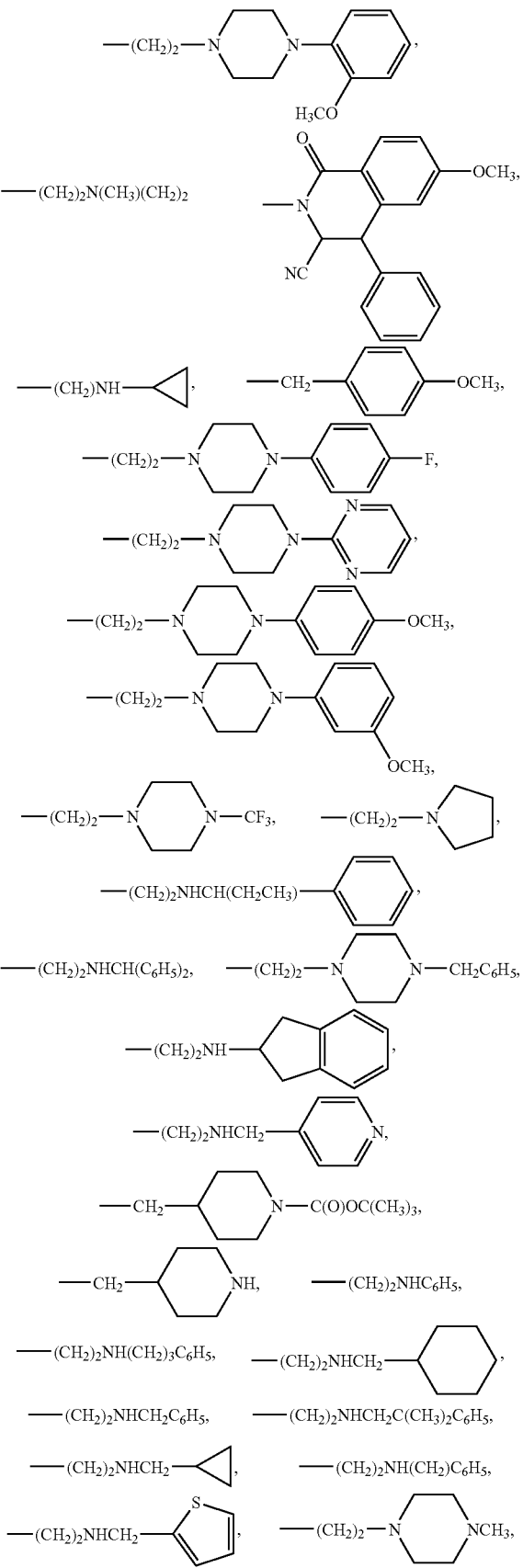

-continued

, ,

, ,

,

, ,

,

,

—(CH$_2$)$_2$NH——C(O)H,

—(CH$_2$)$_2$NH——C(O)OH,

,

, ,

—(CH$_2$)$_2$NHCH(C(O)OCH$_3$)C$_6$H$_5$, —(CH$_2$)$_2$NHCH(CH$_2$OH)C$_6$H$_5$,

—(CH$_2$)$_2$NHCH(C(O)OCH$_2$CH$_3$)C$_6$H$_5$,

—(CH$_2$)$_2$NHCH(C(O)OH)C$_6$H$_5$, ,

,

,

,

,

-continued

,

, and 

R$^2$ and R$^8$ are independently selected from:
1) hydrogen,
2) halogen,
3) NO$_2$,
4) CN,
5) CR$^{43}$=C(R$^{44}$R$^{45}$),
6) C≡CR$^{43}$,
7) (CR$^e$R$^f$)$_p$OR$^{43}$,
8) (CR$^e$R$^f$)$_p$N(R$^{43}$R$^{44}$),
9) (CR$^e$R$^f$)$_p$C(O)R$^{43}$,
10) (CR$^e$R$^f$)$_p$C(O)OR$^{43}$,
11) (CR$^e$R$^f$)$_p$R$^{43}$,
12) (CR$^e$R$^f$)$_p$S(O)$_{0-2}$R$^{60}$,
13) (CR$^e$R$^f$)$_p$S(O)$_{0-2}$N(R$^{43}$R$^{44}$),
14) OS(O)$_{0-2}$R$^{60}$,
15) N(R$^{43}$)C(O)R$^{44}$,
16) N(R$^{43}$)S(O)$_{0-2}$R$^{60}$,
17) (CR$^e$R$^f$)$_p$N(R$^{43}$)R$^{60}$,
18) (CR$^e$R$^f$)$_p$N(R$^{43}$)R$^{60}$OR$^{44}$,
19) (CR$^e$R$^f$)$_p$N(R$^{43}$)(CR$^g$R$^h$)$_q$C(O)N(R$^{44}$R$^{45}$),
20) N(R$^{43}$)(CR$^e$R$^f$)$_p$R$^{60}$,
21) N(R$^{43}$)(CR$^e$R$^f$)$_p$N(R$^{44}$R$^{45}$), and
22) (CR$^e$R$^f$)$_p$C(O)N(R$^{43}$R$^{44}$),
wherein one of R$^2$ and R$^8$ represents —OCH$_3$,
R$^a$, R$^b$, R$^c$, R$^d$, R$^e$, R$^f$, R$^g$, R$^h$, R$^i$, R$^j$, R$^k$ and R$^l$ are independently selected from the group consisting of:
1) hydrogen,
2) C$_1$-C$_6$ alkyl,
3) halogen,
4) aryl,
5) R$^{80}$,
6) C$_3$-C$_{10}$ cycloalkyl, and
7) OR$^4$,
said alkyl, aryl, and cycloalkyl being unsubstituted, monosubstituted with R$^7$, disubstituted with R$^7$ and R$^{15}$, trisubstituted with R$^7$, R$^{15}$ and R$^{16}$, or tetrasubstituted with R$^7$, R$^{15}$, R$^{16}$ and R$^{17}$;
R$^4$, R$^{40}$, R$^{41}$, R$^{42}$, R$^{43}$, R$^{44}$, R$^{45}$, R$^{46}$, R$^{47}$, R$^{48}$, R$^{49}$, R$^{51}$, and R$^{52}$ are independently selected from the group consisting of
1) hydrogen,
2) C$_1$-C$_6$ alkyl,
3) C$_3$-C$_{10}$ cycloalkyl,
4) aryl,
5) R$^{81}$,
6) CF$_3$,
7) C$_2$-C$_6$ alkenyl, and
8) C$_2$-C$_6$ alkynyl,
said alkyl, aryl, and cycloalkyl is unsubstituted, monosubstituted with R$^{18}$, di-substituted with R$^{18}$ and R$^{19}$, tri-substituted with $R^{18}$, $R^{19}$ and $R^{20}$, or tetra-substituted with $R^{18}$, $R^{19}$, $R^{20}$ and $R^{21}$;

$R^6$, $R^{60}$, $R^{61}$, and $R^{62}$ are independently selected from the group consisting of
1) $C_1$-$C_6$ alkyl,
2) aryl,
3) $R^{83}$, and
4) $C_3$-$C_{10}$ cycloalkyl;

said alkyl, aryl, and cycloalkyl is unsubstituted, mono-substituted with $R^{26}$, di-substituted with $R^{26}$ and $R^{27}$, tri-substituted with $R^{26}$, $R^{27}$ and $R^{28}$, or tetra-substituted with $R^{26}$, $R^{27}$, $R^{28}$ and $R^{29}$;

$R^7$, $R^{15}$, $R^{16}$, $R^{17}$, $R^{18}$, $R^{19}$, $R^{20}$, $R^{21}$, $R^{26}$, $R^{27}$, $R^{28}$, and $R^{29}$ are independently selected from the group consisting of
1) $C_1$-$C_6$ alkyl,
2) halogen,
3) $OR^{51}$,
4) $CF_3$,
5) aryl,
6) $C_3$-$C_{10}$ cycloalkyl,
7) $R^{84}$,
8) $S(O)_{0-2}N(R^{51}R^{52})$,
9) $C(O)OR^{51}$,
10) $C(O)R^{51}$,
11) CN,
12) $C(O)N(R^{51}R^{52})$,
13) $N(R^{51})C(O)R^{52}$,
14) $S(O)_{0-2}R^{62}$,
15) $NO_2$, and
16) $N(R^{51}R^{52})$;

wherein $R^{80}$, $R^{81}$, $R^{83}$, and $R^{84}$ are independently selected from the group of heterocyclic rings consisting of

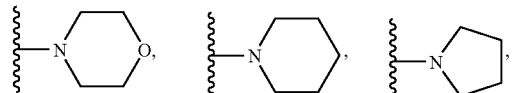
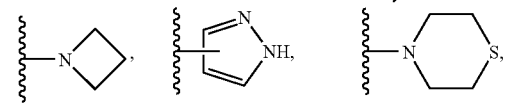
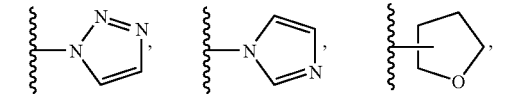
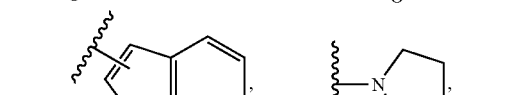
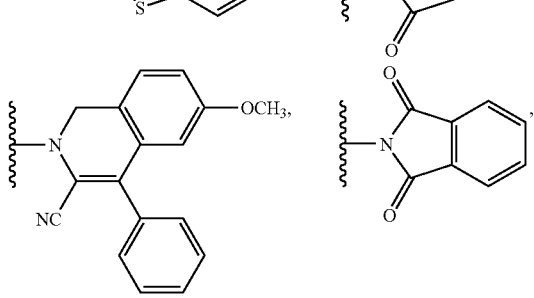

-continued

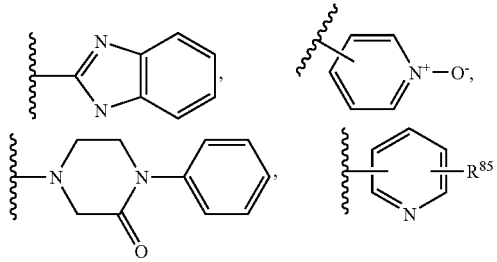

where $R^{85}$ is selected from the group consisting of hydrogen, $NH_2$, $NO_2$, and $CH_3$,

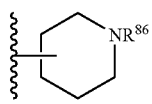

where $R^{86}$ is selected from the group consisting of hydrogen and —$C(O)OC(CH_3)_3$,

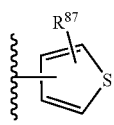

where $R^{87}$ is selected from the group consisting of hydrogen and $H_2OH$,

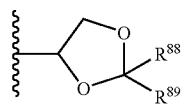

wherein $R^{88}$ and $R^{89}$ are independently selected from the group consisting of hydrogen, $CH_3$ and $CH_2CH_3$, and

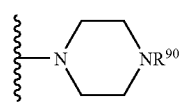

wherein $R^{90}$ is selected from the group consisting of hydrogen,

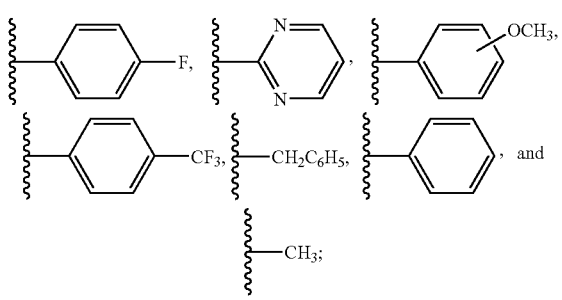

$R^9$ is selected from the group consisting of
—OCH$_3$, —CH$_3$, —CH$_2$CH$_3$, Cl, —SCH$_3$, I, Br, F, CF$_3$,
—O(CH$_2$)$_2$NH$_2$, —OCH$_2$C(O)OH, —CH$_2$NH$_2$, —CH(OH)CH$_3$, —OH, —OCH$_2$CF$_3$,
—OCH$_2$CHCH$_2$, —O(CH$_2$)$_2$OCH$_3$, —OCH$_2$CH(OH)CH$_2$OH, —CH(NH$_2$)CH$_3$, —OCH$_2$F,
—O(CH$_2$)$_2$CH$_3$, —O(CH$_2$)$_2$OCH$_2$CH$_3$, —OCH$_2$C(O)OCH$_2$CH$_3$, —O(CH$_2$)$_2$OH,
—O(CH$_2$)$_3$OH, —OCHF$_2$, —OCH$_2$C(O)N(CH$_3$)$_2$, —O(CH$_2$)$_3$C(O)OCH$_2$CH$_3$, O(CH$_2$)$_4$C(O)OCH$_2$CH$_3$,
—OCHCH$_2$, —O(CH$_2$)$_2$N(CH$_3$)$_2$, —O(CH$_2$)$_3$N(CH$_3$)$_2$,
—O(CH$_2$)$_6$NH$_2$, —C(CH$_2$)$_3$C(O)OH, —O(CH$_2$)$_4$C(O)OH, —O(CH$_2$)$_4$NH$_2$,
—O(CH$_2$)$_5$OC(O)CH$_3$, —OCH$_2$CN, —O(CH$_2$)$_5$OH,
—OC(O)CH$_3$, —OSO$_2$CH$_3$,
—OCH$_2$C(O)C(CH$_3$)$_3$,

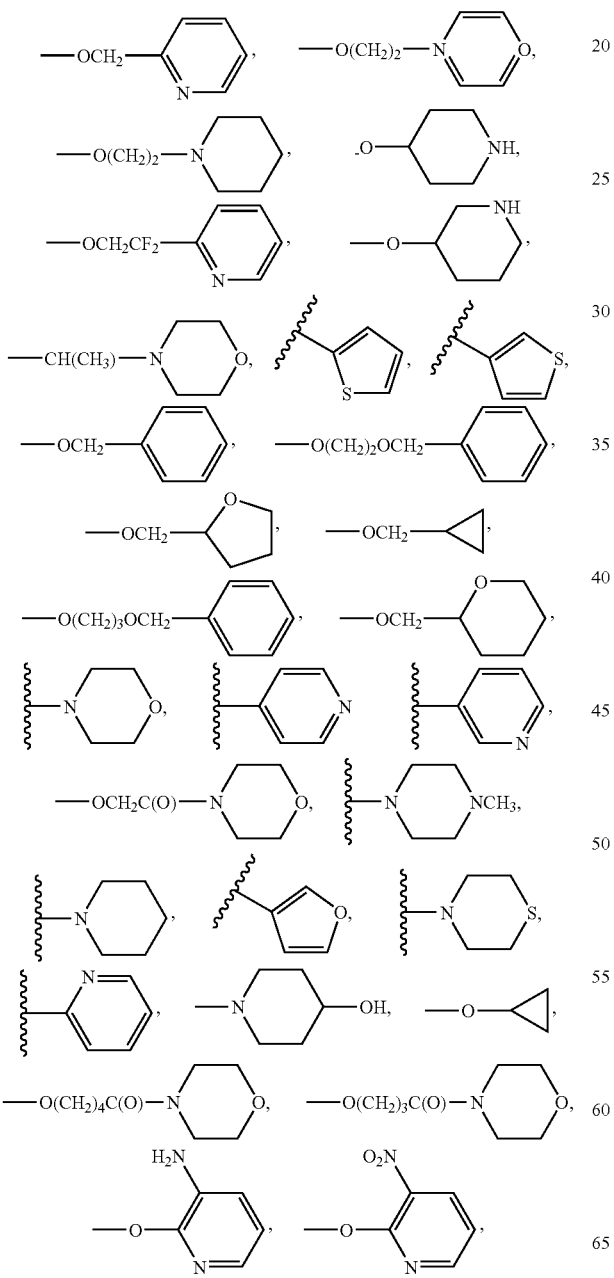

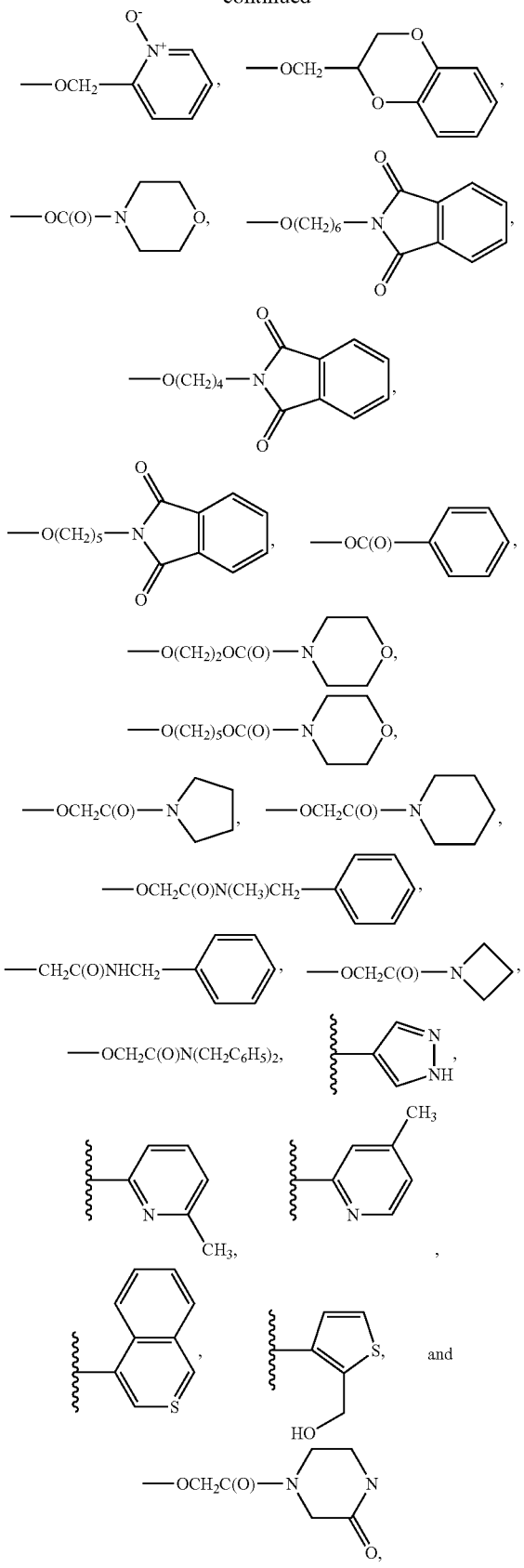

-continued and or $R^9$ and $R^{10}$, together with the atoms to which they are attached, form the ring,

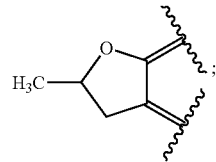

or a pharmaceutically acceptable salt thereof, wherein the compound is further selected from the group consisting of 6-methoxy-1-oxo-4-phenyl-2-[2-(5,6,7,8-tetrahydronaphthalen-1-ylamino)ethyl]-1,2-dihydroisoquinoline-3-carbonitrile,
2-(2-hydroxyethyl)-6-methoxy-1-oxo-4-phenyl-1,2-dihydroisoquinoline-3-carbonitrile,
2-(2-chloroethyl)-6-methoxy-1-oxo-4-phenyl-1,2-dihydroisoquinoline-3-carbonitrile,
2-[2-(cyclopropylamino)ethyl]-6-methoxy-1-oxo-4-phenyl-1,2-dihydroisoquinoline-3-carbonitrile,
6-methoxy-2-(4-methoxybenzyl)-1-oxo-4-phenyl-1,2-dihydroisoquinoline-3-carbonitrile,
2,6-dimethyl-1-oxo-4-phenyl-1,2-dihydroisoquinoline-3-carbonitrile,
6-ethyl-2-methyl-1-oxo-4-phenyl-1,2-dihydroisoquinoline-3-carbonitrile,
6-methoxy-1-oxo-4-phenyl-1,2-dihydroisoquinoline-3-carbonitrile,
2-[2-(dimethylamino)ethyl]-6-methoxy-1-oxo-4-phenyl-1,2-dihydroisoquinoline-3-carbonitrile,
6-methoxy-1-oxo-4-phenyl-2-[2-(4-pyrimidin-2-ylpiperazin-1-yl)ethyl]-1,2-dihydroisoquinoline-3-carbonitrile,
6-methoxy-2-{2-[4-(4-methoxyphenyl)piperazin-1-yl]ethyl}-1-oxo-4-phenyl-1,2-dihydroisoquinoline-3-carbonitrile,
6-methoxy-2-{2-[4-(3-methoxyphenyl)piperazin-1-yl]ethyl}-1-oxo-4-phenyl-1,2-dihydroisoquinoline-3-carbonitrile,
6-methoxy-2-{2-[4-(2-methoxyphenyl)piperazin-1-yl]ethyl}-1-oxo-4-phenyl-1,2-dihydroisoquinoline-3-carbonitrile,
2-{2-[4-(4-fluorophenyl)piperazin-1-yl]ethyl}-6-methoxy-1-oxo-4-phenyl-1,2-dihydroisoquinoline-3-carbonitrile,
6-methoxy-1-oxo-4-phenyl-2-(2-{4-[4-(trifluoromethyl)phenyl]piperazin-1-yl}ethyl)-1,2-dihydroisoquinoline-3-carbonitrile,
6-methoxy-2-methyl-1-oxo-4-phenyl-1,2-dihydroisoquinoline-3-carbonitrile,
2-(2,2-diethoxyethyl)-6-methoxy-1-oxo-4-phenyl-1,2-dihydroisoquinoline-3-carbonitrile,
6-methoxy-2-methyl-4-(4-methylphenyl)-1-oxo-1,2-dihydroisoquinoline-3-carbonitrile,
2-butyl-6-methoxy-1-oxo-4-phenyl-1,2-dihydroisoquinoline-3-carbonitrile,
tert-butyl[2-(3-cyano-6-methoxy-1-oxo-4-phenylisoquinolin-2(1H)-yl)ethyl]-carbamate,
6-methoxy-2-methyl-4-(2-methylphenyl)-1-oxo-1,2-dihydroisoquinoline-3-carbonitrile,
6-methoxy-2-methyl-4-(2-methylphenyl)-1-oxo-1,2-dihydroisoquinoline-3-carbonitrile,
4-(4-chlorophenyl)-6-methoxy-2-methyl-1-oxo-1,2-dihydroisoquinoline-3-carbonitrile,
4-(3-chlorophenyl)-6-methoxy-2-methyl-1-oxo-1,2-dihydroisoquinoline-3-carbonitrile,
4-(2-formylphenyl)-6-methoxy-2-methyl-1-oxo-1,2-dihydroisoquinoline-3-carbonitrile,
6-chloro-2-methyl-1-oxo-4-phenyl-1,2-dihydroisoquinoline-3-carbonitrile,
6-iodo-2-methyl-1-oxo-4-phenyl-1,2-dihydroisoquinoline-3-carbonitrile,
1-[2-(3-cyano-6-methoxy-1-oxo-4-phenylisoquinolin-2(1H)-yl)ethyl]pyrrolidinium trifluoroacetate,
N-[2-(3-cyano-6-methoxy-1-oxo-4-phenylisoquinolin-2(1H)-yl)ethyl]-2-phenylbutan-1-aminium trifluoroacetate,
N-[2-(3-cyano-6-methoxy-1-oxo-4-phenylisoquinolin-2(1H)-yl)ethyl]-2,2-diphenylethanaminium trifluoroacetate,
2-[2-(4-benzylpiperazin-1-yl)ethyl]-6-methoxy-1-oxo-4-phenyl-1,2-dihydroisoquinoline-3-carbonitrile,
N-[2-(3-cyano-6-methoxy-1-oxo-4-phenylisoquinolin-2(1H)-yl)ethyl]indan-2-aminium trifluoroacetate,
N-{[1-(4-chlorophenyl)cyclopropyl]methyl}-2-(3-cyano-6-methoxy-1-oxo-4-phenylisoquinolin-2(1H)-yl)ethanaminium trifluoroacetate,
6-methoxy-1-oxo-4-phenyl-2-{2-[(pyridin-4-ylmethyl)amino]ethyl}-1,2-dihydroisoquinoline-3-carbonitrile,
tert-butyl 4-[(3-cyano-6-methoxy-1-oxo-4-phenylisoquinolin-2(1H)-yl)methyl]-piperidine-1-carboxylate,
6-bromo-2-methyl-1-oxo-4-phenyl-1,2-dihydroisoquinoline-3-carbonitrile,
N-(3-cyano-2-methyl-1-oxo-4-phenyl-1,2-dihydroisoquinolin-6-yl)-N-hydroxyacetamide,
N-(3-cyano-2-methyl-1-oxo-4-phenyl-1,2-dihydroisoquinolin-6-yl)-N-[(methylsulfonyl)oxy]methanesulfonamide,
4-[(3-cyano-6-methoxy-1-oxo-4-phenylisoquinolin-2(1H)-yl)methyl]piperidinium chloride,
6-fluoro-2-methyl-1-oxo-4-phenyl-1,2-dihydroisoquinoline-3-carbonitrile,
N-[2-(3-cyano-6-methoxy-1-oxo-4-phenylisoquinolin-2(1H)-yl)ethyl]benzenaminium trifluoroacetate,
N-[2-(3-cyano-6-methoxy-1-oxo-4-phenylisoquinolin-2(1H)-yl)ethyl]-4-phenylbutan-1-aminium trifluoroacetate,
N-[2-(3-cyano-6-methoxy-1-oxo-4-phenylisoquinolin-2(1H)-yl)ethyl]-3-phenylpropan-1-aminium trifluoroacetate,
N-[2-(3-cyano-6-methoxy-1-oxo-4-phenylisoquinolin-2(1H)-yl)ethyl]-2-methylpropan-2-aminium trifluoroacetate,
2-(3-cyano-6-methoxy-1-oxo-4-phenylisoquinolin-2(1H)-yl)-N-(cyclohexylmethyl)-ethanaminium trifluoroacetate,
(1S)-N-[2-(3-cyano-6-methoxy-1-oxo-4-phenylisoquinolin-2(1H)-yl)ethyl]-1-phenylethanaminium trifluoroacetate,
6-methoxy-1-oxo-4-phenyl-2-[2-(4-phenylpiperazin-1-yl)ethyl]-1,2-dihydroisoquinoline-3-carbonitrile,
1-[2-(3-cyano-6-methoxy-1-oxo-4-phenylisoquinolin-2(1H)-yl)ethyl]piperidinium trifluoroacetate,
2-(3-cyano-6-methoxy-1-oxo-4-phenylisoquinolin-2(1H)-yl)-N-(diphenylmethyl)-ethanaminium trifluoroacetate, 2-(3-cyano-6-methoxy-1-oxo-4-phenylisoquinolin-2(1H)-yl)-N-[2-(3-cyano-6-methoxy-1-oxo-4-phenyl-isoquinolin-2(1H)-yl)ethyl]-N-methylethanaminium trifluoroacetate,
2-(3-cyano-6-methoxy-1-oxo-4-phenylisoquinolin-2(1H)-yl)-N,N-diethylethanaminium trifluoroacetate,
N-benzyl-2-(3-cyano-6-methoxy-1-oxo-4-phenylisoquinolin-2(1H)-yl)ethanaminium trifluoroacetate,
2-(3-cyano-6-methoxy-1-oxo-4-phenylisoquinolin-2(1H)-yl)-N-[(trans-4-{[(methylamino)-carbonyl]oxy}-1-phenylcyclohexyl)methyl]ethanaminium trifluoroacetate,
N-[2-(3-cyano-6-methoxy-1-oxo-4-phenylisoquinolin-2(1H)-yl)ethyl]-2-methyl-2-phenylpropan-1-aminium trifluoroacetate,
2-[2-(3-cyano-6-methoxy-1-oxo-4-phenylisoquinolin-2(1H)-yl)ethyl]-1,2,3,4-tetrahydroisoquinolinium trifluoroacetate,
2-(3-cyano-6-methoxy-1-oxo-4-phenylisoquinolin-2(1H)-yl)-N-(2-thienylmethyl)-ethanaminium trifluoroacetate,
N-[2-(3-cyano-6-methoxy-1-oxo-4-phenylisoquinolin-2(1H)-yl)ethyl]indan-1-aminium trifluoroacetate,
6-methoxy-2-[2-(4-methylpiperazin-1-yl)ethyl]-1-oxo-4-phenyl-1,2-dihydroisoquinoline-3-carbonitrile,
4-[2-(3-cyano-6-methoxy-1-oxo-4-phenylisoquinolin-2(1H)-yl)ethyl]morpholin-4-ium trifluoroacetate,
N-[2-(3-cyano-6-methoxy-1-oxo-4-phenylisoquinolin-2(1H)-yl)ethyl]propan-2-aminium trifluoroacetate,
N-[2-(3-cyano-6-methoxy-1-oxo-4-phenylisoquinolin-2(1H)-yl)ethyl]cyclohexanaminium trifluoroacetate,
2-(3-cyano-6-methoxy-1-oxo-4-phenylisoquinolin-2(1H)-yl)-N-(cyclopropylmethyl)-ethanaminium trifluoroacetate,
N-[2-(3-cyano-6-methoxy-1-oxo-4-phenylisoquinolin-2(1H)-yl)ethyl]-N-methylcyclohexanaminium trifluoroacetate,
2-(3-cyano-6-methoxy-1-oxo-4-phenylisoquinolin-2(1H)-yl)-N-(2-phenylethyl)-ethanaminium trifluoroacetate,
N-[2-(3-cyano-6-methoxy-1-oxo-4-phenylisoquinolin-2(1H)-yl)ethyl]pyridin-2-aminium trifluoroacetate,
(1R)-N-[2-(3-cyano-6-methoxy-1-oxo-4-phenylisoquinolin-2(1H)-yl)ethyl]-1-phenylethanaminium trifluoroacetate,
6-methoxy-1-oxo-4-phenyl-2-{2-[(pyridin-3-ylmethyl)amino]ethyl}-1,2-dihydroisoquinoline-3-carbonitrile,
2-(2-{[3-(1H-imidazol-1-yl)propyl]amino}ethyl)-6-methoxy-1-oxo-4-phenyl-1,2-dihydroisoquinoline-3-carbonitrile,
N-[2-(3-cyano-6-methoxy-1-oxo-4-phenylisoquinolin-2(1H)-yl)ethyl]-3-(2-oxopyrrolidin-1-yl)propan-1-aminium trifluoroacetate,
N-[2-(3-cyano-6-methoxy-1-oxo-4-phenylisoquinolin-2(1H)-yl)ethyl]-3,3-dimethylbutan-1-aminium trifluoroacetate,
2-(acetylamino)-N-[2-(3-cyano-6-methoxy-1-oxo-4-phenylisoquinolin-2(1H)-yl)-ethyl]ethanaminium trifluoroacetate,
6-methoxy-2-methyl-1-oxo-4-pyridin-4-yl-1,2-dihydroisoquinoline-3-carbonitrile,
6-methoxy-2-methyl-1-oxo-4-pyridin-3-yl-1,2-dihydroisoquinoline-3-carbonitrile,
5-methoxy-2-methyl-1-oxo-4-phenyl-1,2-dihydroisoquinoline-3-carbonitrile,
N-(3-cyano-2-methyl-1-oxo-4-phenyl-1,2-dihydroisoquinolin-6-yl)acetamide,
N-(3-cyano-2-methyl-1-oxo-4-phenyl-1,2-dihydroisoquinolin-6-yl)methanesulfonamide,
2-methyl-1-oxo-4-phenyl-6-(trifluoromethyl)-1,2-dihydroisoquinoline-3-carbonitrile,
2-(2,3-dihydroxypropyl)-6-methoxy-1-oxo-4-phenyl-1,2-dihydroisoquinoline-3-carbonitrile,
7-methoxy-2-methyl-1-oxo-4-phenyl-1,2-dihydroisoquinoline-3-carbonitrile,
4-(3-fluorophenyl)-6-methoxy-2-methyl-1-oxo-1,2-dihydroisoquinoline-3-carbonitrile,
2-methyl-7-nitro-1-oxo-4-phenyl-1,2-dihydroisoquinoline-3-carbonitrile,
2-cyclopropyl-4-(3-fluorophenyl)-6-methoxy-1-oxo-1,2-dihydroisoquinoline-3-carbonitrile,
6-(2-aminoethoxy)-2-methyl-1-oxo-4-phenyl-1,2-dihydroisoquinoline-3-carbonitrile,
[(3-cyano-2-methyl-1-oxo-4-phenyl-1,2-dihydroisoquinolin-6-yl)oxy]acetic acid,
2[(ammoniooxy)methyl]-1-chloro-3-fluorobenzene chloride,
2-allyl-4-(3-fluorophenyl)-6-methoxy-1-oxo-1,2-dihydroisoquinoline-3-carbonitrile,
2-(2,3-dihydroxypropyl)-4-(3-fluorophenyl)-6-methoxy-1-oxo-1,2-dihydroisoquinoline-3-carbonitrile,
4-(3-fluorophenyl)-6-methoxy-2-(2-morpholin-4-ylethyl)-1-oxo-1,2-dihydroisoquinoline-3-carbonitrile,
4-(3-fluorophenyl)-6-methoxy-2-{2-[(2-methoxyethyl)(methyl)-amino]ethyl}-1-oxo-1,2-dihydroisoquinoline-3-carbonitrile,
2,5-dimethyl-1-oxo-4-phenyl-1,2-dihydroisoquinoline-3-carbonitrile,
4-(3-fluorophenyl)-2-{2-[(2-hydroxyethyl)(methyl)amino]ethyl}-6-methoxy-1-oxo-1,2-dihydroisoquinoline-3-carbonitrile,
4-(3-fluorophenyl)-6-methoxy-2-{2-[(2-methoxyethyl)amino]ethyl}-1-oxo-1,2-dihydroisoquinoline-3-carbonitrile,
2-methyl-1-oxo-4-phenyl-6-(pyridin-2-ylmethoxy)-1,2-dihydroisoquinoline-3-carbonitrile,
2-methyl-6-(2-morpholin-4-ylethoxy)-1-oxo-4-phenyl-1,2-dihydroisoquinoline-3-carbonitrile,
2-methyl-1-oxo-4-phenyl-6-(2-piperidin-1-ylethoxy)-1,2-dihydroisoquinoline-3-carbonitrile,
6-acetyl-2-methyl-1-oxo-4-phenyl-1,2-dihydroisoquinoline-3-carbonitrile,
6-(1-hydroxyethyl)-2-methyl-1-oxo-4-phenyl-1,2-dihydroisoquinoline-3-carbonitrile,
2-methyl-1-oxo-4-phenyl-6-(piperidin-4-yloxy)-1,2-dihydroisoquinoline-3-carbonitrile,
6-(2,2-difluoro-2-pyridin-2-ylethoxy)-2-methyl-1-oxo-4-phenyl-1,2-dihydroisoquinoline-3-carbonitrile,
2-cyclopropyl-4-(3-fluorophenyl)-6-hydroxy-1-oxo-1,2-dihydroisoquinoline-3-carbonitrile,
2-methyl-1-oxo-4-phenyl-6-(pyrrolidin-3-yloxy)-1,2-dihydroisoquinoline-3-carbonitrile,
4-(3-fluorophenyl)-6-methoxy-1-oxo-2-(2,2,2-trifluoroethyl)-1,2-dihydroisoquinoline-3-carbonitrile,
4-(4-fluorophenyl)-6-methoxy-2-methyl-1-oxo-1,2-dihydroisoquinoline-3-carbonitrile,
5,7-dibromo-4-(3-fluorophenyl)-6-hydroxy-2-methyl-1-oxo-1,2-dihydroisoquinoline-3-carbonitrile,
5,7-dibromo-2-cyclopropyl-4-(3-fluorophenyl)-6-hydroxy-1-oxo-1,2-dihydroisoquinoline-3-carbonitrile,
5-bromo-2-cyclopropyl-4-(3-fluorophenyl)-6-hydroxy-1-oxo-1,2-dihydroisoquinoline-3-carbonitrile,
2-cyclopropyl-4-(3-fluorophenyl)-1-oxo-6-(2,2,2-trifluoroethoxy)-1,2-dihydroisoquinoline-3-carbonitrile, 2-methyl-6-(1-morpholin-4-ylethyl)-1-oxo-4-phenyl-1,2-dihydroisoquinoline-3-carbonitrile,
2-methyl-6-[(1-oxidopyridin-2-yl)methoxy]-1-oxo-4-phenyl-1,2-dihydroisoquinoline-3-carbonitrile,
6-(allyloxy)-2-cyclopropyl-4-(3-fluorophenyl)-1-oxo-1,2-dihydroisoquinoline-3-carbonitrile,
2-cyclopropyl-4-(3-fluorophenyl)-6-(2-methoxyethoxy)-1-oxo-1,2-dihydroisoquinoline-3-carbonitrile,
6-methoxy-2-methyl-1-oxo-4-[4-(trifluoromethyl)phenyl]-1,2-dihydroisoquinoline-3-carbonitrile,
2(2,3-dihydroxypropyl)-4-(3-fluorophenyl)-6-methoxy-1-oxo-1,2-dihydroisoquinoline- 3-carbonitrile,
2-(2,3-dihydroxypropyl)-4-(3-fluorophenyl)-6-methoxy-1-oxo-1,2-dihydroisoquinoline-3-carbonitrile,
2-cyclopropyl-6-(2,3-dihydroxypropoxy)-4-(3-fluorophenyl)-1-oxo-1,2-dihydroisoquinoline-3-carbonitrile,
2-cyclopropyl-6-ethoxy-4-(3-fluorophenyl)-1-oxo-1,2-dihydroisoquinoline-3-carbonitrile,
2-allyl-6-methoxy-1-oxo-4-phenyl-1,2-dihydroisoquinoline-3-carbonitrile,
1-(3-cyano-2-methyl-1-oxo-4-phenyl-1,2-dihydroisoquinolin-6-yl)ethanaminium trifluoroacetate,
5-bromo-6-methoxy-2-methyl-1-oxo-4-phenyl-1,2-dihydroisoquinoline-3-carbonitrile,
7-bromo-6-methoxy-2-methyl-1-oxo-4-phenyl-1,2-dihydroisoquinoline-3-carbonitrile,
2-methyl-1-oxo-4-phenyl-6-thien-2-yl-1,2-dihydroisoquinoline-3-carbonitrile,
2-cyclopropyl-6-(fluoromethoxy)-4-(3-fluorophenyl)-1-oxo-1,2-dihydroisoquinoline-3-carbonitrile,
2-methyl-1-oxo-4-phenyl-6-thien-3-yl-1,2-dihydroisoquinoline-3-carbonitrile,
4-(3-fluorophenyl)-2-(2-hydroxyethyl)-6-methoxy-1-oxo-1,2-dihydroisoquinoline-3-carbonitrile,
4-(3-fluorophenyl)-2-{2-[(2-hydroxyethyl)amino]ethyl}-6-methoxy-1-oxo-1,2-dihydroisoquinoline-3-carbonitrile,
2-[(2s)-2,3-dihydroxypropyl]-6-methoxy-1-oxo-4-phenyl-1,2-dihydroisoquinoline-3-carbonitrile,
2-[(2r)-2,3-dihydroxypropyl]-6-methoxy-1-oxo-4-phenyl-1,2-dihydroisoquinoline-3-carbonitrile,
4-(2-fluorophenyl)-6-methoxy-2-methyl-1-oxo-1,2-dihydroisoquinoline-3-carbonitrile,
2-allyl-4-(2-fluorophenyl)-6-methoxy-1-oxo-1,2-dihydroisoquinoline-3-carbonitrile,
2-cyclopropyl-4-(3-fluorophenyl)-1-oxo-6-propoxy-1,2-dihydroisoquinoline-3-carbonitrile,
6-(benzyloxy)-2-cyclopropyl-4-(3-fluorophenyl)-1-oxo-1,2-dihydroisoquinoline-3-carbonitrile,
4-(3-fluorophenyl)-2-(3-hydroxypropyl)-6-methoxy-1-oxo-1,2-dihydroisoquinoline-3-carbonitrile,
2-[3-(dimethylamino)-2-hydroxypropyl]-6-methoxy-1-oxo-4-phenyl-1,2-dihydroisoquinoline-3-carbonitrile,
6-methoxy-2-methyl-4-(4-nitrophenoxy)-1-oxo-1,2-dihydroisoquinoline-3-carbonitrile,
6-methoxy-4-(4-methoxyphenyl)-2-methyl-1-oxo-1,2-dihydroisoquinoline-3-carbonitrile,
2-(2-amino-3-hydroxypropyl)-6-methoxy-1-oxo-4-phenyl-1,2-dihydroisoquinoline-3-carbonitrile,
2-(2,3-dihydroxypropyl)-4-(2-fluorophenyl)-6-methoxy-1-oxo-1,2-dihydroisoquinoline-3-carbonitrile,
6-methoxy-2-methyl-1-oxo-4-[3-(trifluoromethyl)phenyl]-1,2-dihydroisoquinoline-3-carbonitrile,
4-[3,5-bis(trifluoromethyl)phenyl]-6-methoxy-2-methyl-1-oxo-1,2-dihydroisoquinoline-3-carbonitrile,
6-[2-(benzyloxy)ethoxy]-2-cyclopropyl-4-(3-fluorophenyl)-1-oxo-1,2-dihydroisoquinoline-3-carbonitrile,
2-[2-(dimethylamino)-3-hydroxypropyl]-6-methoxy-1-oxo-4-phenyl-1,2-dihydroisoquinoline-3-carbonitrile,
2-[3-(dimethylamino)-2-hydroxypropyl]-4-(3-fluorophenyl)-6-methoxy-1-oxo-1,2-dihydroisoquinoline-3-carbonitrile,
4-(2-fluorophenyl)-6-methoxy-1-oxo-1,2-dihydroisoquinoline-3-carbonitrile,
2-(2-hydroxy-3-isopropoxypropyl)-6-methoxy-1-oxo-4-phenyl-1,2-dihydroisoquinoline-3-carbonitrile,
4-(3-aminophenyl)-6-methoxy-2-methyl-1-oxo-1,2-dihydroisoquinoline-3-carbonitrile,
6-methoxy-2-methyl-4-(3-methylphenyl)-1-oxo-1,2-dihydroisoquinoline-3-carbonitrile,
4-(3,5-dichlorophenyl)-6-methoxy-2-methyl-1-oxo-1,2-dihydroisoquinoline-3-carbonitrile,
4-(3-fluorophenyl)-6-methoxy-1-oxo-1,2-dihydroisoquinoline-3-carbonitrile,
2-cyclopropyl-4-(3-fluorophenyl)-1-oxo-6-(tetrahydrofuran-2-ylmethoxy)-1,2-dihydroisoquinoline-3-carbonitrile,
2-cyclopropyl-6-(cyclopropylmethoxy)-4-(3-fluorophenyl)-1-oxo-1,2-dihydroisoquinoline-3-carbonitrile,
2-cyclopropyl-6-(2-ethoxyethoxy)-4-(3-fluorophenyl)-1-oxo-1,2-dihydroisoquinoline-3-carbonitrile,
6-[3-(benzyloxy)propoxy]-2-cyclopropyl-4-(3-fluorophenyl)-1-oxo-1,2-dihydroisoquinoline-3-carbonitrile,
2-cyclopropyl-6-(2,3-dihydro-1,4-benzodioxin-2-ylmethoxy)-4-(3-fluorophenyl)-1-oxo-1,2-dihydroisoquinoline-3-carbonitrile,
2-cyclopropyl-4-(3-fluorophenyl)-1-oxo-6-(tetrahydro-2H-pyran-2-ylmethoxy)-1,2-dihydroisoquinoline-3-carbonitrile,
ethyl {[3-cyano-2-cyclopropyl-4-(3-fluorophenyl)-1-oxo-1,2-dihydroisoquinolin-6-yl]oxy}acetate,
2-cyclopropyl-4-(3-fluorophenyl)-6-(2-hydroxyethoxy)-1-oxo-1,2-dihydroisoquinoline-3-carbonitrile,
4-(4-aminophenoxy)-6-methoxy-2-methyl-1-oxo-1,2-dihydroisoquinoline-3-carbonitrile,
6-methoxy-4-(3-methoxyphenyl)-2-methyl-1-oxo-1,2-dihydroisoquinoline-3-carbonitrile,
6-methoxy-2-methyl-1-oxo-4-phenoxy-1,2-dihydroisoquinoline-3-carbonitrile,
2-cyclopropyl-4-(3-fluorophenyl)-6-(3-hydroxypropoxy)-1-oxo-1,2-dihydroisoquinoline-3-carbonitrile,
2-cyclopropyl-6-(difluoromethoxy)-4-(3-fluorophenyl)-1-oxo-1,2-dihydroisoquinoline-3-carbonitrile,
2-methyl-6-morpholin-4-yl-1-oxo-4-phenyl-1,2-dihydroisoquinoline-3-carbonitrile,
2-methyl-1-oxo-4-phenyl-6-pyridin-4-yl-1,2-dihydroisoquinoline-3-carbonitrile,
2-methyl-1-oxo-4-phenyl-6-pyridin-3-yl-1,2-dihydroisoquinoline-3-carbonitrile,
2-{[3-cyano-2-cyclopropyl-4-(3-fluorophenyl)-1-oxo-1,2-dihydroisoquinolin-6-yl]oxy}-N,N-dimethylacetamide,
2-cyclopropyl-4-(3-fluorophenyl)-6-(2-morpholin-4-yl-2-oxoethoxy)-1-oxo-1,2-dihydroisoquinoline-3-carbonitrile,
4-(4-cyanophenyl)-6-methoxy-2-methyl-1-oxo-1,2-dihydroisoquinoline-3-carbonitrile,
4-(3-cyanophenyl)-6-methoxy-2-methyl-1-oxo-1,2-dihydroisoquinoline-3-carbonitrile,
4-(1,3-benzodioxol-5-yl)-6-methoxy-2-methyl-1-oxo-1,2-dihydroisoquinoline-3-carbonitrile,
2-methyl-6-(4-methylpiperazin-1-yl)-1-oxo-4-phenyl-1,2-dihydroisoquinoline-3-carbonitrile, 2-methyl-1-oxo-4-phenyl-6-piperidin-1-yl-1,2-dihydroisoquinoline-3-carbonitrile,
6-methoxy-2-methyl-1-oxo-4-(1h-pyrazol-3-yl)-1,2-dihydroisoquinoline-3-carbonitrile,
4-[4-(hydroxymethyl)phenyl]-6-methoxy-2-methyl-1-oxo-1,2-dihydroisoquinoline-3-carbonitrile,
ethyl [3-cyano-4-(3-fluorophenyl)-6-methoxy-1-oxoisoquinolin-2(1H)-yl]acetate
2-[2-hydroxy-3-(1H-imidazol-1-yl)propyl]-6-methoxy-1-oxo-4-phenyl-1,2-dihydroisoquinoline-3-carbonitrile,
6-(3-furyl)-2-methyl-1-oxo-4-phenyl-1,2-dihydroisoquinoline-3-carbonitrile,
2-methyl-1-oxo-4-phenyl-6-thiomorpholin-4-yl-1,2-dihydroisoquinoline-3-carbonitrile,
2-cyclopropyl-4-(3-fluorophenyl)-6-[(3-nitropyridin-2-yl)oxy]-1-oxo-1,2-dihydroisoquinoline-3-carbonitrile,
ethyl 4-{[3-cyano-2-cyclopropyl-4-(3-fluorophenyl)-1-oxo-1,2-dihydroisoquinolin-6-yl]oxy}butanoate,
ethyl 5-{[3-cyano-2-cyclopropyl-4-(3-fluorophenyl)-1-oxo-1,2-dihydroisoquinolin-6-yl]oxy}pentanoate,
2-cyclopropyl-4-(3-fluorophenyl)-1-oxo-6-(vinyloxy)-1,2-dihydroisoquinoline-3-carbonitrile,
2-methyl-1-oxo-4-phenyl-6-pyridin-2-yl-1,2-dihydroisoquinoline-3-carbonitrile,
2-(3-ethoxy-2-hydroxypropyl)-6-methoxy-1-oxo-4-phenyl-1,2-dihydroisoquinoline-3-carbonitrile,
2-(2-hydroxy-3-methoxypropyl)-6-methoxy-1-oxo-4-phenyl-1,2-dihydroisoquinoline-3-carbonitrile,
2-(2-hydroxybutyl)-6-methoxy-1-oxo-4-phenyl-1,2-dihydroisoquinoline-3-carbonitrile,
2-(2-hydroxypropyl)-6-methoxy-1-oxo-4-phenyl-1,2-dihydroisoquinoline-3-carbonitrile,
6-[(3-aminopyridin-2-yl)oxy]-2-cyclopropyl-4-(3-fluorophenyl)-1-oxo-1,2-dihydroisoquinoline-3-carbonitrile,
methyl 3-(3-cyano-6-methoxy-2-methyl-1-oxo-1,2-dihydroisoquinolin-4-yl)benzoate,
methyl 4-(3-cyano-6-methoxy-2-methyl-1-oxo-1,2-dihydroisoquinolin-4-yl)benzoate,
2-cyclopropyl-6-[4-(1,3-dioxo-1,3-dihydro-2H-isoindol-2-yl)butoxy]-4-(3-fluorophenyl)-1-oxo-1,2-dihydroisoquinoline-3-carbonitrile,
2-cyclopropyl-6-{[5-(1,3-dioxo-1,3-dihydro-2H-isoindol-2-yl)pentyl]oxy}-4-(3-fluorophenyl)-1-oxo-1,2-dihydroisoquinoline-3-carbonitrile,
2-cyclopropyl-6-{[6-(1,3-dioxo-1,3-dihydro-2H-isoindol-2-yl)hexyl]oxy}-4-(3-fluorophenyl)-1-oxo-1,2-dihydroisoquinoline-3-carbonitrile,
2-{[3-cyano-2-cyclopropyl-4-(3-fluorophenyl)-1-oxo-1,2-dihydroisoquinolin-6-yl]oxy}-N,N-dimethylethanaminium trifluoroacetate,
3-{[3-cyano-2-cyclopropyl-4-(3-fluorophenyl)-1-oxo-1,2-dihydroisoquinolin-6-yl]oxy}-N,N-dimethylpropan-1-aminium trifluoroacetate,
6-{[3-cyano-2-cyclopropyl-4-(3-fluorophenyl)-1-oxo-1,2-dihydroisoquinolin-6-yl]oxy}hexan-1-aminium trifluoroacetate,
4-{[3-cyano-2-cyclopropyl-4-(3-fluorophenyl)-1-oxo-1,2-dihydroisoquinolin-6-yl]oxy}butanoic acid,
4-ethynyl-6-methoxy-2-methyl-1-oxo-1,2-dihydroisoquinoline-3-carbonitrile,
5-{[3-cyano-2-cyclopropyl-4-(3-fluorophenyl)-1-oxo-1,2-dihydroisoquinolin-6-yl]oxy}pentanoic acid,
4-{[3-cyano-2-cyclopropyl-4-(3-fluorophenyl)-1-oxo-1,2-dihydroisoquinolin-6-yl]oxy}butan-1-aminium trifluoroacetate,
5-{[3-cyano-2-cyclopropyl-4-(3-fluorophenyl)-1-oxo-1,2-dihydroisoquinolin-6-yl]oxy}pentan-1-aminium trifluoroacetate,
6-(4-hydroxypiperidin-1-yl)-2-methyl-1-oxo-4-phenyl-1,2-dihydroisoquinoline-3-carbonitrile,
2-allyl-4-(3-chlorophenyl)-6-methoxy-1-oxo-1,2-dihydroisoquinoline-3-carbonitrile,
4-(3-fluorophenyl)-6-methoxy-1-oxo-2-[2-(3-oxo-4-phenylpiperazin-1-yl)ethyl]-1,2-dihydroisoquinoline-3-carbonitrile,
4-({2-[3-cyano-4-(3-fluorophenyl)-6-methoxy-1-oxoisoquinolin-2(1h)-yl]ethyl}-amino)benzoic acid,
3-({2-[3-cyano-4-(3-fluorophenyl)-6-methoxy-1-oxoisoquinolin-2(1H)-yl]ethyl}-amino)benzoic acid,
2-({2-[3-cyano-4-(3-fluorophenyl)-6-methoxy-1-oxoisoquinolin-2(1H)-yl]ethyl}-amino)benzoic acid,
4-(3-chlorophenyl)-2-(2,3-dihydroxypropyl)-6-methoxy-1-oxo-1,2-dihydroisoquinoline-3-carbonitrile,
2-cyclopropyl-6-(cyclopropyloxy)-4-(3-fluorophenyl)-1-oxo-1,2-dihydroisoquinoline-3-carbonitrile,
2-cyclopropyl-4-(3-fluorophenyl)-6-[(5-morpholin-4-yl-5-oxopentyl)oxy]-1-oxo-1,2-dihydroisoquinoline-3-carbonitrile,
2-cyclopropyl-4-(3-fluorophenyl)-6-(4-morpholin-4-yl-4-oxobutoxy)-1-oxo-1,2-dihydroisoquinoline-3-carbonitrile,
5-{[3-cyano-2-cyclopropyl-4-(3-fluorophenyl)-1-oxo-1,2-dihydroisoquinolin-6-yl]oxy}pentyl acetate,
2-cyclopropyl-4-(3-fluorophenyl)-6-(4-hydroxybutoxy)-1-oxo-1,2-dihydroisoquinoline-3-carbonitrile,
6-(cyanomethoxy)-2-cyclopropyl-4-(3-fluorophenyl)-1-oxo-1,2-dihydroisoquinoline-3-carbonitrile,
2-cyclopropyl-4-(3-fluorophenyl)-6-[(5-hydroxypentyl)oxy]-1-oxo-1,2-dihydroisoquinoline-3-carbonitrile,
2-(2,3-dihydroxypropyl)-6-methoxy-1-oxo-4-[3-(trifluoromethyl)phenyl]-1,2-dihydroisoquinoline-3-carbonitrile,
3-cyano-2-cyclopropyl-4-(3-fluorophenyl)-1-oxo-1,2-dihydroisoquinolin-6-yl morpholine-4-carboxylate,
2-{3-hydroxy-2-[(pyridin-3-ylmethyl)amino]propyl}-6-methoxy-1-oxo-4-phenyl-1,2-dihydroisoquinoline-3-carbonitrile,
3-cyano-2-cyclopropyl-4-(3-fluorophenyl)-1-oxo-1,2-dihydroisoquinolin-6-yl acetate,
4-(3-fluorophenyl)-2-{2-[(2-hydroxy-2,3-dihydro-1H-inden-1-yl)amino]ethyl}-6-methoxy-1-oxo-1,2-dihydroisoquinoline-3-carbonitrile,
methyl (2S)-({2-[3-cyano-4-(3-fluorophenyl)-6-methoxy-1-oxoisoquinolin-2(1H)-yl]ethyl}-amino)(phenyl)ethanoate,
methyl (2R)-({2-[3-cyano-4-(3-fluorophenyl)-6-methoxy-1-oxoisoquinolin-2(1h)-yl]ethyl}-amino)(phenyl)ethanoate,
2-(2-hydroxy-2-methylpropyl)-6-methoxy-1-oxo-4-phenyl-1,2-dihydroisoquinoline-3-carbonitrile,
3-cyano-2-cyclopropyl-4-(3-fluorophenyl)-1-oxo-1,2-dihydroisoquinolin-6-yl benzoate,
3-cyano-2-cyclopropyl-4-(3-fluorophenyl)-1-oxo-1,2-dihydroisoquinolin-6-yl methanesulfonate,
6-methoxy-2-methyl-1-oxo-4-(phenylethynyl)-1,2-dihydroisoquinoline-3-carbonitrile,
2-{[3-cyano-2-cyclopropyl-4-(3-fluorophenyl)-1-oxo-1,2-dihydroisoquinolin-6-yl]oxy}ethyl morpholine-4-carboxylate,
2-allyl-1-oxo-4-phenyl-6-thien-3-yl-1,2-dihydroisoquinoline-3-carbonitrile, 2-allyl-6-(3-furyl)-1-oxo-4-phenyl-1,2-dihydroisoquinoline-3-carbonitrile,
5-{[3-cyano-2-cyclopropyl-4-(3-fluorophenyl)-1-oxo-1,2-dihydroisoquinolin-6-yl]oxy}pentyl morpholine-4-carboxylate,
3-{[3-cyano-2-cyclopropyl-4-(3-fluorophenyl)-1-oxo-1,2-dihydroisoquinolin-6-yl]oxy}propyl morpholine-4-carboxylate,
4-(3-fluorophenyl)-2-(2-{[(1R)-2-hydroxy-1-phenylethyl]amino}-ethyl)-6-methoxy-1-oxo-1,2-dihydroisoquinoline-3-carbonitrile,
ethyl ({2[3-cyano-4-(3-fluorophenyl)-6-methoxy-1-oxoisoquinolin-2(1H)-yl]ethyl}-amino)(phenyl)acetate,
2-(2,3-dihydroxypropyl)-4-(3-fluorophenyl)-1-oxo-6-thien-3-yl-1,2-dihydroisoquinoline-3-carbonitrile,
6-(1-benzothien-3-yl)-2-(2,3-dihydroxypropyl)-4-(3-fluorophenyl)-1-oxo-1,2-dihydroisoquinoline-3-carbonitrile,
methyl [3-cyano-4-(3-fluorophenyl)-6-methoxy-1-oxoisoquinolin-2(1H)-yl]acetate,
2-(2,3-dihydroxypropyl)-4-(3-fluorophenyl)-6-(3-furyl)-1-oxo-1,2-dihydroisoquinoline-3-carbonitrile,
2-(2,3-dihydroxypropyl)-4-(3-fluorophenyl)-6-[2-(hydroxymethyl)thien-3-yl]-1-oxo-1,2-dihydroisoquinoline-3-carbonitrile,
tert-butyl {[3-cyano-2-cyclopropyl-4-(3-fluorophenyl)-1-oxo-1,2-dihydroisoquinolin-6-yl]oxy}acetate,
[3-cyano-4-(3-fluorophenyl)-6-methoxy-1-oxoisoquinolin-2(1H)-yl]acetic acid,
{[3-cyano-2-cyclopropyl-4-(3-fluorophenyl)-1-oxo-1,2-dihydroisoquinolin-6-yl]oxy}acetic acid,
({2-[3-cyano-4-(3-fluorophenyl)-6-methoxy-1-oxoisoquinolin-2(1H)-yl]ethyl}amino)-(phenyl)acetic acid,
2-[3-hydroxy-2-(1h-1,2,3-triazol-1-yl)propyl]-6-methoxy-1-oxo-4-phenyl-1,2-dihydroisoquinoline-3-carbonitrile,
methyl ({2-[3-cyano-4-(3-fluorophenyl)-6-methoxy-1-oxoisoquinolin-2(1H)-yl]ethyl}-amino)(pyridin-3-yl)acetate,
2-cyclopropyl-4-(3-fluorophenyl)-1-oxo-6-(2-oxo-2-pyrrolidin-1-ylethoxy)-1,2-dihydroisoquinoline-3-carbonitrile,
methyl 2-[3-cyano-4-(3-fluorophenyl)-6-methoxy-1-oxoisoquinolin-2(1H)-yl]propanoate,
2-cyclopropyl-4-(3-fluorophenyl)-1-oxo-6-(2-oxo-2-piperidin-1-ylethoxy)-1,2-dihydroisoquinoline-3-carbonitrile,
N-benzyl-2-{[3-cyano-2-cyclopropyl-4-(3-fluorophenyl)-1-oxo-1,2-dihydroisoquinolin-6-yl]oxy}-N-methylacetamide,
2-{[3-cyano-2-cyclopropyl-4-(3-fluorophenyl)-1-oxo-1,2-dihydroisoquinolin-6-yl]oxy}-N-methoxy-N-methylacetamide,
2-{[3-cyano-2-cyclopropyl-4-(3-fluorophenyl)-1-oxo-1,2-dihydroisoquinolin-6-yl]oxy}-N-(2-methoxyethyl)acetamide,
2-{[3-cyano-2-cyclopropyl-4-(3-fluorophenyl)-1-oxo-1,2-dihydroisoquinolin-6-yl]oxy}-N-(3-methoxypropyl)acetamide,
2-cyclopropyl-4-(3-fluorophenyl)-1-oxo-6-[2-oxo-2-(3-oxopiperazin-1-yl)ethoxy]-1,2-dihydroisoquinoline-3-carbonitrile,
N-benzyl-2-{[3-cyano-2-cyclopropyl-4-(3-fluorophenyl)-1-oxo-1,2-dihydroisoquinolin-6-yl]oxy}acetamide,
6-(2-azetidin-1-yl-2-oxoethoxy)-2-cyclopropyl-4-(3-fluorophenyl)-1-oxo-1,2-dihydroisoquinoline-3-carbonitrile,
2-{[3-cyano-2-cyclopropyl-4-(3-fluorophenyl)-1-oxo-1,2-dihydroisoquinolin-6-yl]oxy}-N-(2-methoxyethyl)-N-methylacetamide,
N,N-dibenzyl-2-{[3-cyano-2-cyclopropyl-4-(3-fluorophenyl)-1-oxo-1,2-dihydroisoquinolin-6-yl]oxy}acetamide,
2-allyl-6-methoxy-1-oxo-4-pyridin-2-yl-1,2-dihydroisoquinoline-3-carbonitrile,
6-methoxy-2-methyl-1-oxo-4-(1h-1,2,3-triazol-5-yl)-1,2-dihydroisoquinoline-3-carbonitrile,
methyl {[(3-cyano-6-methoxy-2-methyl-1-oxo-1,2-dihydroisoquinolin-4-yl)oxy]sulfonyl}carbamate,
7-cyclopropyl-9-(3-fluorophenyl)-2-methyl-6-oxo-1,2,6,7-tetrahydrofuro [3,2-f]-isoquinoline-8-carbonitrile,
5-allyl-2-cyclopropyl-4-(3-fluorophenyl)-6-methoxy-1-oxo-1,2-dihydroisoquinoline-3-carbonitrile,
2-cyclopropyl-5-(2,3-dihydroxypropyl)-4-(3-fluorophenyl)-6-methoxy-1-oxo-1,2-dihydroisoquinoline-3-carbonitrile,
2-(2,3-dihydroxypropyl)-6-methoxy-1-oxo-4-pyridin-2-yl-1,2-dihydroisoquinoline-3-carbonitrile,
2-(2,3-dihydroxypropyl)-6-methoxy-1-oxo-4-pyridin-2-yl-1,2-dihydroisoquinoline-3-carbonitrile,
2-allyl-4-(3-fluorophenyl)-6-(6-methylpyridin-2-yl)-1-oxo-1,2-dihydroisoquinoline-3-carbonitrile,
2-{[3-cyano-4-(3-fluorophenyl)-6-methoxy-1-oxoisoquinolin-2(1h)-yl]methyl}-1h-benzimidazol-1-ium chloride,
4-(3-fluorophenyl)-6-methoxy-1-oxo-2-{2-[(pyridin-2-ylmethyl)amino]ethyl}-1,2-dihydroisoquinoline-3-carbonitrile,
2-allyl-4-(3-fluorophenyl)-1-oxo-6-(1H-pyrazol-4-yl)-1,2-dihydroisoquinoline-3-carbonitrile,
2-[2-allyl-3-cyano-4-(3-fluorophenyl)-1-oxo-1,2-dihydroisoquinolin-6-yl]-4-methylpyridinium trifluoroacetate,
2-[3-cyano-2-(2,3-dihydroxypropyl)-4-(3-fluorophenyl)-1-oxo-1,2-dihydroisoquinolin-6-yl]-6-methylpyridinium trifluoroacetate,
4-(3-chlorophenyl)-2-{[(4S)-2,2-diethyl-1,3-dioxolan-4-yl]methyl}-6-methoxy-1-oxo-1,2-dihydroisoquinoline-3-carbonitrile,
2-allyl-6-methoxy-1-oxo-4-pyridin-3-yl-1,2-dihydroisoquinoline-3-carbonitrile,
2-(2,3-dihydroxypropyl)-6-methoxy-4-(1-oxidopyridin-2-yl)-1-oxo-1,2-dihydroisoquinoline-3-carbonitrile, and
4-(3-chlorophenyl)-2-[(2S)-2,3-dihydroxypropyl]-6-methoxy-1-oxo-1,2-dihydroisoquinoline-3-carbonitrile.

2. A method of treating a condition in a mammal, the treatment of which is effected or facilitated by $K_v$ 1.5 inhibition, which comprises administering a compound of claim 1 in an amount that is effective at inhibiting $K_v$ 1.5 wherein the condition is cardiac arrhythmia.

3. A method of claim 2, wherein the cardiac arrythmia is selected from the group consisting of atrial flutter, atrial arrhythmia and supraventricular tachycardia.

4. A method of claim 3, wherein the cardiac arrythmia is atrial fibrillation.

5. A method of treating cardiac arrythmia comprising administering a compound of claim 1 with a compound selected from one of the classes of compounds consisting of antiarrhythmic agents having Kv 1.5 blocking activity, ACE inhibitors, angiotensin II antagonists, cardiac glycosides, L-type calcium channel blockers, T-type calcium channel blockers, selective and nonselective beta blockers, endothelin antagonists, thrombin inhibitors, aspirin, nonselective NSAIDs, warfarin, factor Xa inhibitors, low molecular weight heparin, unfractionated heparin, clopidogrel, ticlopidine, IIb/IIIa receptor antagonists, 5HT receptor antagonists, integrin receptor antagonists, thromboxane receptor antagonists, TAFI inhibitors and P2T receptor antagonists.

6. A pharmaceutical formulation comprising a pharmaceutically acceptable carrier and the compound of claim 1 or a pharmaceutically acceptable crystal form or hydrate thereof.

7. A pharmaceutical composition made by combining the compound of claim 1 and a pharmaceutically acceptable carrier.

\* \* \* \* \*